US008263083B2

(12) United States Patent
Oflazoglu et al.

(10) Patent No.: US 8,263,083 B2
(45) Date of Patent: Sep. 11, 2012

(54) COMBINATION THERAPY WITH ANTIBODY-DRUG CONJUGATES

(75) Inventors: Ezogelin Oflazoglu, Bothell, WA (US); Eric Sievers, Bothell, WA (US); Hans-Peter Gerber, Bothell, WA (US)

(73) Assignee: Seattle Genetics, Inc., Bothell, WA (US)

( * ) Notice: Subject to any disclaimer, the term of this patent is extended or adjusted under 35 U.S.C. 154(b) by 174 days.

(21) Appl. No.: 12/681,599

(22) PCT Filed: Oct. 8, 2008

(86) PCT No.: PCT/US2008/079224
§ 371 (c)(1),
(2), (4) Date: Apr. 2, 2010

(87) PCT Pub. No.: WO2009/048967
PCT Pub. Date: Apr. 16, 2009

(65) Prior Publication Data
US 2010/0215671 A1 Aug. 26, 2010

Related U.S. Application Data

(60) Provisional application No. 60/979,594, filed on Oct. 12, 2007, provisional application No. 61/027,668, filed on Feb. 11, 2008, provisional application No. 61/040,641, filed on Mar. 28, 2008.

(51) Int. Cl.
*A61K 39/395* (2006.01)

(52) U.S. Cl. ................... 424/183.1; 424/178.1

(58) Field of Classification Search ................. None
See application file for complete search history.

(56) References Cited

U.S. PATENT DOCUMENTS

| 5,165,922 | A  | * | 11/1992 | Hellstrom et al. ......... 424/155.1 |
| 6,150,508 | A  | * | 11/2000 | Murphy et al. ............ 530/387.1 |
| 7,090,843 | B1 |   | 8/2006  | Francisco et al. |
| 7,659,241 | B2 |   | 2/2010  | Senter et al. |
| 7,829,531 | B2 |   | 11/2010 | Senter et al. |
| 7,851,437 | B2 |   | 12/2010 | Senter et al. |
| 2004/0018194 | A1 | | 1/2004 | Francisco et al. |
| 2007/0134243 | A1 | | 6/2007 | Gazzard et al. |
| 2008/0213289 | A1 | | 9/2008 | Francisco et al. |
| 2011/0064753 | A1 | | 3/2011 | Senter et al. |

FOREIGN PATENT DOCUMENTS

| WO | 2007/044616 | * | 4/2007 |
| WO | 2008/025020 | * | 2/2008 |
| WO | WO 2008/103916 A2 | | 8/2008 |

OTHER PUBLICATIONS

"Phase II Study of Monoclonal Antibody SGN-30, Gemcitabine, Vinorelbine, and Pegylated Doxorubicin HCl Liposome in Patients With Relapsed or Refractory Hodgkin's Lymphoma," ClinicalTrials.gov, Clinical Trials Identifier: NCT00337194, 4 pages (2006). [Retrieved from the Internet Jan. 20, 2011: <URL:http://clinicaltrials.gov/archive/NCT00337194/2006_06_14 >].
"Seattle Genetics and Millennium Announce Positive Top-Line Brentuximab Vedotin (SGN-35) Data from Phase II Trial in Relapsed or Refractory ALCL," Business Wire, 2 pages (2010). [Retrieved from the Internet Oct. 13, 2010: <URL:http://investor.seagen.com/phoenix.zhtml?c=124860&p=irol-newsArticle_pf&ID=1474836&highlight=>].
"Seattle Genetics and Millennium Announce Positive Top-Line Brentuximab Vedotin (SGN-35) Data from Pivotal Trial in Relapsed and Refractory Hodgkin Lymphoma," Business Wire, 2 pages (2010). [Retrieved from the Internet Oct. 13, 2010: <URL:http://investsor.seagen.com/phoenix.zhtml?c=124860&p=irol-newsArticle_pf&ID=1474836&highlight=>].
Bartlett et al., "A phase 1 multi-dose study of SGN-30 immunotherapy in patients with refractory or recurrent CD30+ hematologic malignancies," Blood, doi:10.1182/blood-2007-07-099317, (print ISSN 0006-4971, online ISSN 1528-0020), 30 pages, (First Edition paper 2007).
Blund et al., "Serious pulmonary toxicity in patients with Hodgkin's lymphoma with SGN-30, gemcitabine, vinorelbine, and liposomal doxorubicin is associated with an FcyRllla-158 V/F polymorphism," Annals of Oncology, doi:10.1093/annonc/mdq211, 9 pages, (2010).
Buglio et al., "Novel small-molecule therapy of Hodgkin lymphoma," Expert Rev. Anticancer Ther., 7(5):735-740, (2007).
Byrne et al., "Salvage Therapy in Hodgkin's Lymphoma," Oncologist, 12:156-16, (2007).
Cerveny et al., "In vitro Synergy Between Gemcitabine and SGN-15 Against Ovarian Cancer cells," Seattle Genetics, Abstract No. 2899, 93rd Annual Meeting of the American Association of Cancer Research (AACR) in San Francisco, CA (2002).
Duggan et al., "Randomized Comparison of ABVD and MOPP/ABV Hybrid for the Treatment of Advanced Hodgkin's Disease: Report of an Intergroup Trial," Journal of Clinical Oncology, 21(4):607-614 (2003).
Kanzler et al., "Hodgkin and Reed-Sternberg—like cells in B-cell chronic lymphocytic leukemia represent the outgrowth of single germinal-center B-cell—derived clones: potential precursors of Hodgkin and Reed-Sternberg cells in Hodgkin's disease," Blood, 95(3):1023-1031 (2002).
Oflazoglu et al., "Combination of the anti-CD30-auristatin-E antibody-drug conjugate (SGN-35) with chemotherapy improves antitumour activity in Hodgkin lymphoma," Annals of Oncology, 19(4):iv235-iv236, (2008).
Oflazoglu et al., "Combination of the anti-CD30-auristatin-E antibody-drug conjugate (SGN-35) with chemotherapy improves antitumor activity in Hodgkin lymphoma," British Journal of Haematology, 142:69-73 (2008).
PCT International Preliminary Report on Patentability (Chapter I) of Apr. 13, 2010 for application PCT/US08/079224.
PCT Search Report for application PCT/US08/079224 mailed Dec. 14, 2008.
Pollack et al., "Treatment parameters modulating regression of human melanoma xenografts by an antibody-drug conjugate (CR011-vcMMAE) targeting GPNMB," Cancer Chemother Pharmacol, 60:423-435, (2007).
Santoro et al., "Gemcitabine in the Treatment of Refractory Hodgkin's Disease: Results of a Multicenter Phase II Study," Journal of Clinical Oncology, 18(13): 2615-2619, (2000).
"Highlights in Lymphoma from the 2011 ASH Annual Meeting," Clinical Advances in Hematology & Oncology, vol. 10, Issue 2, Supplement 1, (2012).
Francisco et al., "cAC10-vcMMAE, an anti-CD30-monomethyl auristatin E conjugate with potent and selective antitumor activity," Blood, 102:1458-1465, (2004).

* cited by examiner

Primary Examiner — Sheela J Huff
(74) Attorney, Agent, or Firm — Alston & Bird LLP

(57) ABSTRACT

Methods for the treatment of Hodgkin's lymphoma comprising administering both a chemotherapeutic regimen and an antibody-drug conjugate compound to a subject in need thereof are provided.

13 Claims, 9 Drawing Sheets

US 8,263,083 B2

COMBINATION THERAPY WITH ANTIBODY-DRUG CONJUGATES

CROSS-REFERENCE TO RELATED APPLICATIONS

This application is a national stage application under 35 U.S.C. 371 of International Application No. PCT/US2008/079224 filed Oct. 8, 2008, which claims the benefit of U.S. Provisional Patent Application No. 60/979,594, filed Oct. 12, 2007; U.S. Provisional Patent Application No. 61/027,668, filed Feb. 11, 2008; and U.S. Provisional Patent Application No. 61/040,641, filed Mar. 28, 2008; all the disclosures of which are incorporated by reference herein in their entirety.

REFERENCE TO A "SEQUENCE LISTING"

This application contains a sequence listing provided in the form of a text file named 018891_006610US_SEQLST.txt, which was created on Apr. 1, 2010 and containing 19,600 bytes. The information contained in this file is hereby incorporated by reference in its entirely.

FIELD

The present invention relates, inter alia, to methods for the treatment of Hodgkin lymphoma comprising administering both a chemotherapeutic regimen and an antibody-drug conjugate compound to a subject in need thereof.

BACKGROUND

Hodgkin lymphoma (HL) is a neoplasm of lymphoid tissue that is defined histopathologically by the presence of the malignant Hodgkin-Reed-Sternberg (HRS) cells. The characteristic surface antigen expressed on HRS cells is CD30. There are an estimated 8,000 new HL cases diagnosed annually in the United States and Canada. Advances in the use of combined chemotherapy and radiotherapy in HL over the past half-century have resulted in a durable remission rate of approximately 70%. However, these multi-agent regimens confer a significant morbidity on patients, including secondary malignancies, cardiac disease, and infertility. Furthermore, approximately 30% of patients presenting with HL will become refractory to initial therapy or will relapse. Salvage chemotherapy regimens and autologous stem cell transplant (ASCT) are secondary options for these patients, but both are associated with significant morbidity and limited long term disease control. Patients who relapse after ASCT or are ineligible for salvage therapy have a very poor prognosis. Currently, there is a lack of well-tolerated, efficacious treatment options for these patients.

Gemcitabine, alone or in combination with other chemotherapy, has been evaluated in the pre and post-ASCT setting. In the transplant naïve setting, relapsed or refractory HL patients treated with gemcitabine achieve response rates of 39% (Santoro et al., J Clin Oncol 2000 18(13):2615-9). In the relapsed/refractory setting where the majority of patients have received prior autologous or allogeneic transplant, gemcitabine response rates are diminished (22%) and hematologic toxicity of the regimen necessitates dose reduction to 1000 mg/m$^2$ (Venkatesh et al., Clin lymphoma 2004 5(2):110-5). A combination regimen utilizing gemcitabine, vinorelbine and pegylated liposomal doxorubicin (GVD) has demonstrated promising efficacy in relapsed/refractory HL. Overall response rates of 70% were observed in the combined analysis of pre and post-ASCT patients, however with dose limiting toxicities of mucositis in the pre-ASCT population and febrile neutropenia in the post-ASCT population (Bartlett al., CALGB 59804 Ann Oncoo, 2007 18(6): 1071-9). Only 32% and 26% of patients who were transplant naïve and post-ASCT, respectively, were able to receive all doses on schedule at full dose. For patients who do not respond to standard chemotherapy or who relapse, the only potentially curative therapy is high-dose chemotherapy in combination with stem cell transplantation. This treatment is also associated with significant morbidity and mortality, and a 5-year survival rate of less than 50%. Thus, there continues to be an unmet medical need for patients suffering from HL. The present invention addresses this and other needs.

DETAILED DESCRIPTION OF EXEMPLARY EMBODIMENTS

A. General Introduction

Figure 1:
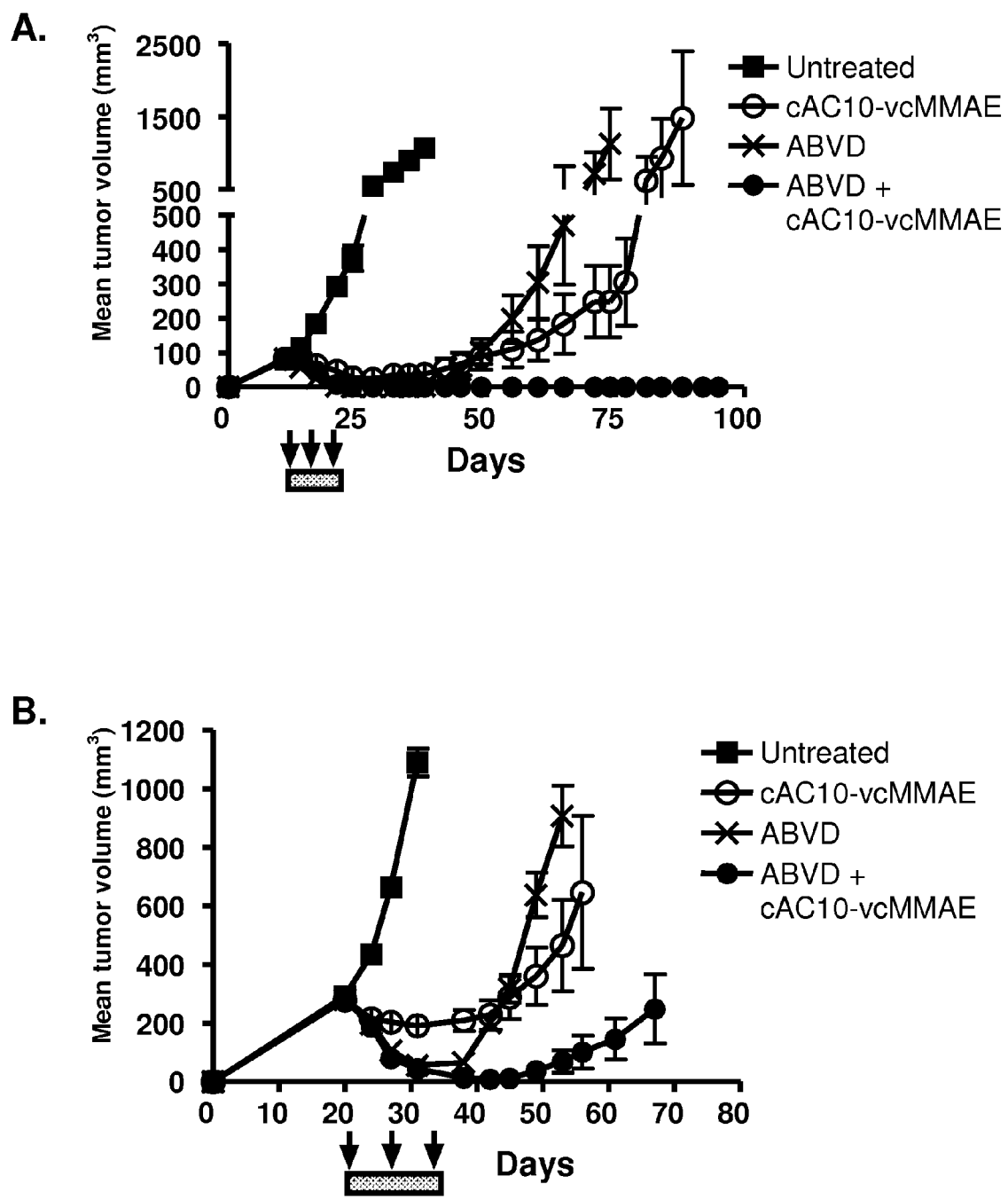
FIG. 1A: Antitumor activity of cAC10-vcMMAE alone or in combination with ABVD on subcutaneous L540cy HL tumors in SCID mice. SCID mice were implanted with L540cy HL cells in the right flank. Groups of mice (9-10/group) were untreated or received cAC10-vcMMAE (1 mg/kg, q4dx3, ip) and/or ABVD: Adriamycin (1 mg/kg, q4dx3, i.v.), Bleomycin (7.5 u/kg, q4dx3, i.p.), Vinblastine (0.015 mg/kg, q4dx3, i.p.), and Dacarbazine (20 mg/kg, q3dx4, i.p.) when tumor size averaged approximately 100 mm$^3$.
FIG. 1B: Antitumor activity of cAC10-vcMMAE alone or in combination with ABVD on subcutaneous L540cy HL tumors in SCID mice. SCID mice were implanted with L540cy HL cells in the right flank. Groups of mice (9-10/group) were untreated or received cAC10-vcMMAE (1 mg/kg, q4dx3, ip) and/or ABVD: Adriamycin (0.75 mg/kg, q4dx3, i.v.), Bleomycin (6 u/kg, q4dx3, i.p.), Vinblastine (0.01 mg/kg, q4dx3, i.p.), and Dacarbazine (15 mg/kg, q3dx4, i.p.) when tumor size averaged approximately 300 mm$^3$.

The present invention provides, inter alia, methods for treating Hodgkin lymphoma. The present inventors have discovered that combination therapy with two different classes of anticancer compounds, antibody-drug conjugate compounds and chemotherapeutic agents, can improve a therapeutic benefit for subjects suffering from HL. In particular, the present inventors have found that combination therapy with either gemcitabine or an ABVD regimen and an anti-CD30 antibody conjugated to an auristatin compound provides synergistic therapeutic effects in the treatment of HL. Before the advent of the present invention, it could not have been expected that a chemotherapeutic agent and an anti-CD30 antibody conjugated to an auristatin compound would have a synergistic effect in the treatment of HL.

For clarity of disclosure, and not by way of limitation, the detailed description of the invention is divided into the subsections which follow.

B. Summary

The present invention is based, inter alia, on the discovery that combination therapy with either gemcitabine or an ABVD regimen and an anti-CD30 antibody conjugated to an auristatin compound provides synergistic therapeutic effects in the treatment of HL.

In one embodiment, methods for treating Hodgkin lymphoma in a subject are provided. The methods comprise administering to a subject in need thereof gemcitabine and an antibody-drug conjugate compound. Administration of the antibody-drug conjugate compound and gemcitabine provides a synergistic effect in the treatment of Hodgkin lymphoma in the patient. The antibody-drug conjugate compound is an anti-CD30 antibody conjugated to an auristatin compound.

In another embodiment, methods for treating Hodgkin lymphoma in a subject consist essentially of administering to a subject in need thereof gemcitabine and an antibody-drug conjugate compound. Administration of the antibody-drug conjugate compound and gemcitabine provides a synergistic effect in the treatment of Hodgkin lymphoma in the patient. The antibody-drug conjugate compound is an anti-CD30 antibody conjugated to an auristatin compound.

The antibody-drug conjugate compound is typically delivered over a treatment cycle. The treatment cycle can be any suitable length of time. In one aspect, it is three or four weeks.

Also provided by the present invention is the use of an antibody-drug conjugate compound in the manufacture of a medicament to be administered in combination therapy with gemcitabine for the treatment of Hodgkin lymphoma in a subject. Administration of the antibody-drug conjugate compound and gemcitabine provides a synergistic effect in the treatment of Hodgkin lymphoma in the patient. The antibody-drug conjugate compound is an anti-CD30 antibody conjugated to an auristatin compound.

In one embodiment, methods of the present invention comprise administering to a subject in need thereof a chemotherapeutic regimen comprising doxorubicin, bleomycin, vinblastine and dacarbazine (ABVD) and an antibody-drug conjugate compound. Administration of the antibody-drug conjugate compound and the chemotherapeutic regimen comprising doxorubicin, bleomycin, vinblastine, and dacarbazine provides a synergistic effect in the treatment of Hodgkin lymphoma in the patient. The antibody-drug conjugate compound is an anti-CD30 antibody conjugated to an auristatin compound.

In another embodiment, the methods for treating Hodgkin lymphoma in a subject consist essentially of administering to a subject in need thereof a chemotherapeutic regimen comprising doxorubicin, bleomycin, vinblastine and dacarbazine and an antibody-drug conjugate compound. Administration of the antibody-drug conjugate compound and the chemotherapeutic regimen comprising doxorubicin, bleomycin, vinblastine and dacarbazine provides a synergistic effect in the treatment of Hodgkin lymphoma in the patient. The antibody-drug conjugate compound is an anti-CD30 antibody conjugated to an auristatin compound.

The antibody-drug conjugate compound is typically delivered over a treatment cycle. The treatment cycle can be any suitable length of time. In one aspect, it is three or four weeks.

Also provided by the present invention is the use of an antibody-drug conjugate compound in the manufacture of a medicament to be administered in combination therapy with the chemotherapeutic regimen comprising doxorubicin, bleomycin, vinblastine, and dacarbazine for the treatment of Hodgkin lymphoma in a subject. Administration of the antibody-drug conjugate compound and the chemotherapeutic regimen provides a synergistic effect in the treatment of Hodgkin lymphoma in the patient. The antibody-drug conjugate compound is an anti-CD30 antibody conjugated to an auristatin compound.

C. Definitions and Abbreviations

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The term "inhibit" or "inhibition of" as used herein means to a reduce by a measurable amount, or to prevent entirely.

The transitional phrase "consisting essentially of" as used herein limits the scope of a claim to the specified active agents or steps and those additional active agents and steps that do not materially affect the properties of the specified active agents.

The term "agent" as used herein means an element, compound, or molecular entity, including, e.g., a pharmaceutical, therapeutic, or pharmacologic compound. Agents can be natural or synthetic or a combination thereof. A "therapeutic anti-cancer agent" is an agent that exerts a therapeutic (e.g., beneficial) effect on cancer cells either alone or in combination with another agent. Typically, therapeutic anti-cancer agents useful in accordance with the methods and compositions described herein are those that exert a cytotoxic and/or cytostatic effect on target cells.

"Cytotoxic effect," in reference to the effect of an agent on a cell, means killing of the cell. "Cytostatic effect" means an inhibition of cell proliferation. A "cytotoxic agent" means an agent that has a cytotoxic or cytostatic effect on a cell, thereby depleting or inhibiting the growth of, respectively, cells within a cell population.

The term "deplete," in the context of the effect of an anti-CD30-antibody-drug conjugate on CD30-expressing cells, refers to a reduction or elimination of the CD30-expressing cells.

The terms "specific binding" and "specifically binds" mean that the anti-CD30 antibody will react, in a highly selective manner, with its corresponding target, CD30 and not with the multitude of other antigens. Typically, the anti-CD30 antibody binds with an affinity of at least about $1 \times 10^{-7}$ M, and preferably $10^{-8}$ M to $10^{-9}$ M, $10^{-10}$ M, $10^{-11}$ M, or $10^{-12}$ M.

The term "antibody" as used herein refers to (a) immunoglobulin polypeptides and immunologically active portions of immunoglobulin polypeptides, i.e., polypeptides of the immunoglobulin family, or fragments thereof, that contain an antigen binding site that immunospecifically binds to a specific antigen (e.g., CD30), or (b) conservatively substituted derivatives of such immunoglobulin polypeptides or fragments that immunospecifically bind to the antigen (e.g., CD30). Antibodies are generally described in, for example, Harlow & Lane, *Antibodies: A Laboratory Manual* (Cold Spring Harbor Laboratory Press, 1988). As used herein, the term "antibody" includes antibodies that have been modified by covalent attachment of a heterologous molecule such as, e.g., by attachment of a heterologous polypeptide, or by glycosylation, acetylation or phosphorylation not normally associated with the antibody, and the like.

The term "monoclonal antibody" refers to an antibody that is derived from a single cell clone, including any eukaryotic or prokaryotic cell clone, or a phage clone, and not the method by which it is produced. Thus, the term "monoclonal antibody" as used herein is not limited to antibodies produced through hybridoma technology.

The terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In certain embodiments, the two sequences are the same length.

The term "substantially identical," in the context of two nucleic acids or polypeptides, refers to two or more sequences or subsequences that have at least 70% or at least 75% identity; more typically at least 80% or at least 85% identity; and even more typically at least 90%, at least 95%, or at least 98% identity (as determined using one of the methods set forth).

"Similarity" or "percent similarity" in the context of two or more polypeptide sequences, refer to two or more sequences or subsequences that have a specified percentage of amino acid residues that are the same or conservatively substituted when compared and aligned for maximum correspondence, as measured using one of the methods set forth infra. By way of example, a first amino acid sequence can be considered similar to a second amino acid sequence when the first amino acid sequence is at least 50%, 60%, 70%, 75%, 80%, 90%, or even 95% identical, or conservatively substituted, to the second amino acid sequence when compared to an equal number of amino acids as the number contained in the first sequence, or when compared to an alignment of polypeptides that has been aligned by a computer similarity program known in the art (see infra).

The terms "substantial similarity" or "substantial similarity," in the context of polypeptide sequences, indicates that a polypeptide region has a sequence with at least 70%, typically at least 80%, more typically at least 85%, and even more typically at least 90% or at least 95% sequence similarity to a reference sequence. For example, a polypeptide is substantially similar to a second polypeptide, for example, where the two peptides differ by one or more conservative substitutions.

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, *Proc. Natl. Acad. Sci. USA* 87:2264-2268, modified as in Karlin and Altschul, 1993, *Proc. Natl. Acad. Sci. USA* 90:5873-5877. Such an algorithm is incorporated into the NBLAST and XBLAST programs of Altschul, et al., 1990, *J. Mol. Biol.* 215:403-410. BLAST nucleotide searches can be performed with the NBLAST program, score=100, wordlength=12 to obtain nucleotide sequences homologous to a nucleic acid encoding a protein of interest. BLAST protein searches can be performed with the XBLAST program, score=50, wordlength=3 to obtain amino acid sequences homologous to protein of interest. To obtain gapped alignments for comparison purposes, Gapped BLAST can be utilized as described in Altschul et al., 1997, *Nucleic Acids Res.* 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. (See, e.g., Internet web site address: www.ncbi.nlm.nih.gov.) Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM 120 weight residue table, a gap length penalty of 12, and a gap penalty of 4 can be used. Additional algorithms for sequence analysis are known in the art and include ADVANCE and ADAM as described in Torellis and Robotti, 1994, *Comput. Appl. Biosci.* 10:3-5; and FASTA described in Pearson and Lipman, 1988, *Proc. Natl. Acad. Sci.* 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. For a further description of FASTA parameters, see, e.g., bioweb.pasteur.fr/docs/man/man/fasta.1.html#sect2, the contents of which are incorporated herein by reference.

Alternatively, protein sequence alignment may be carried out using the CLUSTAL W algorithm, as described by Higgins et al., 1996, *Methods Enzymol.* 266:383-402.

As used herein, the terms "treatment" or "treat" refer to slowing, stopping, or reversing the progression of HL in a subject, as evidenced by a decrease or elimination of a clinical or diagnostic symptom of the disease. Treatment can include, for example, a decrease in the severity of a symptom, the number of symptoms, or frequency of relapse, e.g., the inhibition of tumor growth, the arrest of tumor growth, or the regression of already existing tumors.

The term "anti-cancer agent" as used herein, refers to any agent that slows, stops, or reverses the progression of cancer in a subject. For example, an anti-cancer agent is an agent that inhibits tumor growth, arrests tumor growth, and/or causes the regression of already existing tumors. Anti-inflammatory agents or other agents administered to a subject with cancer to treat symptoms associated with cancer, including, for example inflammation, weight loss, and general malaise are not considered anti-cancer agents.

The term "pharmaceutically acceptable" as used herein refers to those compounds, materials, compositions, and/or dosage forms that are, within the scope of sound medical judgment, suitable for contact with the tissues of human beings and animals without excessive toxicity, irritation, allergic response, or other problems or complications commensurate with a reasonable benefit/risk ratio. The term "pharmaceutically compatible ingredient" refers to a pharmaceutically acceptable diluent, adjuvant, excipient, or vehicle with which an antibody-drug conjugate compound is administered.

The term "therapeutically effective amount" as used herein to refer to combination therapy means the amount of the combination of agents taken together so that the combined effect elicits the desired biological or medicinal response, i.e., inhibits the occurrence or ameliorate one or more clinical or diagnostic symptoms of Hodgkin lymphoma. For example, the "therapeutically effective amount" as used herein to refer to combination therapy would be the amount of the antibody-drug conjugate compound and the amount of the chemotherapeutic drug(s) that when administered together, either sequentially or simultaneously, on the same or different days during a treatment cycle, have a combined effect that is therapeutically effective and synergistic. Further, it will be recognized by one skilled in the art that in the case of combination therapy with a therapeutically effective amount, as in the example above, the amount of the antibody-drug conjugate compound and/or the amount of the chemotherapeutic drug(s) individually may or may not be therapeutically effective.

The abbreviation "MMAE" refers to monomethyl auristatin E.

The abbreviation "MMAF" refers to dovaline-valine-dolaisoleunine-dolaproine-phenylalanine.

The abbreviations "fk" and "phe-lys" refer to the dipeptide phenylalanine-lysine.

The abbreviations "vc" and "val-cit" refer to the dipeptide valine-citrulline.

The term "compound" refers to and encompasses the chemical compound itself as well as, whether explicitly stated or not, and unless the context makes clear that the following are to be excluded: amorphous and crystalline forms of the compound, including polymorphic forms, where these forms may be part of a mixture or in isolation; free acid and free base forms of the compound, which are typically the forms shown in the structures provided herein; isomers of the compound, which refers to optical isomers, and tautomeric isomers, where optical isomers include enantiomers and diastereomers, chiral isomers and non-chiral isomers, and the optical isomers include isolated optical isomers as well as mixtures of optical isomers including racemic and non-racemic mixtures; where an isomer may be in isolated form or in a mixture with one or more other isomers; isotopes of the compound, including deuterium- and tritium-containing compounds, and including compounds containing radioisotopes, including therapeutically- and diagnostically-effective radioisotopes; multimeric forms of the compound, including dimeric, trimeric, etc. forms; salts of the compound, preferably pharmaceutically acceptable salts, including acid addition salts and base addition salts, including salts having organic counterions and inorganic counterions, and including zwitterionic forms, where if a compound is associated with two or more counterions, the two or more counterions may be the same or different; and solvates of the compound, including hemisolvates, monosolvates, disolvates, etc., including organic solvates and inorganic solvates, said inorganic solvates including hydrates; where if a compound is associated with two or more solvent molecules, the two or more solvent molecules may be the same or different. In some instances, reference made herein to a compound of the invention will include an explicit reference to one or of the above forms, e.g., salts and/or solvates, however, this reference is for emphasis only, and is not to be construed as excluding other of the above forms as identified above.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine Unless otherwise noted, the term "alkyl" refers to a saturated straight or branched hydrocarbon having from about 1 to about 20 carbon atoms (and all combinations and subcombinations of ranges and specific numbers of carbon atoms therein), with from about 1 to about 8 carbon atoms being preferred. Examples of alkyl groups are methyl, ethyl, n-propyl, iso-propyl, n-butyl, iso-butyl, sec-butyl, tert-butyl, n-pentyl, 2-pentyl, 3-pentyl, 2-methyl-2-butyl, n-hexyl, n-heptyl, n-octyl, n-nonyl, n-decyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

Alkyl groups, whether alone or as part of another group, can be optionally substituted with one or more groups, preferably 1 to 3 groups (and any additional substituents selected from halogen), including, but not limited to, -halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl, and wherein said —O—($C_1$-$C_8$ alkyl), —O—($C_2$-$C_8$ alkenyl), —O—($C_2$-$C_8$ alkynyl), -aryl, —$C_1$-$C_8$ alkyl, —$C_2$-$C_8$ alkenyl, and —$C_2$-$C_8$ alkynyl groups can be optionally further substituted with one or more groups including, but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R'', —OC(O)R'', —C(O)OR'', —C(O)NH$_2$, —C(O)NHR'', —C(O)N(R'')$_2$, —NHC(O)R'', —SR'', —SO$_3$R'', —S(O)$_2$R'', —S(O)R'', —OH, —N$_3$, —NH$_2$, —NH(R''), —N(R'')$_2$ and —CN, where each R'' is independently selected from —H, —$C_1$-$C_8$ alkyl, —$C_2$-$C_8$ alkenyl, —$C_2$-$C_8$ alkynyl, or -aryl.

Unless otherwise noted, the terms "alkenyl" and "alkynyl" refer to straight and branched carbon chains having from about 2 to about 20 carbon atoms (and all combinations and subcombinations of ranges and specific numbers of carbon atoms therein), with from about 2 to about 8 carbon atoms being preferred. An alkenyl chain has at least one double bond in the chain and an alkynyl chain has at least one triple bond in the chain. Examples of alkenyl groups include, but are not limited to, ethylene or vinyl, allyl, -1-butenyl, -2-butenyl, -isobutylenyl, -1-pentenyl, -2-pentenyl, -3-methyl-1-butenyl, -2-methyl-2-butenyl, and -2,3-dimethyl-2-butenyl. Examples of alkynyl groups include, but are not limited to, acetylenic, propargyl, acetylenyl, propynyl, -1-butynyl, -2-butynyl, -1-pentynyl, -2-pentynyl, and -3-methyl-1 butynyl.

Alkenyl and alkynyl groups, whether alone or as part of another group, can be optionally substituted with one or more groups, preferably 1 to 3 groups (and any additional substituents selected from halogen), including but not limited to, -halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl and wherein said —O—($C_1$-$C_8$ alkyl), —O—($C_2$-$C_8$ alkenyl), —O—($C_2$-$C_8$ alkynyl), -aryl, —$C_1$-$C_8$ alkyl, —$C_2$-$C_8$ alkenyl, and —$C_2$-$C_8$ alkynyl groups can be optionally further substituted with one or more substituents including, but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$$C_8$ alkynyl), -aryl, —C(O)R'', —OC(O)R'', —C(O)OR'', —C(O)NH$_2$, —C(O)NHR'', —C(O)N(R'')$_2$, —NHC(O)R'', —SR'', —SO$_3$R'', —S(O)$_2$R'', —S(O)R'', —OH, —N$_3$, —NH$_2$, —NH(R''), —N(R'')$_2$ and —CN, where each R'' is independently selected from —H, —$C_1$-$C_8$ alkyl, —$C_2$-$C_8$ alkenyl, —$C_2$-$C_8$ alkynyl, or -aryl.

Unless otherwise noted, the term "alkylene" refers to a saturated branched or straight chain hydrocarbon radical having from about 1 to about 20 carbon atoms (and all combinations and subcombinations of ranges and specific numbers of carbon atoms therein), with from about 1 to about 8 carbon atoms being preferred and having two monovalent radical centers derived by the removal of two hydrogen atoms from the same or two different carbon atoms of a parent alkane. Typical alkylenes include, but are not limited to, methylene, ethylene, propylene, butylene, pentylene, hexylene, heptylene, ocytylene, nonylene, decalene, 1,4-cyclohexylene, and the like. Alkylene groups, whether alone or as part of another group, can be optionally substituted with one or more groups, preferably 1 to 3 groups (and any additional substituents selected from halogen), including, but not limited to, -halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH₂, —NH(R'), —N(R')₂ and —CN, where each R' is independently selected from —H, —C₁-C₈ alkyl, —C₂-C₈ alkenyl, —C₂-C₈ alkynyl, or -aryl and wherein said —O—(C₁-C₈ alkyl), —O—(C₂-C₈ alkenyl), —O—(C₂-C₈ alkynyl), -aryl, —C₁-C₈ alkyl, —C₂-C₈ alkenyl, and —C₂-C₈ alkynyl groups can be further optionally substituted with one or more substituents including, but not limited to, —C₁-C₈ alkyl, —C₂-C₈ alkenyl, —C₂-C₈ alkynyl, -halogen, —O—(C₁-C₈ alkyl), —O—(C₂-C₈ alkenyl), —O—(C₂-C₈ alkynyl), -aryl, —C(O)R", —OC(O)R", —C(O)OR", —C(O)NH₂, —C(O)NHR", —C(O)N(R")₂, —NHC(O)R", —SR", —SO₃R", —S(O)₂R", —S(O)R", —OH, —N₃, —NH₂, —NH(R"), —N(R")₂ and —CN, where each R" is independently selected from —H, —C₁-C₈ alkyl, —C₂-C₈ alkenyl, —C₂-C₈ alkynyl, or -aryl.

Unless otherwise noted, the term "alkenylene" refers to an optionally substituted alkylene group containing at least one carbon-carbon double bond. Exemplary alkenylene groups include, for example, ethenylene (—CH═CH—) and propenylene (—CH═CHCH₂—).

Unless otherwise noted, the term "alkynylene" refers to an optionally substituted alkylene group containing at least one carbon-carbon triple bond. Exemplary alkynylene groups include, for example, acetylene (—C≡C—), propargyl (—CH₂C≡C—), and 4-pentynyl (—CH₂CH₂CH₂C≡CH—).

Unless otherwise noted, the term "aryl" refers to a monovalent aromatic hydrocarbon radical of 6-20 carbon atoms (and all combinations and subcombinations of ranges and specific numbers of carbon atoms therein) derived by the removal of one hydrogen atom from a single carbon atom of a parent aromatic ring system. Some aryl groups are represented in the exemplary structures as "Ar". Typical aryl groups include, but are not limited to, radicals derived from benzene, substituted benzene, phenyl, naphthalene, anthracene, biphenyl, and the like.

An aryl group, whether alone or as part of another group, can be optionally substituted with one or more, preferably 1 to 5, or even 1 to 2 groups including, but not limited to, -halogen, —C₁-C₈ alkyl, —C₂-C₈ alkenyl, —C₂-C₈ alkynyl, —O—(C₁-C₈ alkyl), —O—(C₂-C₈ alkenyl), —O—(C₂-C₈ alkynyl), -aryl, —C(O)R', —OC(O)R', —C(O)OR', —C(O)NH₂, —C(O)NHR', —C(O)N(R')₂, —NHC(O)R', —SR', —SO₃R', —S(O)₂R', —S(O)R', —OH, —NO₂, —N₃, —NH₂, —NH(R'), —N(R')₂ and —CN, where each R' is independently selected from —H, —C₁-C₈ alkyl, —C₂-C₈ alkenyl, —C₂-C₈ alkynyl, or -aryl and wherein said —C₁-C₈ alkyl, —C₂-C₈ alkenyl, —C₂-C₈ alkynyl, O—(C₁-C₈ alkyl), —O—(C₂-C₈ alkenyl), —O—(C₂-C₈ alkynyl), and -aryl groups can be further optionally substituted with one or more substituents including, but not limited to, —C₁-C₈ alkyl, —C₂-C₈ alkenyl, —C₂-C₈ alkynyl, -halogen, —O—(C₁-C₈ alkyl), —O—(C₂-C₈ alkenyl), —O—(C₂-C₈ alkynyl), -aryl, —C(O)R", —OC(O)R", —C(O)OR", —C(O)NH₂, —C(O)NHR", —C(O)N(R")₂, —NHC(O)R", —SR", —SO₃R", —S(O)₂R", —S(O)R", —OH, —N₃, —NH₂, —NH(R"), —N(R")₂ and —CN, where each R" is independently selected from —H, —C₁-C₈ alkyl, —C₂-C₈ alkenyl, —C₂-C₈ alkynyl, or -aryl.

Unless otherwise noted, the term "arylene" refers to an optionally substituted aryl group which is divalent (i.e., derived by the removal of two hydrogen atoms from the same or two different carbon atoms of a parent aromatic ring system) and can be in the ortho, meta, or para configurations as shown in the following structures with phenyl as the exemplary aryl group:

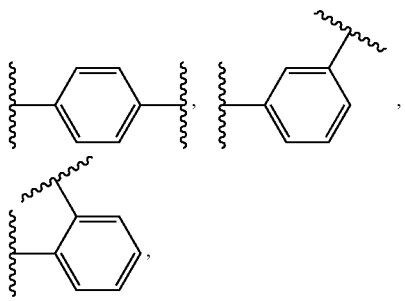

Typical "—(C₁-C₈ alkylene)aryl," "—(C₂-C₈ alkenylene)aryl", and "—(C₂-C₈ alkynylene)aryl" groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like.

Unless otherwise noted, the term "heterocycle," refers to a monocyclic, bicyclic, or polycyclic ring system having from 3 to 14 ring atoms (also referred to as ring members) wherein at least one ring atom in at least one ring is a heteroatom selected from N, O, P, or S (and all combinations and subcombinations of ranges and specific numbers of carbon atoms and heteroatoms therein). The heterocycle can have from 1 to 4 ring heteroatoms independently selected from N, O, P, or S. One or more N, C, or S atoms in a heterocycle can be oxidized. A monocylic heterocycle preferably has 3 to 7 ring members (e.g., 2 to 6 carbon atoms and 1 to 3 heteroatoms independently selected from N, O, P, or S), and a bicyclic heterocycle preferably has 5 to 10 ring members (e.g., 4 to 9 carbon atoms and 1 to 3 heteroatoms independently selected from N, O, P, or S). The ring that includes the heteroatom can be aromatic or non-aromatic. Unless otherwise noted, the heterocycle is attached to its pendant group at any heteroatom or carbon atom that results in a stable structure.

Heterocycles are described in Paquette, "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* 82:5566 (1960).

Unless otherwise noted, the term "heterocyclo" refers to an optionally substituted heterocycle group as defined above that is divalent (i.e., derived by the removal of two hydrogen atoms from the same or two different carbon atoms of a parent heterocyclic ring system).

Examples of "heterocycle" groups include by way of example and not limitation pyridyl, dihydropyridyl, tetrahydropyridyl (piperidyl), thiazolyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4H-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl. Preferred "heterocycle" groups include, but are not limited to, benzofuranyl, benzothiophenyl, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl.

A heterocycle group, whether alone or as part of another group, can be optionally substituted with one or more groups, preferably 1 to 2 groups, including but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, —N$_3$, —NH$_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl and wherein said —O—($C_1$-$C_8$ alkyl), —O—($C_2$-$C_8$ alkenyl), —O—($C_2$-$C_8$ alkynyl), —$C_1$-$C_8$ alkyl, —$C_2$-$C_8$ alkenyl, —$C_2$-$C_8$ alkynyl, and -aryl groups can be further optionally substituted with one or more sub-stituents including, but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —$C_1$-$C_8$ alkyl, —$C_2$-$C_8$ alkenyl, —$C_2$-$C_8$ alkynyl, or aryl.

By way of example and not limitation, carbon-bonded heterocycles can be bonded at the following positions: position 2, 3, 4, 5, or 6 of a pyridine; position 3, 4, 5, or 6 of a pyridazine; position 2, 4, 5, or 6 of a pyrimidine; position 2, 3, 5, or 6 of a pyrazine; position 2, 3, 4, or 5 of a furan, tetrahydrofuran, thiofuran, thiophene, pyrrole or tetrahydropyrrole; position 2, 4, or 5 of an oxazole, imidazole or thiazole; position 3, 4, or 5 of an isoxazole, pyrazole, or isothiazole; position 2 or 3 of an aziridine; position 2, 3, or 4 of an azetidine; position 2, 3, 4, 5, 6, 7, or 8 of a quinoline; or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, or 1H-indazole; position 2 of a isoindole, or isoindoline; position 4 of a morpholine; and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

Unless otherwise noted, the term "carbocycle," refers to a saturated or unsaturated non-aromatic monocyclic, bicyclic, or polycyclic ring system having from 3 to 14 ring atoms (and all combinations and subcombinations of ranges and specific numbers of carbon atoms therein) wherein all of the ring atoms are carbon atoms. Monocyclic carbocycles preferably have 3 to 6 ring atoms, still more preferably 5 or 6 ring atoms. Bicyclic carbocycles preferably have 7 to 12 ring atoms, e.g., arranged as a bicyclo [4,5], [5,5], [5,6] or [6,6] system, or 9 or 10 ring atoms arranged as a bicyclo[5,6] or [6,6] system. The term "carbocycle" includes, for example, a monocyclic carbocycle ring fused to an aryl ring (e.g., a monocyclic carbocycle ring fused to a benzene ring). Carbocycles preferably have 3 to 8 carbon ring atoms.

Carbocycle groups, whether alone or as part of another group, can be optionally substituted with, for example, one or more groups, preferably 1 or 2 groups (and any additional substituents selected from halogen), including, but not limited to, -halogen, —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl and wherein said —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), and -aryl groups can be further optionally substituted with one or more substituents including, but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —$C_1$-$C_8$ alkyl, —$C_2$-$C_8$ alkenyl, —$C_2$-$C_8$ alkynyl, or -aryl.

Examples of monocyclic carbocyclic substituents include -cyclopropyl, -cyclobutyl, -cyclopentyl, -1-cyclopent-1-enyl, -1-cyclopent-2-enyl, -1-cyclopent-3-enyl, cyclohexyl, -1-cyclohex-1-enyl, -1-cyclohex-2-enyl, -1-cyclohex-3-enyl, -cycloheptyl, -cyclooctyl-1,3-cyclohexadienyl, -1,4-cyclohexadienyl, -1,3-cycloheptadienyl, -1,3,5-cycloheptatrienyl, and -cyclooctadienyl.

A "carbocyclo," whether used alone or as part of another group, refers to an optionally substituted carbocycle group as defined above that is divalent (i.e., derived by the removal of two hydrogen atoms from the same or two different carbon atoms of a parent carbocyclic ring system).

When any variable occurs more than one time in any constituent or in any formula, its definition in each occurrence is independent of its definition at every other. Combinations of substituents and/or variables are permissible only if such combinations result in stable compounds.

Unless otherwise indicated by context, a hyphen (-) designates the point of attachment to the pendant molecule. Accordingly, the term "—($C_1$-$C_8$ alkylene)aryl" or "—$C_1$-$C_8$ alkylene(aryl)" refers to a $C_1$-$C_8$ alkylene radical as defined herein wherein the alkylene radical is attached to the pendant molecule at any of the carbon atoms of the alkylene radical and one of the hydrogen atoms bonded to a carbon atom of the alkylene radical is replaced with an aryl radical as defined herein.

When a particular group is "substituted", that group may have one or more substituents, preferably from one to five substituents, more preferably from one to three substituents, most preferably from one to two substituents, independently selected from the list of substituents. The group can, however, generally have any number of substituents selected from halogen. Groups that are substituted are so indicated.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Protective groups as used herein refer to groups which selectively block, either temporarily or permanently, one reactive site in a multifunctional compound. Suitable hydroxy-protecting groups for use in the present invention are pharmaceutically acceptable and may or may not need to be cleaved from the parent compound after administration to a subject in order for the compound to be active. Cleavage is through normal metabolic processes within the body. Hydroxy protecting groups are well known in the art, see, Protective Groups in Organic Synthesis by T. W. Greene and P. G. M. Wuts (John Wiley & sons, $3^{rd}$ Edition) incorporated herein by reference in its entirety and for all purposes and include, for example, ether (e.g., alkyl ethers and silyl ethers including, for example, dialkylsilylether, trialkylsilylether, dialkylalkoxysilylether), ester, carbonate, carbamates, sulfonate, and phosphate protecting groups. Examples of hydroxy protecting groups include, but are not limited to, methyl ether; methoxymethyl ether, methylthiomethyl ether, (phenyldimethylsilyl)methoxymethyl ether, benzyloxymethyl ether, p-methoxybenzyloxymethyl ether, p-nitrobenzyloxymethyl ether, o-nitrobenzyloxymethyl ether, (4-methoxyphenoxy)methyl ether, guaiacolmethyl ether, t-butoxymethyl ether, 4-pentenyloxymethyl ether, siloxymethyl ether, 2-methoxyethoxymethyl ether, 2,2,2-trichloroethoxymethyl ether, bis(2-chloroethoxy)methyl ether, 2-(trimethylsilyl)ethoxymethyl ether, menthoxymethyl ether, tetrahydropyranyl ether, 1-methoxycylcohexyl ether, 4-methoxytetrahydrothiopyranyl ether, 4-methoxytetrahydrothiopyranyl ether S,S-Dioxide, 1-[(2-choro-4-methyl) phenyl]-4-methoxypiperidin-4-yl ether, 1-(2-fluorophenyl)-4-methoxypiperidin-4-yl ether, 1,4-dioxan-2-yl ether, tetrahydrofuranyl ether, tetrahydrothiofuranyl ether; substituted ethyl ethers such as 1-ethoxyethyl ether, 1-(2-chloroethoxy)ethyl ether, 1-[2-(trimethylsilyl)ethoxy]ethyl ether, 1-methyl-1-methoxyethyl ether, 1-methyl-1-benzyloxyethyl ether, 1-methyl-1-benzyloxy-2-fluoroethyl ether, 1-methyl-1phenoxyethyl ether, 2-trimethylsilyl ether, t-butyl ether, allyl ether, propargyl ethers, p-chlorophenyl ether, p-methoxyphenyl ether, benzyl ether, p-methoxybenzyl ether 3,4-dimethoxybenzyl ether, trimethylsilyl ether, triethylsilyl ether, tripropylsilylether, dimethylisopropylsilyl ether, diethylisopropylsilyl ether, dimethylhexylsilyl ether, t-butyldimethylsilyl ether, diphenylmethylsilyl ether, benzoylformate ester, acetate ester, chloroacetate ester, dichloroacetate ester, trichloroacetate ester, trifluoroacetate ester, methoxyacetate ester, triphenylmethoxyacetate ester, phenylacetate ester, benzoate ester, alkyl methyl carbonate, alkyl 9-fluorenylmethyl carbonate, alkyl ethyl carbonate, alkyl 2,2,2-trichloroethyl carbonate, 1,1-dimethyl-2,2,2-trichloroethyl carbonate, alkylsulfonate, methanesulfonate, benzylsulfonate, tosylate, methylene acetal, ethylidene acetal, and t-butylmethylidene ketal. Preferred protecting groups are represented by the formulas —$R^a$, —Si($R^a$)($R^a$)($R^a$), —C(O)$R^a$, —C(O)O$R^a$, —C(O)NH($R^a$), —S(O)$_2R^a$, —S(O)$_2$OH, P(O)(OH)$_2$, and —P(O)(OH)O$R^a$, wherein $R^a$ is $C_1$-$C_{20}$ alkyl, $C_2$-$C_{20}$ alkenyl, $C_2$-$C_{20}$ alkynyl, —$C_1$-$C_{20}$ alkylene(carbocycle), —$C_2$-$C_{20}$ alkenylene(carbocycle), —$C_2$-$C_{20}$ alkynylene(carbocycle), —$C_6$-$C_{10}$ aryl, —$C_1$-$C_{20}$ alkylene(aryl), —$C_2$-$C_{20}$ alkenylene(aryl), —$C_2$-$C_{20}$ alkynylene(aryl), —$C_1$-$C_{20}$ alkylene(heterocycle), —$C_2$-$C_{20}$ alkenylene(heterocycle), or —$C_2$-$C_{20}$ alkynylene(heterocycle) wherein said alkyl, alkenyl, alkynyl, alkylene, alkenylene, and alkynylene radicals whether alone or as part of another group are optionally substituted with one or more groups independently selected from A1, said carbocycle radicals whether alone or as part of another group are optionally substituted with one or more groups independently selected from A2, said aryl radicals whether alone or as part of another group are optionally substituted with one or more groups independently selected from A3, and said heterocycle radicals whether alone or as part of another group are optionally substituted with one or more groups independently selected from A4. A1, A2, A3, and A4 are as defined herein.

D. The Antibody-Drug Conjugate

The methods described herein encompass the use of an antibody-drug conjugate compound in combination therapy for the treatment of HL. The antibody-drug conjugate compound for use in the present invention comprises an anti-CD30 antibody, i.e., an antibody that specifically binds to CD30, linked to a drug moiety. The drug moiety is of the auristatin type which have been shown to interfere with microtubule dynamics and nuclear and cellular division and have anticancer activity. Auristatins of the present invention bind to tubulin and exert a cytotoxic or cytostatic effect on a HL cell line, e.g., L540cy cell line. In some embodiments of the present invention, the auristatin drug is conjugated to the anti-CD30 antibody via a linker that is cleavable under intracellular conditions, such that cleavage of the linker releases the auristatin compound from the antibody in the intracellular environment. In yet other embodiments, the linker unit is not cleavable and the drug is released by antibody degradation.

There are a number of different assays that can be used for determining whether an auristatin or resultant antibody-drug conjugate exerts a cytostatic or cytotoxic effect on a HL cell line. In one example for determining whether an auristatin or resultant antibody-drug conjugate exerts a cytostatic or cytotoxic effect on a HL cell line, a thymidine incorporation assay is used. For example, HL cells at a density of 5,000 cells/well of a 96-well plated is cultured for a 72-hour period and exposed to 0.5 µCi of $^3$H-thymidine during the final 8 hours of the 72-hour period, and the incorporation of $^3$H-thymidine into cells of the culture is measured in the presence and absence of the auristatin or antibody drug conjugate. The auristatin or resultant antibody-drug conjugate has a cytostatic or cytotoxic effect on the HL cell line if the cells of the culture have reduced $^3$H-thymidine incorporation compared to cells of the same cell line cultured under the same conditions but not contacted with the auristatin or antibody drug conjugate.

For determining cytotoxicity, necrosis or apoptosis (programmed cell death) can be measured. Necrosis is typically accompanied by increased permeability of the plasma membrane; swelling of the cell, and rupture of the plasma membrane. Apoptosis is typically characterized by membrane blebbing, condensation of cytoplasm, and the activation of endogenous endonucleases. Determination of any of these effects on HL cells indicates that an auristatin or antibody-drug conjugate is useful in the treatment or prevention of HL.

In another example, for determining whether an auristatin or resultant antibody-drug conjugate exerts a cytostatic or cytotoxic effect on a HL cell line, cell viability is measured by determining in a cell the uptake of a dye such as neutral red, trypan blue, or ALAMAR™ blue (see, e.g., Page et al., 1993, *Intl. J. of Oncology* 3:473-476). In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytoxicity (Skehan et al., 1990, *J. Nat'l Cancer Inst.* 82:1107-12). Preferred antibody drug conjugates include those with an $IC_{50}$ value (defined as the mAB concentration that gives 50% cell kill) of less than 1000 ng/ml, preferably less than 500 ng/ml, more preferably less than 100 ng/ml, even most preferably less than 50 or even less than 10 ng/ml on a Hodgkin lymphoma cell line, e.g., L540cy cell line.

Methods for determining whether a compound binds tubulin are known in the art. See, for example, Muller et al., *Anal. Chem.* 2006, 78, 4390-4397; Hamel et al., *Molecular Pharmacology*, 1995 47: 965-976; and Hamel et al., *The Journal of Biological Chemistry*, 1990 265:28, 17141-17149. For purposes of the present invention, the relative affinity of a compound to tubulin can be determined. Preferred auristatins of the present invention bind tubulin with an affinity ranging from 10 fold lower (weaker affinity) that the binding affinity of MMAE to tubulin to 10 fold, 20 fold or even 100 fold higher (tighter affinity) than the binding affinity of MMAE to tubulin.

E. Gemcitabine

Some methods of the present invention encompass administering the antibody-drug conjugate compound and gemcitabine for the treatment of Hodgkin lymphoma.

Gemcitabine, 4-amino-1-[(2R,4R,5R)-3,3-difluoro-4-hydroxy-5-(hydroxymethyl)oxolan-2-yl]pyrimidin-2-one, is currently marketed under the label GEMZAR™ by Eli Lilly and Company. Gemcitabine, an analog of cytarabine, is a pyrimidine antimetabolite that has been found to demonstrate a broad spectrum of activity in HL.

The present invention encompasses combination therapy with an antibody-drug conjugate compound, gemcitabine and optionally one or more additional agents, e.g., anti-cancer agents, including chemotherapeutic agents. For example, one or more of vinorelbine, dexamethasone, cisplatin, and doxorubicin, including pegylated liposomal doxorubicin, can be administered as part of the combination therapy (e.g., GVD regimen). In some embodiments, however, gemcitabine will be the only chemotherapeutic agent administered as part of the combination therapy with the antibody-drug conjugate compound. For example, in some embodiments, during one or more cycles of therapy, gemcitabine will be the only chemotherapeutic agent administered as part of the combination therapy with the antibody-drug conjugate compound. In some embodiments, gemcitabine will be the only anti-cancer agent administered as part of the combination therapy with the antibody-drug conjugate compound. In certain embodiments, doxorubicin, or, more specifically, pegylated liposomal doxorubicin, will be specifically excluded from the combination therapy. In some embodiments, vinorelbine and doxorubicin, or vinorelbine and pegylated liposomal doxorubicin, will be excluded from the combination therapy.

F. Doxorubicin, Bleomycin, Vinblastine, and Dacarbazine Therapy

The methods of the present invention encompass administering an antibody-drug conjugate compound and a chemotherapeutic regimen of doxorubicin, bleomycin, vinblastine, and dacarbazin as combination therapy for the treatment of Hodgkin lymphoma. Currently doxorubicin, bleomycin, vinblastine, and dacarbazin are administered together in a chemotherapeutic regimen referred to as ABVD.

The ABVD chemotherapy regimen is currently considered the standard of care in the $1^{st}$ line treatment of HL. The ABVD chemotherapeutic regimen is typically administered to patients every two weeks in a four week treatment cycle. Typically, at day 1 and 15 of the four week interval, patients are treated with 25 mg/m$^2$ doxorubicin, 10 U/m$^2$ bleomycin, 6 mg/m$^2$ vinblastine, and 375 mg/m$^2$ dacarbazine.

The present invention encompasses combination therapy with an antibody-drug conjugate compound, doxorubicin, bleomycin, vinblastine, and dacarbazin (e.g., ABVD regimen) and optionally one or more additional agents, e.g., anti-cancer agents, including chemotherapeutic agents. In certain embodiments, however, doxorubicin, bleomycin, vinblastine, and dacarbazin will be the only chemotherapeutic agents administered as part of the combination therapy with the antibody-drug conjugate compound. For example, in some embodiments, during one or more cycles of therapy, the ABVD regimen will be the only chemotherapeutic regimen administered as part of the combination therapy with the antibody-drug conjugate compound. In some embodiments, the ABVD regimen will be the only anti-cancer regimen administered as part of the combination therapy with the antibody-drug conjugate compound. In certain embodiments, doxorubicin will be specifically excluded from the combination therapy and the chemotherapeutic agents will comprise bleomycin, vinblastine, and dacarbazin.

G. Synergism

In preferred embodiments of the present invention, therapy with the antibody-drug conjugate compound and the chemotherapeutic drug(s) provides a synergistic effect in the treatment of Hodgkin lymphoma in the patient As used herein, the term "synergy" or "synergistic effect" when used in connection with a description of the efficacy of a combination of agents, means any measured effect of the combination which is greater than the effect predicted from a sum of the effects of the individual agents. Accordingly, the present invention encompasses embodiments wherein subjects treated with both the antibody-drug conjugate compound and the chemotherapeutic drug(s) have significantly better treatment outcomes than subjects treated with only the antibody-drug conjugate compound or only the chemotherapeutic drug(s) given the same administration and dosage regimens. The present invention encompasses embodiments wherein subjects have better treatment outcomes than would be expected from the sum of effects of treatment with the antibody-drug conjugate compound alone and the chemotherapeutic regimen alone given the same administration and dosage regimens.

Methods of determining such synergy are known in the art. In one example, syngeneic (same gene line) tumors are harvested from donor animals, disaggregated, counted and then injected back into syngeneic (same strain) host mice. Anti-cancer combinations are typically then injected at some later time point(s), either by intraperitoneal, intravenous or administered by the oral routes, and tumor growth rates and/or survival are determined, compared to untreated controls and controls exposed only to one of the therapies. Growth rates are typically measured for tumors growing in the front flank of the animal, wherein perpendicular diameters of tumor width are translated into an estimate of total tumor mass or volume. The time to reach a predetermined mass (e.g., time for tumor to triplicate or time for tumor to quadruple) is then compared to the time required for equal tumor growth in the control animals. If the time to reach the predetermined mass for the animal treated with the combination therapy is greater than the value obtained from adding the time to reach the predetermined mass for the animal treated with therapy "A" and the animal treated with therapy "B" (i.e., each therapy alone), the combination therapy can be said to provide a synergistic effect. In another example, the time to reach the predetermined mass for the animal treated with the combination therapy might not be greater than the value obtained from adding the time to reach the predetermined mass for the animal treated with therapy "A" and the animal treated with therapy "B"; however, another measured effect of the combination which is greater than that predicted from a sum of the effects of the individual agents is sufficient to identify/determine the combination therapy as synergistic. For example, if the number of durable responses for the animals treated with the combination therapy is greater than the sum of the number of durable responses in each treatment arm alone, the combined therapy provides a synergistic effect. A durable response (DR) is defined as the absence of palpable tumor in the animal.

H. Administration

The antibody-drug conjugate and gemcitabine or the antibody-drug conjugate and the ABVD regimen are administered in such a way that they provide a synergistic effect in the treatment of HL in a patient. Administration can be by any suitable means provided that the administration provides the desired therapeutic effect, i.e., synergism. In preferred embodiments, the antibody-drug conjugate compound and gemcitabine or the antibody-drug conjugate compound and the ABVD regimen are administered during the same cycle of therapy, e.g., during one cycle of therapy, e.g., a three or four week time period, both the antibody-drug conjugate compound and the specified chemotherapeutic drug(s) are administered to the subject. In some embodiments of the present invention, administration of the antibody-drug conjugate compound will be at such a time that it sensitizes cancerous cells to treatment with gemcitabine or the ABVD regimen, i.e., sequentially, e.g., immediately prior to chemotherapeutic treatment, e.g., less than 2 hours prior to chemotherapeutic treatment.

The dosage of the antibody-drug conjugate compound administered to a patient with HL will also depend on frequency of administration. The present invention contemplates antibody-drug conjugate compound delivery once during the treatment cycle or by a split delivery.

The present invention encompasses embodiments wherein the antibody-drug conjugate compound will be administered in a dose range of 0.1 mg/kg to 2.7 mg/kg of the subject's body weight per dose, 0.2 mg/kg to 1.8 mg/kg of the subject's body weight per dose, 0.2 mg/kg to 1.2 mg/kg of the subject's body weight per dose, 0.4 mg/kg to 1 mg/kg of the subject's body weight per dose, 1.0 mg/kg to 1.5 mg/kg of the subject's body weight per dose, and 0.5 mg/kg to 1 mg/kg of the subject's body weight per dose. Other ranges are encompassed by the present invention as long as they produce the desired result.

The present invention encompasses treatment schedules wherein the total dosage of the antibody-drug conjugate compound, administered to a patient with HL will be, for example, 0.1 mg/kg to 5 mg/kg, 0.1 mg/kg to 4 mg/kg, 0.1 mg/kg to 3.2 mg/kg, or 0.1 mg/kg to 2.7 mg/kg of the subject's body weight over a treatment cycle, e.g., a 3 or 4 week time period. In some embodiments, the total dosage of the antibody-drug conjugate compound administered to a patient with HL will be, for example about 0.6 mg/kg to about 5 mg/kg, about 0.6 mg/kg to about 4 mg/kg, about 0.6 mg/kg to about 3.2 mg/kg, about 0.6 mg/kg to about 2.7 mg/kg, or even about 1.5 mg/kg to about 3 mg/kg over a treatment cycle, e.g., a 3 or 4 week time period. In some embodiments, the dosage will be about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, about 3 mg/kg, about 3.1 mg/kg, about 3.2 mg/kg, about 3.3 mg/kg, about 3.4 mg/kg, about 3.5 mg/kg, about 3.6 mg/kg, about 3.7 mg/kg, or about 3.8 mg/kg of the subject's body weight over the treatment cycle, e.g., a 3 or 4 week time period. The present invention contemplates administration of the drug for one or more treatment cycles, for example, 1, 2, 3, 4, 5, 6, or more, treatment cycles. In some embodiments, there will be periods of rest between one or more of the treatment cycles. For example, in some embodiments, there will be a period of rest between the second and third treatment cycle but not the first and second treatment cycle. In another embodiment, there might be a period of rest between the first and second treatment cycle but not the second and third treatment cycle. Dosing schedules include, for example, administering the antibody drug conjugate compound once during a treatment schedule, e.g., on day 1 of a 21 day cycle, twice during a treatment cycle, e.g., on days 1 and 15 of a 28 day cycle, and three times during a treatment cycle, e.g., on days 1, 8 and 15 of a 28 day cycle. Other dosage schedules are encompassed by the present invention.

The present invention encompasses treatment schedules wherein the antibody-drug conjugate compound is administered once during a treatment cycle, e.g., a 3 or 4 week time period. For example, in some embodiments, the antibody-drug conjugate will be administered on the third week of a 3 or 4 week treatment cycle, e.g., on day 21 of a three or four week cycle. In some embodiments, the antibody-drug conjugate will be administered on day 1 of a 3 or 4 week treatment cycle, or on any other day of a three or four week treatment cycle. In some such embodiments, the dosage of the antibody-drug conjugate compound administered to a patient with HL will typically be, for example, 0.1 mg/kg to 5 mg/kg of the subject's body weight over the treatment cycle, e.g., a 3 or 4 week time period. More typically, the dosage will be 0.1 mg/kg to 4 mg/kg, 0.1 mg/kg to 3.2 mg/kg, 0.1 mg/kg to 2.7 mg/kg, 1 mg/kg to 2.7 mg/kg, 1.5 mg/kg to 2.7 mg/kg, or 1.5 mg/kg to 2 mg/kg of the subject's body weight over the treatment cycle, e.g., a 3 or 4 week time period. In some embodiments, the total dosage of the antibody-drug conjugate compound administered to a patient with HL will be, for example about 0.6 mg/kg to about 5 mg/kg, about 0.6 mg/kg to about 4 mg/kg, about 0.6 mg/kg to about 3.2 mg/kg, about 0.6 mg/kg to about 2.7 mg/kg, or even about 1.5 mg/kg to about 3 mg/kg over a treatment cycle, e.g., a 3 or 4 week time period. In some embodiments, the dosage will be about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, about 3 mg/kg, about 3.1 mg/kg, about 3.2 mg/kg, about 3.3 mg/kg, about 3.4 mg/kg, about 3.5 mg/kg, about 3.6 mg/kg, about 3.7 mg/kg, or about 3.8 mg/kg of the subject's body weight over the treatment cycle.

In other embodiments the antibody-drug conjugate compound will be administered more than once during a treatment cycle. For example, in some embodiments, the antibody-drug conjugate compound will be administered weekly for three consecutive weeks in a three or four week treatment cycle. For example, in some embodiments, the antibody-drug conjugate compound will be administered on days 1, 8, and 15 of each 28 day treatment cycle. In some such embodiments, the dosage of the antibody-drug conjugate compound administered to a patient with HL can be, for example, 0.1 mg/kg to 5 mg/kg, 0.1 mg/kg to 4 mg/kg, 0.1 mg/kg to 3.2 mg/kg, or 0.1 mg/kg to 2.7 mg/kg of the subject's body weight over the treatment cycle. In some embodiments, the total dosage of the antibody-drug conjugate compound administered to a patient with HL will be, for example about 0.6 mg/kg to about 5 mg/kg, about 0.6 mg/kg to about 4 mg/kg, about 0.6 mg/kg to about 3.2 mg/kg, about 0.6 mg/kg to about 2.7 mg/kg, or even about 1.5 mg/kg to about 3 mg/kg over the treatment cycle. In some embodiments, the dosage will be about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, about 3 mg/kg, about 3.1 mg/kg, about 3.2 mg/kg, about 3.3 mg/kg, about 3.4 mg/kg, about 3.5 mg/kg, about 3.6 mg/kg, about 3.7 mg/kg, about 3.8 mg/kg, about 3.9 mg/kg or about 4.0 mg/kg of the subject's body weight over the treatment cycle. In some embodiments, the dosage will generally be 0.1 to 5 mg/kg of the subject's body weight, 0.1 mg/kg to 3.2 mg/kg of the subject's body weight, even more typically, 0.1 mg/kg to 2.7 mg/kg, 0.2 mg/kg to 1.8 mg/kg, 0.2 mg/kg to 1.2 mg/kg, 0.2 mg/kg to 1 mg/kg, 0.4 mg/kg to 1 mg/kg, or 0.4 mg/kg to 0.8 mg/kg of the subject's body weight on days 1, 8, and 15 of each 28 day cycle. In some embodiments, the dosage will be about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg/about 1.4 mg/kg, or about 1.5 mg/kg of the subject's body weight on days 1, 8, and 15 of each 28 day cycle.

In even other embodiments the antibody-drug conjugate compound will be administered every two weeks in a four week treatment cycle. For example, in some embodiments, the antibody-drug conjugate compound will be administered on days 1 and 15 of each 28 day treatment cycle. In some such embodiments, the dosage of the antibody-drug conjugate compound administered to a patient with HL can be, for example, 0.1 mg/kg to 5 mg/kg, 0.1 mg/kg to 4 mg/kg, 0.1 mg/kg to 3.2 mg/kg, or 0.1 mg/kg to 2.7 mg/kg of the subject's body weight over the treatment cycle. In some embodiments, the total dosage of the antibody-drug conjugate compound administered to a patient with HL will be, for example about 0.6 mg/kg to about 5 mg/kg, about 0.6 mg/kg to about 4 mg/kg, about 0.6 mg/kg to about 3.2 mg/kg, about 0.6 mg/kg to about 2.7 mg/kg, or even about 1.5 mg/kg to about 3 mg/kg over the treatment cycle. In some embodiments, the dosage will be about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, about 3 mg/kg, about 3.1 mg/kg, about 3.2 mg/kg, about 3.3 mg/kg, about 3.4 mg/kg, about 3.5 mg/kg, about 3.6 mg/kg, about 3.7 mg/kg, or about 3.8 mg/kg of the subject's body weight over the treatment cycle. In some embodiments, the dosage of the antibody-drug conjugate compound will generally be 0.1 mg/kg to 5 mg/kg of the subject's body weight, 0.1 mg/kg to 3.2 mg/kg of the subject's body weight, more typically 0.1 mg/kg to 2.7 mg/kg, even more typically 0.2 mg/kg to 1.8 mg/kg, 0.2 mg/kg to 1.2 mg/kg, 0.2 mg/kg to 1.5 mg/kg, 1 mg/kg to 1.5 mg/kg, or 0.5 to 1.2 mg/kg, of the subject's body weight on days 1 and 15 of each 28 day cycle. In some embodiments, the dosage will be about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, or about 1.8 mg/kg of the subject's body weight on days 1 and 15 of each 28 day cycle.

It will be readily apparent to those skilled in the art that other antibody-drug conjugate compound doses or frequencies of administration that provide the desired therapeutic effect are suitable for use in the present invention.

Administration of the antibody-drug conjugate compound and gemcitabine can be on the same or different days provided that administration provides the desired thereapeutic effect. The present invention encompasses, for example, embodiments wherein gemcitabine is administered weekly for three consecutive weeks in a four week treatment cycle, e.g., on days 1, 8 and 15 of a 28 day cycle. The present invention encompasses, for example, embodiments wherein gemcitabine is administered two times in a four week treatment cycle, e.g., on days 1 and 15 of a 28 day cycle. The present invention encompasses, for example, embodiments wherein gemcitabine is administered two times in a three week treatment cycle, e.g., on days 1 and 8 or day 1 and 15 of a 21 day cycle. In some embodiments of the present invention, administration of the antibody-drug conjugate compound and gemcitabine will be on the same days, e.g., on days 1, 8, and 15 of a four week cycle or on days 1 and 15 of a four week cycle. In some embodiments of the present invention, administration of the antibody-drug conjugate compound and gemcitabine will be on the same and/or different days, e.g, the antibody drug conjugate will be administered on day 1 of a 21 day cycle and gemcitabine will be administered on day 1 and 8 or day 1 and 15 of the 21 day cycle. In some embodiments, the antibody-drug conjugate compound and gemcitabine will be administered on the same days and gemcitabine will be administered following completion of administration of the antibody-drug conjugate, e.g., gemcitabine will be administered less than 2 hours following administration of the antibody-drug conjugate, e.g., 30 minutes following administration of the antibody-drug conjugate. Alternative treatment schedules are encompassed by the present invention as long as they produce the desired result.

In some embodiments, gemcitabine will be administered at levels currently indicated in the art for the treatment of HL or at lower or higher levels than those currently indicated in the art for the treatment of HL provided that such dosage provides the desired therapeutic effect. Embodiments of the present invention include, for example, those wherein the gemcitabine regimen is administered at about the MTD, maximum tolerated dose. Embodiments of the present invention include those wherein gemcitabine is administered in a dose range of about 100 mg/m$^2$ to about 2000 mg/m$^2$, about 500 mg/m$^2$ to about 1500 mg/m$^2$, about 500 mg/m$^2$ to about 1250 mg/m$^2$, or about 750 mg/m$^2$ to about 1250 mg/m$^2$ at each administration. In particularly preferred embodiments, gemcitabine is administered in a dose range of about 750 mg/m$^2$ to about 1250 mg/m$^2$ at each administration, or about 1000 mg/m$^2$ to about 1250 mg/m$^2$ at each administration. For example, in some embodiments, gemcitabine will be administered in a dose range of 750 mg/m$^2$ to about 1250 mg/m$^2$ or about 1000 mg/m$^2$ to about 1250 mg/m$^2$ on days 1, 8, and 15 of a 28 day treatment cycle. In some embodiments, gemcitabine will be administered in a dose range of 750 mg/m² to about 1250 mg/m² or about 1000 mg/m² to about 1250 mg/m² on days 1 and 15 or days of a 28 day treatment cycle. In some embodiments, gemcitabine will be administered in a dose range of 750 mg/m² to about 1250 mg/m² or about 1000 mg/m² to about 1250 mg/m² on days 1 and 8 or days 1 and 15 of a 21 day treatment cycle. The present invention contemplates administration of gemcitabine for one or more treatment cycles, for example, 1, 2, 3, 4, 5, 6, or more treatment cycles. Embodiments of the present invention include those wherein gemcitabine is administerd by IV infusion over 30 minutes. In certain embodiments about 1000 mg/m² is delivered by IV infusion over 30 minutes on days 1, 8, and 15 of each 28 day treatment cycle. It will be understood that any of the dose ranges indicated herein for treatment with gemcitabine can be combined with any of the dose ranges indicated herein for treatment with the antibody-drug conjugate compound provided that administration provides the desired therapeutic effect, i.e., synergism.

In some particularly preferred examples of the present invention, administration of a synergistic amount of the therapeutic agents encompasses administering the antibody drug conjugate compound in a total range of about 0.5 mg/kg to about 5 mg/kg, about 0.6 mg/kg to about 5 mg/kg, about 0.6 mg/kg to about 2.7 mg/kg, about 0.8 mg/kg to about 2.7 mg/kg, about 1 mg/kg to about 5 mg/kg, about 1 mg/kg to about 4 mg/kg, about 1 mg/kg to about 3.5 mg/kg, about 1.5 mg/kg to about 3.5 mg/kg. or even about 1.8 mg/kg to about 2.5 mg/kg over a 21 or 28 day treatment cycle, irrespective of the dosing schedule, in combination with administering gemcitabine at standard dosing schedules known in the art, e.g., about 800 mg/m² to about 1500 mg/m² at each gemcitabine administration during the treatment cycle, preferably about 1000 mg/m² to about 1250 mg/m² at each gemcitabine administration during the treatment cycle (e.g, 1-3 times during the 21 or 28 day treatment cycle).

In some particularly preferred examples of the present invention, administration of a synergistic amount of the therapeutic agents encompasses administering the antibody drug conjugate compound once during the treatment cycle (e.g., a 21 or 28 day treatment cycle) in a range of about 0.5 to about 2.7 mg/kg, about 0.6 mg/kg to about 2.7 mg/kg, about 0.6 mg/kg to about 2 mg/kg, about 0.6 mg/kg to about 1 mg/kg, about 0.8 mg/kg to about 2.7 mg/kg, about 0.8 mg/kg to about 2.0 mg/kg, about 1 mg/kg to about 2.7 mg/kg, about 1.5 mg/kg to about 2.7 mg/kg, or even more preferably about 1.0 mg/kg to about 2 mg/kg or about 1.5 mg/kg to about 2 mg/kg of the subject's body weight in combination with administering gemcitabine at standard dosing schedules known in the art, e.g., about 800 mg/m² to about 1500 mg/m² at each gemcitabine administration during the treatment cycle, preferably about 1000 mg/m² to about 1250 mg/m² at each gemcitabine administration during the treatment cycle (e.g, 1-3 times during the treatment cycle). For example, in one embodiment, administration of a synergistic amount of the therapeutic agents includes administering the antibody drug conjugate compound once during a 3 week treatment cycle (e.g., on day 1 of a 21 day treatment cycle) in a range of about 0.5 mg/kg to about 2.7 mg/kg, about 0.6 mg/kg to about 2.7 mg/kg, about 0.8 mg/kg to about 2.0 mg/kg, about 1.5 mg/kg to about 2.7 mg/kg, or about 1.5 mg/kg to about 2 mg/kg of the subject's body weight in combination with administering gemcitabine on days 1 and 8 or days 1 and 15 of the 21 day treatment cycle in a range of about 800 mg/m² to about 1500 mg/m², preferably about 1000 mg/m² to about 1250 mg/m².

In some particularly preferred examples of the present invention, administration of a synergistic amount of the therapeutic agents encompasses administering the antibody drug conjugate compound three times during the treatment cycle (e.g., a 21 or 28 day treatment cycle) in a range of about 0.4 mg/kg to about 2 mg/kg, about 0.4 mg/kg to about 1.8 mg/kg, about 0.4 mg/kg to about 1 mg/kg, about 0.4 mg/kg to about 1.5 mg/kg at each administration in combination with administering gemcitabine at standard dosing schedules known in the art, e.g., about 800 mg/m² to about 1500 mg/m² at each gemcitabine administration during the treatment cycle, preferably about 1000 mg/m² to about 1250 mg/m² at each gemcitabine administration during the treatment cycle (e.g, 1-3 times during the treatment cycle). For example, in one embodiment, administration of a synergistic amount of the therapeutic agents includes administering the antibody drug conjugate compound on days 1, 8 and 15 of a 28 day cycle in a range of about 0.4 mg/kg to about 2 mg/kg, about 0.4 mg/kg to about 1.8 mg/kg, about 0.4 mg/kg to about 1 mg/kg of the subject's body weight, about 0.4 mg/kg to about 1.5 mg/kg of the subject's body weight at each administration in combination with administering gemcitabine on days 1, 8 and 15 of a 28 day cycle in a range of about 800 mg/m² to about 1250 mg/m², preferably about 1000 mg/m² to about 1250 mg/m² at each administration.

In some particularly preferred examples of the present invention, administration of a synergistic amount of the therapeutic agents encompasses administering the antibody drug conjugate compound two times during the treatment cycle (e.g., a 21 or 28 day treatment cycle) in a range of about 0.4 mg/kg to about 2.0 mg/kg, about 0.4 mg/kg to about 1.8 mg/kg, about 0.4 mg/kg to about 1 mg/kg, about 0.4 mg/kg to about 1.5 mg/kg at each administration in combination with administering gemcitabine at standard dosing schedules known in the art, e.g., about 800 mg/m² to about 1500 mg/m² at each gemcitabine administration during the treatment cycle, preferably about 1000 mg/m² to about 1250 mg/m² at each gemcitabine administration during the treatment cycle (e.g, 1-3 times during the treatment cycle). For example, administration of a synergistic amount of the therapeutic agents includes administering the antibody drug conjugate compound on days 1 and 15 of a 28 day cycle in a range of about 0.4 mg/kg to about 2 mg/kg, about 0.4 mg/kg to about 1.8 mg/kg, about 0.4 mg/kg to about 1 mg/kg of the subject's body weight, about 0.4 mg/kg to about 1.5 mg/kg of the subject's body weight at each administration in combination with administering gemcitabine on days 1, 8 and 15 of a 28 day cycle in a range of about 800 mg/m² to about 1250 mg/m², preferably about 1000 mg/m² to about 1250 mg/m² at each administration.

In embodiments of the present invention wherein treatment comprises administration of the antibody-drug conjugate compound and the chemotherapeutic regimen comprising bleomycin, vinblastine and dacarbazine or doxorubicin, bleomycin, vinblastine and dacarbazine (ABVD), administration of the antibody-drug conjugate compound can be on the same or different days as administration of the chemotherapeutic regimen provided that administration provides the desired therapeutic effect. The present invention encompasses, for example, embodiments wherein the chemotherapeutic regimen is administered on days 1 and 15 of a four week cycle. In certain embodiments, both the chemotherapeutic regimen and the antibody-drug conjugate compound are administered on days 1 and 15 of a four week cycle. In other embodiments, the chemotherapeutic regimen will be administered on days 1 and 15 of a four week cycle and the antibody-drug conjugate compound will be administered on days 1, 8 and 15 of a four week cycle or on day 1 of a three or four week cycle. Other administration schedules are encompassed by the present methods. Methods of administering the drugs bleomycin, vinblastine and dacarbazine or doxorubicin, bleomycin, vinblastine and dacarbazine in a chemotherapeutic regimen for the treatment of Hodgkin lymphoma are known. Typically, administration is on days 1 and 15 of a 28 day cycle and doxorubicin is administered at a dosage of 25 mg/m$^2$, bleomycin is administered at a dosage of 10 U/m$^2$, vinblastine is administered at a dosage of 6 mg/m$^2$, and dacarbazine is administered at a dosage of 375 mg/m$^2$. Embodiments of the present invention include those wherein the drugs are administered at the levels currently indicated in the art for the treatment of HL. Embodiments of the present invention include those wherein the drugs are administered at lower or higher levels than currently indicated in the art for the treatment of HL provided that administration provides the desired therepauetic effect. In certain instances, dosage levels can be reduced when combined with additional therapeutic agents. Embodiments of the present invention include, for example, those wherein the ABVD regimen is administered at about the MTD, maximum tolerated dose. In certain embodiments, doxorubicin is administered in a range of 0-35 mg/m$^2$, 10-30 mg/m$^2$ or 10-25 mg/m$^2$ at each administration, e.g., on days 1 and 15 of a 28 day treatment cycle; bleomycin is administered in a range of 2 to 15 U/m$^2$, 5 to 15 U/m$^2$, or 5 to 10 U/m$^2$ at each administration, e.g., on days 1 and 15 of a 28 day treatment cycle, vinblasine is administered in range of 1-8 mg/m$^2$, 2-6 mg/m$^2$ or 3-6 mg/m$^2$ at each administration, e.g., on days 1 and 15 of a 28 day treatment cycle, and dacarbazine is administered in a range of 100-450 mg/m$^2$, 150-375 mg/m$^2$, 200-375 mg/m$^2$ or 300-375 mg/m$^2$ at each administration, e.g., on days 1 and 15 of a 28 day treatment cycle provided that administration provides the desired therapeutic effect. The present invention contemplates administration of the ABVD regimen for one or more treatment cycles, for example, 1, 2, 3, 4, 5, 6, or more treatment cycles. It will be understood that any of the dose ranges indicated herein for treatment with doxorubicin, bleomycin, vinblastine and dacarbazine can be combined with any of the dose ranges indicated herein for treatment with the antibody-drug conjugate compound provided that administration provides the desired therapeutic effect.

In some particularly preferred examples of the present invention, administration of a synergistic amount of the therapeutic agents encompasses administering the antibody drug conjugate compound in a total range of about 0.5 mg/kg to about 5 mg/kg, about 0.6 mg/kg to about 5 mg/kg, about 0.6 mg/kg to about 2.7 mg/kg, about 0.8 mg/kg to about 2.7 mg/kg, about 1 mg/kg to about 5 mg/kg, about 1 mg/kg to about 4 mg/kg, about 1 mg/kg to about 3.5 mg/kg, about 1.5 mg/kg to about 3.5 mg/kg. or even about 1.8 mg/kg to about 2.5 mg/kg over a 21 or 28 day treatment cycle, irrespective of the dosing schedule, in combination with administering ABVD at standard dosing schedules known in the art.

In some particularly preferred examples of the present invention, administration of a synergistic amount of the therapeutic agents encompasses administering the antibody drug conjugate compound once during the treatment cycle (e.g., a 21 or 28 day treatment cycle) in a range of about 0.5 to about 2.7 mg/kg, about 0.6 mg/kg to about 2.7 mg/kg, about 0.6 mg/kg to about 2 mg/kg, about 0.6 mg/kg to about 1 mg/kg, about 0.8 mg/kg to about 2.7 mg/kg, about 0.8 mg/kg to about 2.0 mg/kg, about 1 mg/kg to about 2.7 mg/kg, about 1.5 mg/kg to about 2.7 mg/kg, or even more preferably about 1.0 mg/kg to about 2 mg/kg or about 1.5 mg/kg to about 2 mg/kg of the subject's body weight, in combination with administering ABVD at standard dosing schedules known in the art.

In some particularly preferred examples of the present invention, administration of a synergistic amount of the therapeutic agents encompasses administering the antibody drug conjugate compound three times during the treatment cycle (e.g., a 21 or 28 day treatment cycle) in a range of about 0.4 mg/kg to about 2 mg/kg, about 0.4 mg/kg to about 1.8 mg/kg, about 0.4 mg/kg to about 1 mg/kg, about 0.4 mg/kg to about 1.5 mg/kg at each administration in combination with administering ABVD at standard dosing schedules known in the art.

In some particularly preferred examples of the present invention, administration of a synergistic amount of the therapeutic agents encompasses administering the antibody drug conjugate compound two times during the treatment cycle (e.g., a 21 or 28 day treatment cycle) in a range of about 0.4 mg/kg to about 2.0 mg/kg, about 0.4 mg/kg to about 1.8 mg/kg, about 0.4 mg/kg to about 1 mg/kg, about 0.4 mg/kg to about 1.5 mg/kg at each administration, in combination with administering ABVD at standard dosing schedules known in the art.

I. Pharmaceutical Compositions

Various delivery systems are known and can be used to administer the antibody-drug conjugate compounds and the chemotherapeutic agents. Methods of introduction include, but are not limited to, intradermal, intramuscular, intraperitoneal, intravenous, and subcutaneous routes. Administration can be, for example by infusion or bolus injection. In certain preferred embodiments, administration of both the chemotherapeutic agent and the antibody-drug conjugate compound is by infusion.

The antibody-drug conjugate compound and chemotherapeutic agents can be administered as pharmaceutical compositions comprising one or more pharmaceutically compatible ingredients. For example, the pharmaceutical composition typically includes one or more pharmaceutical carriers (e.g., sterile liquids, such as water and oils, including those of petroleum, animal, vegetable or synthetic origin, such as peanut oil, soybean oil, mineral oil, sesame oil and the like). Water is a more typical carrier when the pharmaceutical composition is administered intravenously. Saline solutions and aqueous dextrose and glycerol solutions can also be employed as liquid carriers, particularly for injectable solutions. Suitable pharmaceutical excipients are known in the art. The composition, if desired, can also contain minor amounts of wetting or emulsifying agents, or pH buffering agents. Examples of suitable pharmaceutical carriers are described in "Remington's Pharmaceutical Sciences" by E. W. Martin. The formulations correspond to the mode of administration.

In typical embodiments, the pharmaceutical composition is formulated in accordance with routine procedures as a pharmaceutical composition adapted for intravenous administration to human beings. Typically, compositions for intravenous administration are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed, for example, with an infusion bottle containing sterile pharmaceutical grade water or saline. Where the pharmaceutical is administered by injection, an ampoule of sterile water for injection or saline can be, for example, provided so that the ingredients can be mixed prior to administration.

J. Subjects

The methods of the present invention encompass administering combination therapy to a subject for the treatment of Hodgkin lymphoma.

The subjects to be treated with the methods of the present invention are those that have been diagnosed with Hodgkin lymphoma or are suspected of having Hodgkin lymphoma. Diagnosis can be by methods known in the art, including, for example, lymph node biopsy. After Hodgkin lymphoma is diagnosed, if desired, a subject can be classified according to stage of disease using one of the known classification schemes. The Cotswolds staging classification scheme is one such classification scheme. Briefly, stage I can be characterized by involvement of a single lymph node region or lymphoid structure; stage II can be characterized by involvement of two or more lymph node regions or lymph node structures on the same side of the diaphragm; stage III can be characterized by involvement of lymph node regions or lymph node structures on both sides of the diaphragm; and stage IV can be characterized by diffuse or disseminated involvement of one or more extranodal organs or tissue beyond that designated E, with or without lymph node involvement. The designation E refers to extranodal contiguous extension that can be encompassed within an irradiation field appropriate for nodal disease of the same anatomic extent. Subjects in stages I or II can have a favorable or unfavorable prognosis depending on the presence or absence of certain clinical features. For the purposes of the present invention, subjects with early stage disease are classified in Stage I or II whereas subjects with advanced stage disease are classified in Stages III or IV. The methods of the present invention can be used to treat a subject classified in any one of the four stages of disease, including a subject with advanced stage disease.

The methods of the present invention encompass treating a subject who is newly diagnosed and has not previously been treated for HL.

The methods of the present invention also can be used to treat subjects with refractory and/or relapsed Hodgkin lymphoma.

A subject with refractory Hodgkin lymphoma is a subject who does not respond to therapy for HL, i.e., the subject continues to experience disease progression despite therapy.

A subject with relapsed Hodgkin lymphoma is a subject who has responded to therapy for HL at one point, but has had a reoccurence or further progression of disease following the response.

The methods of the present invention also encompass treating a subject who has previously been treated with a first-line chemotherapy regimen for Hodgkin lymphoma or a subject who has been treated with both a first-line chemotherapy regimen and/or a salvage chemotherapy regimen. First line chemotherapeutic regimens for Hodgkin lymphoma include, for example, the ABVD regimen (Bonadonna and Santoro, Cancer Treat Rev 1982; 9:21-35), the BEACOPP regimen (Diehl et al., N Engl J Med 2003; 348:2386-2395), the escalated BEACOPP regimen (Diehl et al., N Engl J Med 2003; 348:2386-2395), the MOPP regimen (Devita et al., Ann Inter Med 1970:73:881-895), and the Stanford V regimen (Horning et al., J Clin Oncol 2000; 18:972-980). Salvage chemotherapy regimens include, for example, the ESHAP regimen (Aparicio et al., Ann Ocol 1999; 10:593-595), the modified Stanford V regimen (Aviles et al., Med Oncol 2001; 18:261-267), the GDP regimen (Baetz et al., Ann Oncol 2003; 14:1762-1767), the Mini-Beam regimen (Colwill et al., J Clin Oncol 1995; 13:396-402, Fernandez-Jimenez et al., Haematologica 1999; 84:1007-1011), the MIME regimen (Enblad et al., Eur J Haematol 1998; 60:166-171), the MINE regimen (Ferme et al., Ann Oncol 1995; 6:543-549), the IEE regimen (Jackson et al., Leuk Lymphoma 2000; 37:561-570), the DHAP regimen (Josting et al., Ann Oncol 2002; 13:1628-1635), the ICE regimen (Moskowitz et al., Semin Oncol 2004; 31 (suppl):54-59), the IIVP regimen (Oyan et al., Biol Blood Marrow Transplant 2005; 11:688-697), the IVE regimen (Proctor et al., Eur J Haematol 2001; 64 (suppl):28-32), the VIP regimen (Ribrag et al., Bome Marrow Transplant 1998; 21:969-974), the ASHAP regimen (Rodriguez et al., Blood 1999; 93:3632-3636), the Dexa-BEAM regimen (Schmitz et al., Lancet 2002; 359:2065-2071), the CEP regimen (Szanto et al., Oncology 1991; 48:456-458), the CN30P regimen (Walewski et al., Med. Oncol. 2000; 17:195-202), and the MVC regimen (Wiernik et al., Cancer J Sci Am 1998; 4:254-260).

The methods of the present invention also encompass treating a subject who has previously undergone a stem cell transplant.

K. Anti-CD30 Antibodies

Anti-CD30 antibodies suitable for use in accordance with the present compositions and methods include any antibody that specifically binds to the CD30 antigen. Anti-CD30 antibodies are preferably monoclonal and can include, for example, chimeric (e.g., having a human constant region and mouse variable region), humanized, or human antibodies; single chain antibodies; or the like. The immunoglobulin molecules can be of any type (e.g., IgG, IgE, IgM, IgD, IgA and IgY), class (e.g., IgG1, IgG2, IgG3, IgG4, IgA1 and IgA2) or subclass of immunoglobulin molecule.

In certain embodiments, the antibody is an antigen-binding antibody fragment such as, for example, a Fab, a F(ab'), a F(ab')$_2$, a Fd chain, a single-chain Fv (scFv), a single-chain antibody, a disulfide-linked Fv (sdFv), a fragment comprising either a $V_L$ or $V_H$ domain, or fragments produced by a Fab expression library, or a CD30-binding fragment of any of the above antibodies. Antigen-binding antibody fragments, including single-chain antibodies, can comprise the variable region(s) alone or in combination with the entirety or a portion of the following: hinge region, CH1, CH2, CH3 and CL domains. Also, antigen-binding fragments can comprise any combination of variable region(s) with a hinge region, CH1, CH2, CH3 and CL domains. Typically, the antibodies are human, rodent (e.g., mouse and rat), donkey, sheep, rabbit, goat, guinea pig, camelid, horse, or chicken. As used herein, "human" antibodies include antibodies having the amino acid sequence of a human immunoglobulin and include antibodies isolated from human immunoglobulin libraries, from human B cells, or from animals transgenic for one or more human immunoglobulin (see, for example in U.S. Pat. Nos. 5,939, 598 and 6,111,166).

The antibodies may be monospecific, bispecific, trispecific, or of greater multispecificity (See, e.g., PCT publications WO 93/17715; WO 92/08802; WO 91/00360; and WO 92/05793; Tutt et al., 1991, J Immunol 147:60-69; U.S. Pat. Nos. 4,474,893; 4,714,681; 4,925,648; 5,573,920; and 5,601, 819; Kostelny et al., 1992, J Immunol 148:1547-1553.)

Exemplary anti-CD30 antibodies include, but are not limited to, humanized or chimeric AC10 or HeFi-1 antibodies. Accordingly, an exemplary anti-CD30 antibody comprises one or more CDRs of murine HeFi-1 (SEQ ID NO:20, SEQ ID NO:22; SEQ ID NO:24; SEQ ID NO:28, SEQ ID NO:30 or SEQ ID NO:32) or murine AC10 (SEQ ID NO:4; SEQ ID NO:6; SEQ ID NO:8; SEQ ID NO:12; SEQ ID NO:14; or SEQ ID NO:16). In some embodiments, the anti-CD30 antibody comprises one/or one or more variable regions of murine HeFi-1 (SEQ ID NO:18 or SEQ ID NO:26) or murine AC10 (SEQ ID NO:2 or SEQ ID NO:10). A table indicating the region of AC10 or HeFi-1 to which each SEQ ID NO corresponds to is provided below:

TABLE 1

| MOLECULE | NUCLEOTIDE OR AMINO ACID | SEQ ID NO |
|---|---|---|
| AC10 Heavy Chain Variable Region | Nucleotide | 1 |
| AC10 Heavy Chain Variable Region | Amino Acid | 2 |
| AC10 Heavy Chain-CDR1(H1) | Nucleotide | 3 |
| AC 10 Heavy Chain-CDR1(H1) | Amino Acid | 4 |
| AC 10 Heavy Chain-CDR2(H2) | Nucleotide | 5 |
| AC 10 Heavy Chain-CDR2(H2) | Amino Acid | 6 |
| AC 10 Heavy Chain-CDR3(H3) | Nucleotide | 7 |
| AC 10 Heavy Chain-CDR3(H3) | Amino Acid | 8 |
| AC 10 Light Chain Variable Region | Nucleotide | 9 |
| AC 10 Light Chain Variable Region | Amino Acid | 10 |
| AC 10 Light Chain-CDR1(L1) | Nucleotide | 11 |
| AC 10 Light Chain-CDR1(L1) | Amino Acid | 12 |
| AC 10 Light Chain-CDR2(L2) | Nucleotide | 13 |
| AC 10 Light Chain-CDR2(L2) | Amino Acid | 14 |
| AC 10 Light Chain-CDR3(L3) | Nucleotide | 15 |
| AC 10 Light Chain-CDR3(L3) | Amino Acid | 16 |
| HeFi-1 Heavy Chain Variable Region | Nucleotide | 17 |
| HeFi-1 Heavy Chain Variable Region | Amino Acid | 18 |
| HeFi-1 Heavy Chain-CDR1(H1) | Nucleotide | 19 |
| HeFi-1 Heavy Chain-CDR1(H1) | Amino Acid | 20 |
| HeFi-1 Heavy Chain-CDR2(H2) | Nucleotide | 21 |
| HeFi-1 Heavy Chain-CDR2(H2) | Amino Acid | 22 |
| HeFi-1 Heavy Chain-CDR3(H3) | Nucleotide | 23 |
| HeFi-1 Heavy Chain-CDR3(H3) | Amino Acid | 24 |
| HeFi-1 Light Chain Variable Region | Nucleotide | 25 |
| HeFi-1 Light Chain Variable Region | Amino Acid | 26 |
| HeFi-1 Light Chain-CDR1(L1) | Nucleotide | 27 |
| HeFi-1 Light Chain-CDR1(L1) | Amino Acid | 28 |
| HeFi-1 Light Chain-CDR2(L2) | Nucleotide | 29 |
| HeFi-1 Light Chain-CDR2(L2) | Amino Acid | 30 |
| HeFi-1 Light Chain-CDR3(L3) | Nucleotide | 31 |
| HeFi-1 Light Chain-CDR3(L3) | Amino Acid | 32 |
| Human gamma I constant region | Amino Acid | 33 |
| Human kappa constant region | Amino Acid | 34 |

Exemplary anti-CD30 antibodies include functional derivatives or analogs of AC10 and HeFi-1. As used herein, the term "functional" in this context indicates that the functional derivate or analog of AC10 and HeFi-1 is capable of binding to CD30.

In some embodiments, anti-CD30 antibodies not only immunospecifically binds CD30 but also can exert cytostatic and/or cytotoxic effect on malignant cells in HL wherein the cytostatic or cytotoxic effect is complement-independent and can be achieved in the absence of (i) conjugation to a cytostatic or cytotoxic agent and (ii) effector cells.

The anti-CD30 antibodies may be described or specified in terms of the particular CDRs they comprise. In some embodiments, the antibodies comprise the CDRs of AC10 and/or HeFi-1. In some embodiments, the antibodies are chimeric or humanized forms of AC10 or HeFi-1. The invention encompasses an antibody comprising a heavy or light chain variable domain, said variable domain comprising (a) a set of three CDRs, in which said set of CDRs are from murine monoclonal antibody AC10 or HeFi-1, and (b) a set of four framework regions, in which said set of framework regions differs from the set of framework regions in murine monoclonal antibody AC10 or HeFi-1, respectively, and in which said antibody immunospecifically binds CD30.

In a specific embodiment, the invention encompasses an antibody comprising a heavy chain variable domain, said variable domain comprising (a) a set of three CDRs, in which said set of CDRs comprises SEQ ID NO:4, 6, or 8 or comprises amino acid sequences that are substantially identical to the amino acid sequences set forth in SEQ ID NO:4, 6, or 8 and (b) a set of four framework regions, in which said set of framework regions differs from the set of framework regions in murine monoclonal antibody AC10, and in which said antibody immunospecifically binds CD30.

In a specific embodiment, the invention encompasses an antibody comprising a heavy chain variable domain, said variable domain comprising (a) a set of three CDRs, in which said set of CDRs comprises SEQ ID NO:20, 22 or 24 or comprises amino acid sequences that are substantially identical to the amino acid sequences set forth in SEQ ID NO:20, 22, or 24 and (b) a set of four framework regions, in which said set of framework regions differs from the set of framework regions in murine monoclonal antibody HeFi-1, and in which said antibody immunospecifically binds CD30.

In a specific embodiment, the invention encompasses an antibody comprising a light chain variable domain, said variable domain comprising (a) a set of three CDRs, in which said set of CDRs comprises SEQ ID NO:12, 14 or 16 or comprises amino acid sequences that are substantially identical to the amino acid sequences set forth in SEQ ID NO:12, 14, or 16, and (b) a set of four framework regions, in which said set of framework regions differs from the set of framework regions in murine monoclonal antibody AC10, and in which said antibody immunospecifically binds CD30.

In a specific embodiment, the invention encompasses an antibody comprising a light chain variable domain, said variable domain comprising (a) a set of three CDRs, in which said set of CDRs comprises SEQ ID NO:28, 30, or 32 or comprises amino acid sequences that are substantially identical to the amino acid sequences set forth in SEQ ID NO:28, 30, or 32, and (b) a set of four framework regions, in which said set of framework regions differs from the set of framework regions in murine monoclonal antibody HeFi-1, and in which said antibody immunospecifically binds CD30.

The present invention encompasses embodiments wherein a chimeric AC10 antibody comprises the heavy chain variable region set forth in SEQ ID NO:2, the light chain variable region set forth in SEQ ID NO:10, the human gamma I constant region set forth in SEQ ID NO:33 or amino acids 1 to 329 of SEQ ID NO:33 and the human kappa constant region set forth in SEQ ID NO:34.

Additionally, the antibodies can also be described or specified in terms of their primary structures. Anti-CD30 antibodies having at least 80%, at least 85%, at least 90%, at least 95% and most preferably at least 98% identity (as calculated using methods known in the art and described herein) to the variable regions of murine AC10 or HeFi-1 are also included in the present invention. Antibodies of the present invention may also be described or specified in terms of their binding affinity to CD30. Preferred binding affinities include those with a dissociation constant or Kd less than $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times^{-13}$ M, $10^{-13}$ M, $5 \times 10^{-14}$ M, $10^{-14}$ M, $5 \times 10^{-15}$ M, or $10^{-15}$ M.

The antibodies can be purified, for example by affinity chromatography with the CD30 antigen. In certain embodiments, the antibody is at least 50%, at least 60%, at least 70% or at least 80% pure. In other embodiments, the antibody is more than 85% pure, more than 90% pure, more than 95% pure or more than 99% pure.

The antibodies also include antibodies that are modified, e.g., by the attachment of any type of molecule to the antibody such that attachment does not prevent the antibody from binding to CD30. For example, but not by way of limitation, the term "antibody" includes antibodies that have been modified, e.g., by glycosylation, deglycosylation, acetylation, pegylation, phosphylation, amidation, derivatization by known protecting/blocking groups, linkage to a cellular ligand or other protein, etc. Any of numerous chemical modifications may be carried out by known techniques, including, but not limited to specific chemical cleavage, acetylation, formylation, metabolic synthesis of tunicamycin, etc.

The antibodies of the present invention can be generated by any suitable method known in the art. Polyclonal antibodies to CD30 can be produced by various procedures well known in the art. For example, CD30 can be administered to various host animals including, but not limited to, rabbits, mice, rats, and the like, to induce the production of sera containing polyclonal antibodies specific for the protein. Various adjuvants may be used to increase the immunological response, depending on the host species.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed., 1988); Hammerling, et al., in: Monoclonal Antibodies and T-Cell Hybridomas 563-681 (Elsevier, N.Y., 1981) (said references incorporated by reference in their entireties).

Methods for producing and screening for specific antibodies using hybridoma technology are routine and well known in the art. In a non-limiting example, mice can be immunized with CD30 or a cell expressing CD30 or a fragment or derivative thereof. Once an immune response is detected, e.g., antibodies specific for CD30 are detected in the mouse serum, the mouse spleen is harvested and splenocytes isolated. The splenocytes are then fused by well known techniques to any suitable myeloma cells, for example cells from cell line SP20 available from the American Type Culture Collection, Rockville, Md. (ATCC). Hybridomas are selected and cloned by limited dilution. The hybridoma clones are then assayed by methods known in the art for cells that secrete antibodies capable of binding CD30. Ascites fluid, which generally contains high levels of antibodies, can be generated by injecting mice with positive hybridoma clones.

Accordingly, the present invention provides methods of generating monoclonal antibodies as well as antibodies produced by the method comprising culturing a hybridoma cell secreting an antibody wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind to CD30.

Antibody fragments which recognize specific epitopes may be generated by known techniques. For example, Fab and $F(ab')_2$ fragments may be produced by proteolytic cleavage of immunoglobulin molecules, using enzymes such as papain (to produce Fab fragments) or pepsin (to produce $F(ab')_2$ fragments). $F(ab')_2$ fragments contain the variable region, the light chain constant region and the CH 1 domain of the heavy chain.

Antibodies can also be generated using various phage display methods known in the art. In phage display methods, functional antibody domains are displayed on the surface of phage particles which carry the nucleic acid sequences encoding them. In a particular embodiment, such phage can be utilized to display antigen binding domains expressed from a repertoire or combinatorial antibody library (e.g., human or murine). In particular, DNA sequences encoding $V_H$ and $V_L$ domains are amplified from animal cDNA libraries (e.g., human or murine cDNA libraries of lymphoid tissues). The DNA encoding the $V_H$ and $V_L$ domains are recombined together with an scFv linker by PCR and cloned into a phagemid vector (e.g., p CANTAB 6 or pComb 3 HSS). The vector is electroporated in E. coli and the E. coli is infected with helper phage. Phage used in these methods are typically filamentous phage including fd and M13 binding domains expressed from phage with Fab, Fv or disulfide stabilized Fv antibody (dsFv) domains recombinantly fused to either the phage gene III or gene VIII protein. Phage expressing an antigen binding domain that binds to CD30 or an AC10 or HeFi-1 variable region can be selected or identified with antigen e.g., using labeled antigen or antigen bound or captured to a solid surface or bead. Examples of phage display methods that can be used to make the antibodies of the present invention include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology, 191-280; PCT Application No. PCT/GB91/O1 134; PCT Publications WO 90/02809; WO 91/10737; WO 92/01047; WO 92/18619; WO 93/1 1236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and $F(ab')_2$ fragments can also be employed using methods known in the art such as those disclosed in PCT publication WO 92/22324; Mullinax et al., BioTechniques 1992, 12(6):864-869; and Sawai et al., 1995, AJRI 34:26-34; and Better et al., 1988, Science 240:1041-1043 (said references incorporated by reference in their entireties).

Examples of techniques which can be used to produce single-chain Fvs and antibodies include those described in U.S. Pat. Nos. 4,946,778 and 5,258,498; Huston et al., 1991, Methods in Enzymology 203:46-88; Shu et al., 1993, PNAS 90:7995-7999; and Skerra et al., 1988, Science 240:1038-1040. For some uses, including in vivo use of antibodies in humans and in vitro proliferation or cytotoxicity assays, it is preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science, 1985, 229: 1202; Oi et al., 1986, BioTechniques 4:214; Gillies et al., 1989, J. Immunol. Methods 125:191-202; U.S. Pat. Nos. 5,807,715; 4,816,567; and 4,816,397, which are incorporated herein by reference in their entirety. Humanized antibodies are antibody molecules from non-human species antibody that binds the desired antigen having one or more CDRs from the non-human species and framework and constant regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., 1988, Nature 332:323, which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology, 1991, 28 (4/5):489-498; Studnicka et al., 1994, Protein Engineering 7(6):805-814; Roguska. et al., 1994, PNAS 91:969-973), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which express human immunoglobulin genes. For an overview of this technology for producing human antibodies, see, Lonberg and Huszar, 1995, Int. Rev. Immunol. 13:65-93. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Amgen. (Thousand Oaks, Calif.) and Medarex (Princeton, N.J.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., 1994, Bio/technology 12:899-903).

Antibodies for use in the present invention include chimeric and humanized AC10 as well as chimeric and humanized HeFi-1. Antibodies for use in the present invention include those that competitively inhibit binding of murine AC10 or HeFi-1 to CD30 as determined by any method known in the art for determining competitive binding. For example, the antibody can inhibit binding of AC10 or HeFi-1 to CD30 by at least 50%, at least 60%, at least 70%, at least 80%, at least 85%, at least 90%, or even at least 95%. One example of a competitive binding assay is a radioimmunoassay comprising the incubation of labeled CD30 (e.g., $^3$H or $^{125}$I) with the antibody of interest in the presence of increasing amounts of unlabeled CD30, and the detection of the antibody bound to the labeled CD30. The affinity of the antibody for CD30 and the binding off-rates can then be determined from the data by Scatchard plot analysis. Competition with a second antibody (such as AC10 or HeFi-1) can also be determined using radioimmunoassays. In this case, CD30 is incubated with the antibody of interest conjugated to a labeled compound (e.g., $^3$H or $^{125}$I) in the presence of increasing amounts of an unlabeled second antibody. Antibodies for use in the present invention also include antibodies other than chimeric or humanized AC10 or HeFi-1 that specifically bind to CD30.

One method which detects protein interactions in vivo, the two-hybrid system, is described in detail for illustration purposes only and not by way of limitation. One version of this system has been described (Chien et al., 1991, Proc. Natl. Acad. Sci. USA, 88:9578-9582) and is commercially available from Clontech (Palo Alto, Calif.).

Once a CD30-binding protein is identified, if desired, its ability (alone or when multimerized or fused to a dimerization or multimerization domain) to elicit a cytostatic or cytotoxic effect on HL cells can be determined by contacting a culture of an HL cell line, such as L428, L450, HLLM2 or KM-H2, with the protein. Culture conditions are most preferably about 5,000 cells in a culture area of about 0.33 cm$^2$, and the contacting period being approximately 72 hours. The culture is then exposed to 0.5 µCi of $^3$H-thymidine during the final 8 hours of the 72-hour period and the incorporation of $^3$H-thymidine into cells of the culture is measured. The protein has a cytostatic or cytotoxic effect on the HL cell line if the cells of the culture have reduced $^3$H-thymidine incorporation compared to cells of the same cell line cultured under the same conditions but not contacted with the protein. There are many other cytotoxicity assays known to those of skill in the art. Any one of them can be used in the present methods.

The anti-CD30 antibodies that are useful in the present methods can be produced by any method known in the art for the synthesis of proteins, typically, e.g., by recombinant expression techniques. Recombinant expression of an antibody or derivative thereof that binds to CD30 and depletes or inhibits the proliferation of CD30-expressing cells can include construction of an expression vector containing a nucleic acid that encodes the antibody or derivative thereof. Once a nucleic acid encoding such a protein has been obtained, the vector for the production of the protein molecule may be produced by recombinant DNA technology using techniques well known in the art. Standard techniques such as, for example, those described in Sambrook and Russell, *Molecular Cloning: A Laboratory Manual* (Cold Spring Harbor Laboratory Press, Cold Spring Harbor, N.Y., 3rd ed., 2001); Sambrook et al., *Molecular Cloning: A Laboratory Manual* (Cold Spring Harbor Laboratory Press, Cold Spring Harbor, N.Y., 2nd ed., 1989); *Short Protocols in Molecular Biology* (Ausubel et al., John Wiley & Sons, New York, 4th ed., 1999); and Glick & Pasternak, *Molecular Biotechnology: Principles and Applications of Recombinant DNA* (ASM Press, Washington, D.C., 2nd ed., 1998) can be used for recombinant nucleic acid methods, nucleic acid synthesis, cell culture, transgene incorporation, and recombinant protein expression.

For example, for recombinant expression of an anti-CD30 antibody, an expression vector may encode a heavy or light chain thereof, or a heavy or light chain variable domain, operably linked to a promoter. An expression vector may include, for example, the nucleotide sequence encoding the constant region of the antibody molecule (see, e.g., PCT Publication WO 86/05807; PCT Publication WO 89/01036; and U.S. Pat. No. 5,122,464); and the variable domain of the antibody may be cloned into such a vector for expression of the entire heavy or light chain. The expression vector is transferred to a host cell by conventional techniques, and the transfected cells are then cultured by conventional techniques to produce the anti-CD30 antibody. In typical embodiments for the expression of double-chained antibodies, vectors encoding both the heavy and light chains can be co-expressed in the host cell for expression of the entire immunoglobulin molecule.

A variety of prokaryotic and eukaryotic host-expression vector systems can be utilized to express an anti-CD30 antibody or derivative thereof. Typically, eukaryotic cells, particularly for whole recombinant anti-CD30 antibody molecules, are used for the expression of the recombinant protein. For example, mammalian cells such as Chinese hamster ovary cells (CHO), in conjunction with a vector such as the major intermediate early gene promoter element from human cytomegalovirus, is an effective expression system for the production of anti-CD30 antibodies (see, e.g., Foecking et al., 1986, *Gene* 45:101; Cockett et al., 1990, *Bio/Technology* 8:2). Anti-CD30 antibodies can also be expressed using the CHEF system. (See, e.g., U.S. Pat. No. 5,888,809.)

Other host-expression systems include, for example, plasmid-based expression systems in bacterial cells (see, e.g., Ruther et al., 1983, *EMBO* 1, 2:1791; Inouye & Inouye, 1985, *Nucleic Acids Res.* 13:3101-3109; Van Heeke & Schuster, 1989, *J. Biol. Chem.* 24:5503-5509); insect systems such as, e.g., the use of *Autographa californica* nuclear polyhedrosis virus (AcNPV) expression vector in *Spodoptera frugiperda* cells; and viral-based expression systems in mammalian cells, such as, e.g., adenoviral-based systems (see, e.g., Logan & Shenk, 1984, *Proc. Natl. Acad. Sci. USA* 81:355-359; Bittner et al., 1987, *Methods in Enzymol.* 153:51-544).

In addition, a host cell strain can be chosen that modulates the expression of the inserted sequences, or modifies and processes the gene product in the specific fashion desired. Appropriate cell lines or host systems can be chosen to ensure the correct modification and processing (e.g., glycosylation, phosphorylation, and cleavage) of the foreign protein expressed. To this end, eukaryotic host cells which possess the cellular machinery for proper processing of the primary transcript and gene product can be used. Such mammalian host cells include, for example, CHO (e.g., DG44 and CHO—S), VERO, BHK, HeLa, COS, MDCK, 293, 3T3, and W138.

A stable expression system is typically used for long-term, high-yield production of recombinant anti-CD30 antibody. For example, cell lines that stably express the anti-CD30 antibody or derivative thereof can be engineered by transformation of host cells with DNA controlled by appropriate expression control elements (e.g., promoter, enhancer, sequences, transcription terminators, polyadenylation sites) and a selectable marker, followed by growth of the transformed cells in a selective media. The selectable marker confers resistance to the selection and allows cells to stably integrate the DNA into their chromosomes and grow to form foci which in turn can be cloned and expanded into cell lines. A number of selection systems can be used, including, for example, the herpes simplex virus thymidine kinase, hypoxanthineguanine phosphoribosyltransferase, and adenine phosphoribosyltransferase genes, which can be employed in tk⁻, hgprt⁻ or aprt⁻ cells, respectively. Also, antimetabolite resistance can be used as the basis of selection for the following genes: dhfr, which confers resistance to methotrexate; gpt, which confers resistance to mycophenolic acid; neo, which confers resistance to the aminoglycoside G-418; and hygro, which confers resistance to hygromycin. Methods commonly known in the art of recombinant DNA technology can be routinely applied to select the desired recombinant clone, and such methods are described, for example, in *Current Protocols in Molecular Biology* (Ausubel et al. eds., John Wiley & Sons, N.Y., 1993); Kriegler, *Gene Transfer and Expression, A Laboratory Manual* (Stockton Press, N.Y., 1990); *Current Protocols in Human Genetics* (Dracopoli et al. eds., John Wiley & Sons, N.Y., 1994, Chapters 12 and 13); and Colberre-Garapin et al., 1981, *J. Mol. Biol.* 150:1.

Once an anti-CD30 antibody has been produced (e.g., by an animal, chemical synthesis, or recombinant expression), it can be purified by any suitable method for purification of proteins, including, for example, by chromatography (e.g., ion exchange or affinity chromatography (such as, for example, Protein A chromatography for purification of antibodies having an intact Fc region), centrifugation, differential solubility, or by any other standard technique for the purification of proteins. An anti-CD30 antibody can, for example, be fused to a marker sequence, such as a peptide, to facilitate purification by affinity chromatography. Suitable marker amino acid sequences include, e.g., a hexa-histidine peptide, such as the tag provided in a pQE vector (QIAGEN, Inc., 9259 Eton Avenue, Chatsworth, Calif., 91311), and the "HA" tag, which corresponds to an epitope derived from the influenza hemagglutinin protein (Wilson et al., 1984, Cell 37:767), and the "flag" tag.

L. Antibody-Drug Conjugate Units

The methods described herein encompass the use of antibodies that (a) specifically bind to CD30 and (b) are conjugated to an auristatin compound. The antibody-drug conjugate compounds comprise an anti-CD30 antibody, covalently linked to at least one drug unit wherein the drug unit is an auristatin compound. The Drug units can be covalently linked directly or via a Linker unit (-LU-).

In some embodiments, the antibody-drug conjugate compound has the following formula:

L-(LU-D)$_p$ (I)

or a pharmaceutically acceptable salt or solvate thereof; wherein:

L is the antibody unit, i.e., anti-CD30 antibody (including anti-CD30 antibody fragments), and (LU-D) is a Linker unit-Drug unit moiety, wherein:

LU- is a Linker unit, and

-D is the auristatin compound having cytostatic or cytotoxic activity against a target cell; and p is an integer from 1 to about 20.

In some embodiments, p ranges from 1 to about 10, 1 to about 9, 1 to about 8, 1 to about 7, 1 to about 6, 1 to about 5, 1 to about 4, 1 to about 3, or 1 to about 2. In some embodiments, p ranges from 2 to about 10, 2 to about 9, 2 to about 8, 2 to about 7, 2 to about 6, 2 to about 5, 2 to about 4 or 2 to 3. In other embodiments, p is 1, 2, 3, 4, 5 or 6. In some embodiments, p is 2 or 4.

In some embodiments, the antibody-drug conjugate compound has the following formula:

L-(A$_a$-W$_w$—Y$_y$-D)$_p$ (II)

or a pharmaceutically acceptable salt or solvate thereof; wherein:

L is the antibody unit, i.e., anti-CD30 antibody (including anti-CD30 antibody fragments); and -A$_a$-W$_w$—Y$_y$— is a Linker unit (LU), wherein:
-A- is a Stretcher unit,
a is 0 or 1,
each —W— is independently an Amino Acid unit,
w is an integer ranging from 0 to 12,
—Y— is a self-immolative spacer unit,
y is 0, 1 or 2;
-D is an auristatin compound having cytostatic or cytotoxic activity against the target cell; and
p is an integer from 1 to about 20.

In some embodiments, a is 0 or 1, w is 0 or 1, and y is 0, 1 or 2. In some embodiments, if w is 1 to 12, then y is 1 or 2. In some embodiments, w is 2 to 12 and y is 1 or 2. In some embodiments, w is 0, y is 0, and a is 1. In some embodiments, a is 0 or 1, w is 0 or 1, and y is 0 or 1. In some embodiments, p ranges from 1 to about 10, 1 to about 9, 1 to about 8, 1 to about 7, 1 to about 6, 1 to about 5, 1 to about 4, 1 to about 3, or 1 to 2. In some embodiments, p ranges from 2 to about 8, 2 to about 7, 2 to about 6, 2 to about 5, 2 to about 4 or 2 to 3. In other embodiments, p is 1, 2, 3, 4, 5 or 6. In some embodiments, p is 2 or 4.

The drug loading is represented by p, the average number of drug molecules per antibody in a molecule. Drug loading may range from 1 to 20 drugs (D) per antibody. The average number of drugs per antibody in preparation of conjugation reactions may be characterized by conventional means such as mass spectroscopy, ELISA assay, and HPLC. The quantitative distribution of antibody-drug conjugates in terms of p may also be determined. In some instances, separation, purification, and characterization of homogeneous Antibody-drug-conjugates where p is a certain value from Antibody-drug-Conjugates with other drug loadings may be achieved by means such as reverse phase HPLC or electrophoresis. In exemplary embodiments, p is from 2 to 8.

Each of these units is described in more detail herein.

Linker Units

Typically, the antibody-drug conjugate compounds comprise a linker region between the auristatin compound and the anti-CD30 antibody. A "Linker unit" (LU) is a bifunctional compound that can be used to link a Drug unit and an antibody unit to form an antibody-drug conjugate compound. In some embodiments, the linker is cleavable under intracellular conditions, such that cleavage of the linker releases the auristatin compound from the antibody in the intracellular environment.

For example, in some embodiments, the linker is cleavable by a cleaving agent that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. Typically, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, *Pharm. Therapeutics* 83:67-123). Most typical are peptidyl linkers that are cleavable by enzymes that are present in CD30-expressing cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker). Other such linkers are described, e.g., in U.S. Pat. No. 6,214,345. In specific embodiments, the peptidyl linker cleavable by an intracellular protease is a Val-Cit linker or a Phe-Lys linker (see, e.g., U.S. Pat. No. 6,214,345, which describes the synthesis of doxorubicin with the val-cit linker). One advantage of using intracellular proteolytic release of the therapeutic agent is that the agent is typically attenuated when conjugated and the serum stabilities of the conjugates are typically high.

In other embodiments, the cleavable linker is pH-sensitive, i.e., sensitive to hydrolysis at certain pH values. Typically, the pH-sensitive linker hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, *Pharm. Therapeutics* 83:67-123; Neville et al., 1989, *Biol. Chem.* 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In yet other embodiments, the linker is cleavable under reducing conditions (e.g., a disulfide linker). A variety of disulfide linkers are known in the art, including, for example, those that can be formed using SATA (N-succinimidyl-S-acetylthioacetate), SPDP(N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT. (See, e.g., Thorpe et al., 1987, *Cancer Res.* 47:5924-5931; Wawrzynczak et al., In *Immunoconjugates: Antibody Conjugates in Radioimagery and Therapy of Cancer* (C. W. Vogel ed., Oxford U. Press, 1987. See also U.S. Pat. No. 4,880,935.)

In yet other specific embodiments, the linker is a malonate linker (Johnson et al., 1995, *Anticancer Res.* 15:1387-93), a maleimidobenzoyl linker (Lau et al., 1995, *Bioorg-Med-Chem.* 3(10):1299-1304), or a 3'-N-amide analog (Lau et al., 1995, *Bioorg-Med-Chem.* 3(10):1305-12).

In yet other embodiments, the linker unit is not cleavable and the drug is released by antibody degradation. (See U.S. Publication No. 20050238649 incorporated by reference herein in its entirety and for all purposes).

Typically, the linker is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, no more than about 3%, or no more than about 1% of the linkers, in a sample of antibody-drug conjugate compound, are cleaved when the antibody-drug conjugate compound presents in an extracellular environment (e.g., in plasma). Whether a linker is not substantially sensitive to the extracellular environment can be determined, for example, by incubating with plasma the antibody-drug conjugate compound for a predetermined time period (e.g., 2, 4, 8, 16, or 24 hours) and then quantitating the amount of free drug present in the plasma.

In other, non-mutually exclusive embodiments, the linker promotes cellular internalization. In certain embodiments, the linker promotes cellular internalization when conjugated to the therapeutic agent (i.e., in the milieu of the linker-therapeutic agent moiety of the antibody-drug conjugate compound as described herein). In yet other embodiments, the linker promotes cellular internalization when conjugated to both the auristatin compound and the anti-CD30 antibody.

A variety of linkers that can be used with the present compositions and methods are described in, for example, WO 2004-010957, U.S. Publication No. 20060074008, U.S. Publication No. 20050238649, and U.S. Publication No. 20060024317 (each of which is incorporated by reference herein in its entirety and for all purposes).

In some embodiments, the Linker unit has the formula:

-A$_a$-W$_w$—Y$_y$— wherein:
-A- is a Stretcher unit,
a is 0 or 1,
each —W— is independently an Amino Acid unit,
w is an integer ranging from 0 to 12,
—Y— is a self-immolative Spacer unit, and
y is 0, 1 or 2.

In some embodiments, a is 0 or 1, w is 0 or 1, and y is 0, 1 or 2. In some embodiments, if w is 1 to 12, then y is 1 or 2. In some embodiments, w is 2 to 12 and y is 1 or 2. In some embodiments, a is 0 or 1, w is 0 or 1, and y is 0 or 1. In some embodiments, p ranges from 1 to about 10, 1 to about 9, 1 to about 8, 1 to about 7, 1 to about 6, 1 to about 5, 1 to about 4, 1 to about 3, or 1 to 2. In some embodiments, p ranges from 2 to about 8, 2 to about 7, 2 to about 6, 2 to about 5, 2 to about 4 or 2 to 3. In other embodiments, p is 1, 2, 3, 4, 5 or 6. In some embodiments, p is 2 or 4.

The Stretcher Unit

The Stretcher unit (A), when present, is capable of linking an antibody unit to an Amino Acid unit (—W—), if present, to a Spacer unit (—Y—), if present; or to a Drug unit (-D). Useful functional groups that can be present on an anti-CD30 antibody, either naturally or via chemical manipulation include, but are not limited to, sulfhydryl, amino, hydroxyl, the anomeric hydroxyl group of a carbohydrate, and carboxyl. Suitable functional groups are sulfhydryl and amino. Sulfhydryl groups can be generated by reduction of the intramolecular disulfide bonds of an anti-CD30 antibody. Alternatively, sulfhydryl groups can be generated by reaction of an amino group of a lysine moiety of an anti-CD30 antibody with 2-iminothiolane (Traut's reagent) or other sulfhydryl generating reagents. In certain embodiments, the anti-CD30 antibody is a recombinant antibody and is engineered to carry one or more lysines. In certain other embodiments, the recombinant anti-CD30 antibody is engineered to carry additional sulfhydryl groups, e.g., additional cysteines In some embodiments, the Stretcher unit forms a bond with a sulfur atom of the antibody unit. The sulfur atom can be derived from a sulfhydryl group of an antibody. Representative Stretcher units of this embodiment are depicted within the square brackets of Formulas IIIa and IIIb, wherein L-, —W—, —Y—, -D, w and y are as defined above, and R$_{17}$ is selected from —C$_1$-C$_{10}$ alkylene-, —C$_1$-C$_{10}$ alkenylene-, —C$_1$-C$_{10}$ alkynylene-, -carbocyclo-, —O—(C$_1$-C$_8$ alkylene)-, O—(C$_1$-C$_8$ alkenylene)-, —O—(C$_1$-C$_8$ alkynylene)-, -arylene-, —C$_1$-C$_{10}$ alkylene-arylene-, —C$_2$-C$_{10}$ alkenylene-arylene, —C$_2$-C$_{10}$ alkynylene-arylene, -arylene-C$_1$-C$_{10}$ alkylene-, -arylene-C$_2$-C$_{10}$ alkenylene-,-arylene-C$_2$-C$_{10}$ alkynylene-, —C$_1$-C$_{10}$ alkylene-(carbocyclo)-, —C$_2$-C$_{10}$ alkenylene-(carbocyclo)-, —C$_2$-C$_{10}$ alkynylene-(carbocyclo)-, -(carbocyclo)-C$_1$-C$_{10}$ alkylene-, -(carbocyclo)-, —C$_2$-C$_{10}$ alkenylene-, -(carbocyclo)-C$_2$-C$_{10}$ alkynylene, heterocyclo-, —C$_1$-C$_{10}$ alkylene-(heterocyclo)-, —C$_2$-C$_{10}$ alkenylene-(heterocyclo)-, —C$_2$-C$_{10}$ alkynylene-(heterocyclo)-, -(heterocyclo)-C$_1$-C$_{10}$ alkylene-, -(heterocyclo)-C$_2$-C$_{10}$ alkenylene-, -(heterocyclo)-C$_1$-C$_{10}$ alkynylene-, —(CH$_2$CH$_2$O)$_r$—, or —(CH$_2$CH$_2$O)$_r$—CH$_2$—, and r is an integer ranging from 1-10, wherein said alkyl, alkenyl, alkynyl, alkylene, alkenylene, alkynyklene, aryl, carbocyle, carbocyclo, heterocyclo, and arylene radicals, whether alone or as part of another group, are optionally substituted. Alkylene, alkenylene, alkynylene radicals, whether alone or as part of another group, can be optionally substituted with, for example, one or more groups independently selected from A1; carbocyclo radicals, whether alone or as part of another group, can be optionally substituted with, for example, one or more groups independently selected from A2; arylene radicals, whether alone or as part of another group, can be optionally substituted with, for example, one or more groups independently selected from A3; heterocyclo radicals, whether alone or as part of another group, can be optionally substituted with, for example, one or more groups independently selected from A4. A1, A2, A3, and A4 are as defined herein. It is to be understood from all the exemplary embodiments that even where not denoted expressly, from 1 to 20 drug moieties can be linked to an antibody (p=1-20).

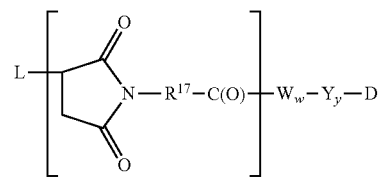

IIIa

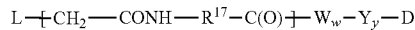

IIIb

An illustrative Stretcher unit is that of Formula IIIa wherein R$^{17}$ is —(CH$_2$)$_5$—:

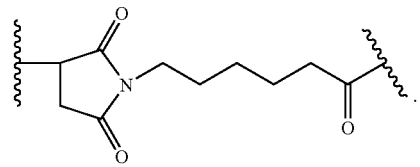

Another illustrative Stretcher unit is that of Formula IIIa wherein R$^{17}$ is —(CH$_2$CH$_2$O)$_r$—CH$_2$—; and r is 2:

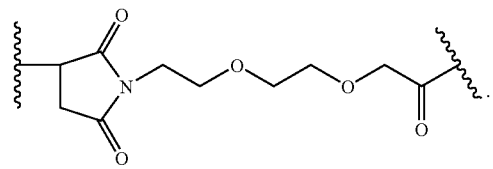

An illustrative Stretcher unit is that of Formula IIIa wherein R$^{17}$ is -arylene- or arylene-C$_1$-C$_{10}$ alkylene-. In some embodiments, the aryl group is an unsubstituted phenyl group.

Still another illustrative Stretcher unit is that of Formula IIIb wherein R$^{17}$ is —(CH$_2$)$_5$—:

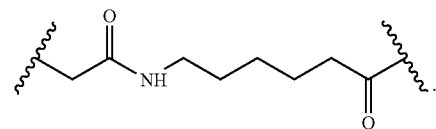

In certain embodiments, the Stretcher unit is linked to the antibody unit via a disulfide bond between a sulfur atom of the antibody unit and a sulfur atom of the Stretcher unit. A representative Stretcher unit of this embodiment is depicted within the square brackets of Formula IV, wherein $R^{17}$, L-, —W—, —Y—, -D, w and y are as defined above.

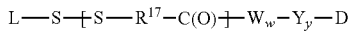
IV

It should be noted that throughout this application, the S moiety in the formula below refers to a sulfur atom of the antibody unit, unless otherwise indicated by context.

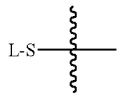

In yet other embodiments, the Stretcher contains a reactive site that can form a bond with a primary or secondary amino group of an antibody. Examples of these reactive sites include, but are not limited to, activated esters such as succinimide esters, 4-nitrophenyl esters, pentafluorophenyl esters, tetrafluorophenyl esters, anhydrides, acid chlorides, sulfonyl chlorides, isocyanates and isothiocyanates. Representative Stretcher units of this embodiment are depicted within the square brackets of Formulas Va and Vb, wherein —$R^{17}$—, L-, —W—, —Y—, -D, w and y are as defined above;

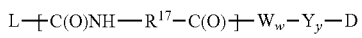
Va

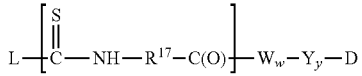
Vb

In some embodiments, the Stretcher contains a reactive site that is reactive to a modified carbohydrate's (—CHO) group that can be present on an antibody. For example, a carbohydrate can be mildly oxidized using a reagent such as sodium periodate and the resulting (—CHO) unit of the oxidized carbohydrate can be condensed with a Stretcher that contains a functionality such as a hydrazide, an oxime, a primary or secondary amine, a hydrazine, a thiosemicarbazone, a hydrazine carboxylate, and an arylhydrazide such as those described by Kaneko et al., 1991, *Bioconjugate Chem.* 2:133-41. Representative Stretcher units of this embodiment are depicted within the square brackets of Formulas VIa, VIb, and VIc, wherein —$R^{17}$—, L-, —W—, —Y—, -D, w and y are as defined

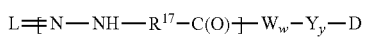
VIa

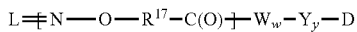
VIb

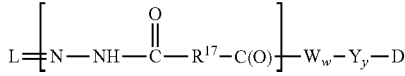
VIc above.

The Amino Acid Unit

The Amino Acid unit (—W—), when present, links the Stretcher unit to the Spacer unit if the Spacer unit is present, links the Stretcher unit to the Drug moiety if the Spacer unit is absent, and links the antibody unit to the Drug unit if the Stretcher unit and Spacer unit are absent.

When present, $W_w$— is a monopeptide dipeptide, tripeptide, tetrapeptide, pentapeptide, hexapeptide, heptapeptide, octapeptide, nonapeptide, decapeptide, undecapeptide or dodecapeptide unit. Each —W— unit independently has the formula denoted below in the square brackets, and w is an integer ranging from 0 to 12:

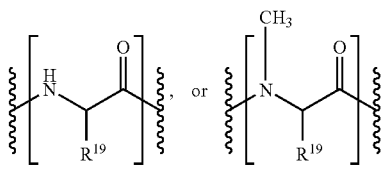

wherein $R^{19}$ is hydrogen, methyl, isopropyl, isobutyl, sec-butyl, benzyl, p-hydroxybenzyl, —$CH_2OH$, —$CH(OH)CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC(=NH)NH_2$, —$(CH_2)_3NH_2$, —$(CH_2)_3NHCOCH_3$, —$(CH_2)_3NHCHO$, —$(CH_2)_4NHC(=NH)NH_2$, —$(CH_2)_4NH_2$, —$(CH_2)_4NHCOCH_3$, —$(CH_2)_4NHCHO$, —$(CH_2)_3NHCONH_2$, —$(CH_2)_4NHCONH_2$, —$CH_2CH_2CH(OH)CH_2NH_2$, 2-pyridylmethyl-, 3-pyridylmethyl-, 4-pyridylmethyl-, phenyl, cyclohexyl,

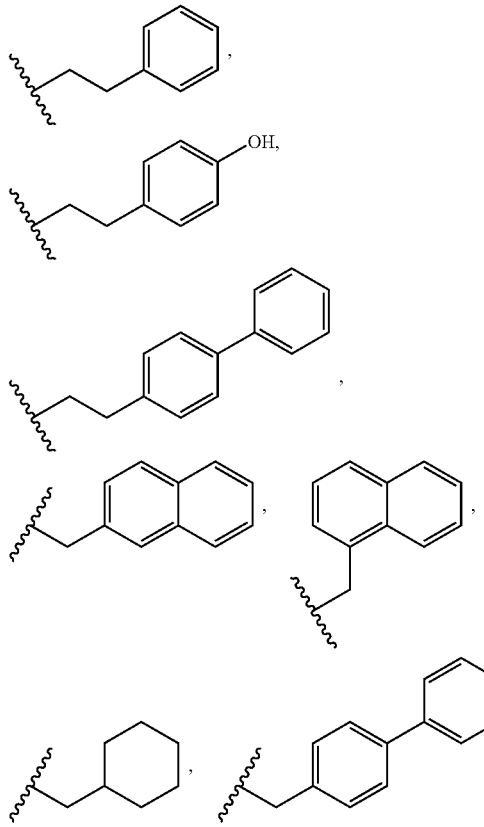

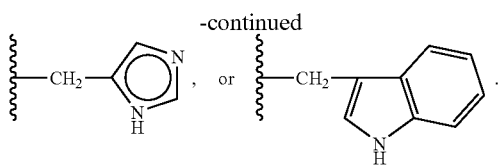

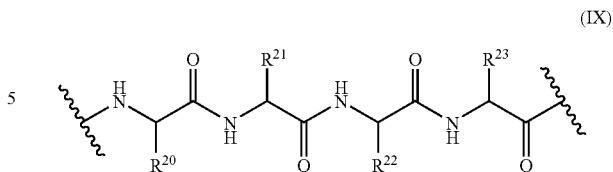

In some embodiments, the Amino Acid unit can be enzymatically cleaved by one or more enzymes, including a cancer or tumor-associated protease, to liberate the Drug unit (-D), which in one embodiment is protonated in vivo upon release to provide a Drug (D).

In certain embodiments, the Amino Acid unit can comprise natural amino acids. In other embodiments, the Amino Acid unit can comprise non-natural amino acids. Illustrative Ww units are represented by formulas (VII)-(IX):

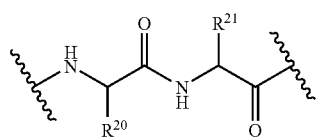

wherein $R^{20}$ and $R^{21}$ are as follows:

| $R^{20}$ | $R^{21}$ |
|---|---|
| Benzyl | $(CH_2)_4NH_2$; |
| methyl | $(CH_2)_4NH_2$; |
| isopropyl | $(CH_2)_4NH_2$; |
| isopropyl | $(CH_2)_3NHCONH_2$; |
| benzyl | $(CH_2)_3NHCONH_2$; |
| isobutyl | $(CH_2)_3NHCONH_2$; |
| sec-butyl | $(CH_2)_3NHCONH_2$; |
| 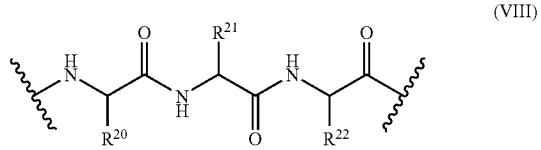 | $(CH_2)_3NHCONH_2$; |
| benzyl | methyl; |
| benzyl | $(CH_2)_3NHC(=NH)NH_2$; |

(VIII)

wherein $R^{20}$, $R^{21}$ and $R^{22}$ are as follows:

| $R^{20}$ | $R^{21}$ | $R^{22}$ |
|---|---|---|
| benzyl | benzyl | $(CH_2)_4NH_2$; |
| isopropyl | benzyl | $(CH_2)_4NH_2$; and |
| H | benzyl | $(CH_2)_4NH_2$; |

(IX)

wherein $R^{20}$, $R^{21}$, $R^{22}$ and $R^{23}$ are as follows:

| $R^{20}$ | $R^{21}$ | $R^{22}$ | $R^{23}$ |
|---|---|---|---|
| H | benzyl | isobutyl | H; and |
| methyl | isobutyl | methyl | isobutyl. |

Exemplary Amino Acid units include, but are not limited to, units of formula VII where: $R^{20}$ is benzyl and $R^{21}$ is —$(CH_2)_4NH_2$; $R^{20}$ is isopropyl and $R^{21}$ is —$(CH_2)_4NH_2$; or $R^{20}$ is isopropyl and $R^{21}$ is —$(CH_2)_3NHCONH_2$. Another exemplary Amino Acid unit is a unit of formula VIII wherein $R^{20}$ is benzyl, $R^{21}$ is benzyl, and $R^{22}$ is —$(CH_2)_4NH_2$.

Useful —$W_w$— units can be designed and optimized in their selectivity for enzymatic cleavage by a particular enzyme, for example, a tumor-associated protease. In one embodiment, a —$W_w$— unit is that whose cleavage is catalyzed by cathepsin B, C and D, or a plasmin protease.

In one embodiment, —$W_w$— is a dipeptide, tripeptide, tetrapeptide or pentapeptide. When $R^{19}$, $R^{20}$, $R^{21}$, $R^{22}$ or $R^{23}$ is other than hydrogen, the carbon atom to which $R^{19}$, $R^{20}$, $R^{21}$, $R^{22}$ or $R^{23}$ is attached is chiral.

Each carbon atom to which $R^{19}$, $R^{20}$, $R^{21}$, $R^{22}$ or $R^{23}$ is attached is independently in the (S) or (R) configuration.

In one aspect of the Amino Acid unit, the Amino Acid unit is valine-citrulline (i.e., vc or val-cit). In another aspect, the Amino Acid unit is phenylalanine-lysine (i.e., fk). In yet another aspect of the Amino Acid unit, the Amino Acid unit is N-methylvaline-citrulline. In yet another aspect, the Amino Acid unit is 5-aminovaleric acid, homo phenylalanine lysine, tetraisoquinolinecarboxylate lysine, cyclohexylalanine lysine, isonepecotic acid lysine, beta-alanine lysine, glycine serine valine glutamine and isonepecotic acid.

The Spacer Unit

The Spacer unit (—Y—), when present, links an Amino Acid unit to the Drug unit when an Amino Acid unit is present. Alternately, the Spacer unit links the Stretcher unit to the Drug unit when the Amino Acid unit is absent. The Spacer unit also links the Drug unit to the antibody unit when both the Amino Acid unit and Stretcher unit are absent.

Spacer units are of two general types: non self-immolative or self-immolative. A non self-immolative Spacer unit is one in which part or all of the Spacer unit remains bound to the Drug moiety after cleavage, particularly enzymatic, of an Amino Acid unit from the antibody drug conjugate. Examples of a non self-immolative Spacer unit include, but are not limited to a (glycine-glycine) Spacer unit and a glycine Spacer unit (both depicted in Scheme 1) (infra). When a conjugate containing a glycine-glycine Spacer unit or a glycine Spacer unit undergoes enzymatic cleavage via an enzyme (e.g., a tumor-cell associated-protease, a cancer-cell-associated protease or a lymphocyte-associated protease), a glycine-glycine-Drug moiety or a glycine-Drug moiety is cleaved from L-Aa-Ww-. In one embodiment, an independent hydrolysis reaction takes place within the target cell, cleaving the glycine-Drug moiety bond and liberating the Drug.

Scheme 1

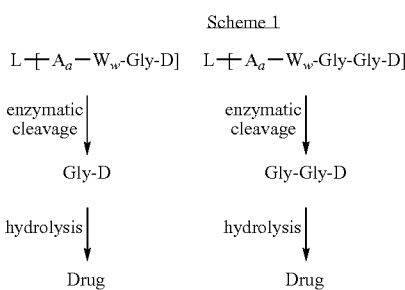

In some embodiments, a non self-immolative Spacer unit (—Y—) is -Gly-. In some embodiments, a non self-immolative Spacer unit (—Y—) is -Gly-Gly-.

In one embodiment, a Drug-Linker conjugate is provided in which the Spacer unit is absent (y=0), or a pharmaceutically acceptable salt or solvate thereof.

Alternatively, a conjugate containing a self-immolative Spacer unit can release -D. As used herein, the term "self-immolative Spacer" refers to a bifunctional chemical moiety that is capable of covalently linking together two spaced chemical moieties into a stable tripartite molecule. It will spontaneously separate from the second chemical moiety if its bond to the first moiety is cleaved.

In some embodiments, —$Y_y$— is a p-aminobenzyl alcohol (PAB) unit (see Schemes 2 and 3) whose phenylene portion is substituted with $Q_m$ wherein Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; and m is an integer ranging from 0-4.

In some embodiments, —Y— is a PAB group that is linked to —$W_w$— via the amino nitrogen atom of the PAB group, and connected directly to -D via a carbonate, carbamate or ether group. Without being bound by any particular theory or mechanism, Scheme 2 depicts a possible mechanism of Drug release of a PAB group which is attached directly to -D via a carbamate or carbonate group as described by Told et al., 2002, *J. Org. Chem.* 67:1866-1872.

Scheme 2

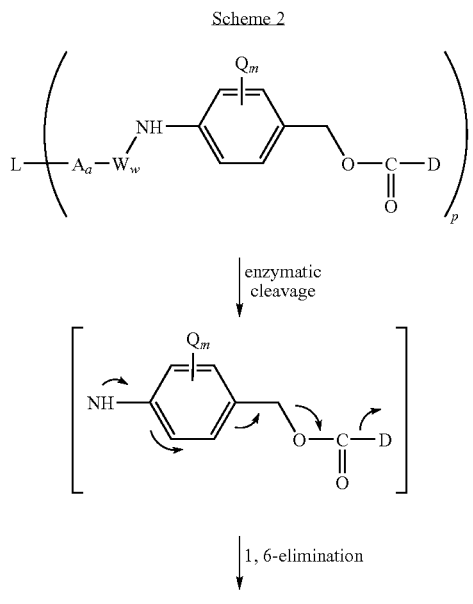

In Scheme 2, Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; m is an integer ranging from 0-4; and p ranges from 1 to about 20.

Without being bound by any particular theory or mechanism, Scheme 3 depicts a possible mechanism of Drug release of a PAB group which is attached directly to -D via an ether or amine linkage, wherein D includes the oxygen or nitrogen group that is part of the Drug unit.

Scheme 3

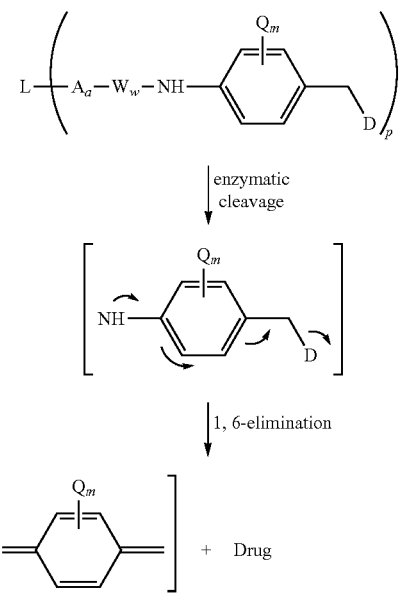

In Scheme 3, Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; m is an integer ranging from 0-4; and p ranges from 1 to about 20.

Other examples of self-immolative spacers include, but are not limited to, aromatic compounds that are electronically similar to the PAB group such as 2-aminoimidazol-5-methanol derivatives (Hay et al., 1999, *Bioorg. Med. Chem. Lett.* 9:2237) and ortho or para-aminobenzylacetals. Spacers can be used that undergo cyclization upon amide bond hydrolysis, such as substituted and unsubstituted 4-aminobutyric acid amides (Rodrigues et al., 1995, *Chemistry Biology* 2:223), appropriately substituted bicyclo[2.2.1] and bicyclo[2.2.2] ring systems (Storm et al., 1972, *J. Amer. Chem. Soc.* 94:5815) and 2-aminophenylpropionic acid amides (Amsberry et al., 1990, *J. Org. Chem.* 55:5867). Elimination of amine-containing drugs that are substituted at the α-position of glycine (Kingsbury et al., 1984, *J. Med. Chem.* 27:1447) are also examples of self-immolative spacers.

In one embodiment, the Spacer unit is a branched bis (hydroxymethyl)-styrene (BHMS) unit as depicted in Scheme 4, which can be used to incorporate and release multiple drugs.

Scheme 4

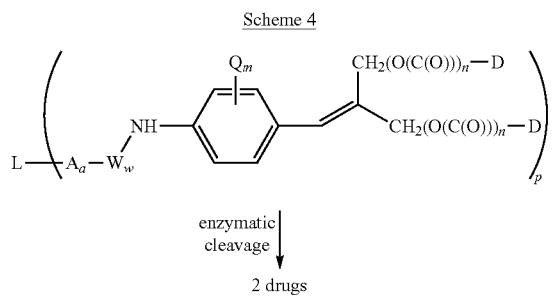

In Scheme 4, Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; m is an integer ranging from 0-4; n is 0 or 1; and p ranges raging from 1 to about 20.

In some embodiments, the -D moieties are the same. In yet another embodiment, the -D moieties are different.

In one aspect, Spacer units (—$Y_y$—) are represented by Formulas (X)-(XII):

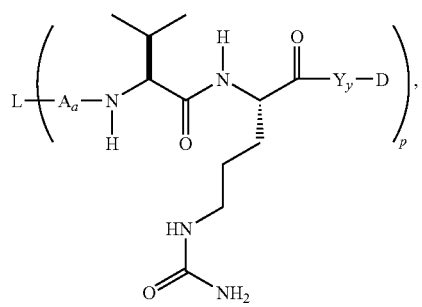

X wherein Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; and m is an integer ranging from 0-4;

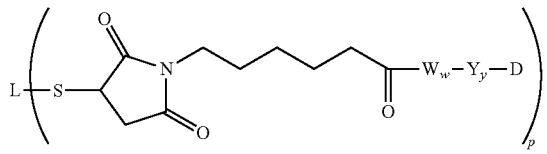

XI

XII

Embodiments of the Formula I and II comprising Antibody-drug conjugate compounds can include:

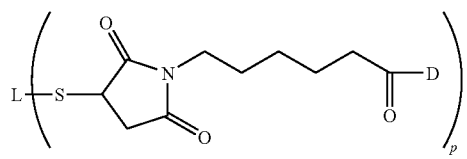

wherein w and y are each 0, 1 or 2, and,

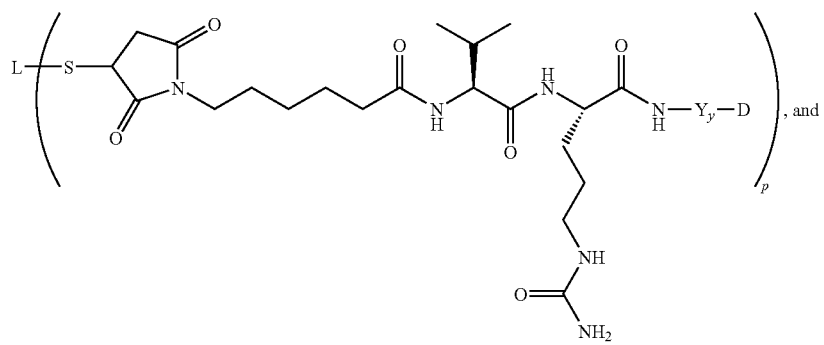

wherein w and y are each 0,

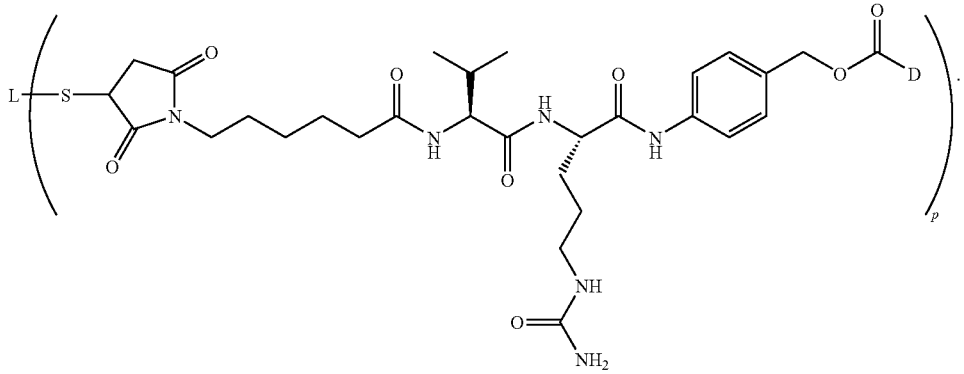

The Drug Unit

D is an auristatin drug compound having an atom that can form a bond with the Spacer unit, with the Amino Acid unit, with the Stretcher unit or with the antibody unit. In some embodiments, the Drug unit D has a N-terminal nitrogen atom that can form a bond with the Spacer unit. As used herein, the terms "Drug unit" and "Drug moiety" are synonymous and used interchangeably and refer to an auristatin drug unit or moiety.

In certain preferred embodiments, the auristatin drug unit is auristatin E or a derivative thereof. Accordingly, the term "auristatin" as used herein is meant to include auristatin derivatives. The synthesis and structure of exemplary auristatin derivatives are described in U.S. Patent Application Publication Nos. 2003-0083263, 2005-0238649 and 2005-0009751; International Patent Publication No. WO 04/010957, International Patent Publication No. WO 02/088172, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414, each of which is incorporated by reference herein in its entirety.

In some embodiments, -D is an auristatin of the formula $D_E$ or $D_F$:

$R^2$ is —$C_1$-$C_{20}$ alkyl, —$C_2$-$C_{20}$ alkenyl, or —$C_2$-$C_{20}$ alkynyl;

$R^3$ is —H, —$C_1$-$C_{20}$ alkyl, —$C_2$-$C_{20}$ alkenyl, —$C_2$-$C_{20}$ alkynyl, carbocycle, —$C_1$-$C_{20}$ alkylene (carbocycle), —$C_2$-$C_{20}$ alkenylene(carbocycle), —$C_2$-$C_{20}$ alkynylene(carbocycle), -aryl, —$C_1$-$C_{20}$ alkylene(aryl), —$C_2$-$C_{20}$ alkenylene(aryl), —$C_2$-$C_{20}$ alkynylene(aryl), -heterocycle, —$C_1$-$C_{20}$ alkylene(heterocycle), —$C_2$-$C_{20}$ alkenylene(heterocycle), or —$C_2$-$C_{20}$ alkynylene(heterocycle);

$R^4$ is —H, —$C_1$-$C_{20}$ alkyl, —$C_2$-$C_{20}$ alkenyl, —$C_2$-$C_{20}$ alkynyl, carbocycle, —$C_1$-$C_{20}$ alkylene (carbocycle), —$C_2$-$C_{20}$ alkenylene(carbocycle), —$C_2$-$C_{20}$ alkynylene(carbocycle), -aryl, —$C_1$-$C_{20}$ alkylene(aryl), —$C_2$-$C_{20}$ alkenylene(aryl), —$C_2$-$C_{20}$ alkynylene(aryl), -heterocycle, —$C_1$-$C_{20}$ alkylene(heterocycle), —$C_2$-$C_{20}$ alkenylene(heterocycle), or —$C_2$-$C_{20}$ alkynylene(heterocycle);

$R^5$ is —H or —$C_1$-$C_8$ alkyl;

or $R^4$ and $R^5$ jointly form a carbocyclic ring and have the formula —$(CR^aR^b)_s$— wherein $R^a$ and $R^b$ are independently —H, —$C_1$-$C_{20}$ alkyl, —$C_2$-$C_{20}$ alkenyl, —$C_2$-$C_{20}$ alkynyl, or carbocycle and s is 2, 3, 4, 5 or 6, $R^6$ is —H, —$C_1$-$C_{20}$ alkyl, —$C_2$-$C_{20}$ alkenyl, or —$C_2$-$C_{20}$ alkynyl;

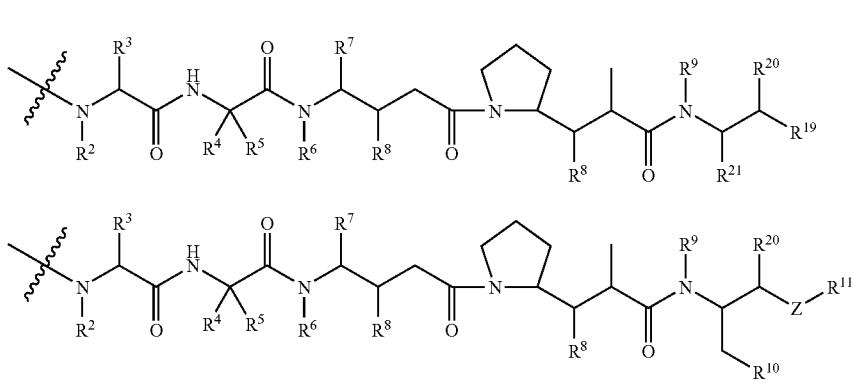

or a pharmaceutically acceptable salt or solvate form thereof; wherein, independently at each location:
the wavy line indicates a bond;

$R^7$ is —H, —$C_1$-$C_{20}$ alkyl, —$C_2$-$C_{20}$ alkenyl, —$C_2$-$C_{20}$ alkynyl, -carbocycle, —$C_1$-$C_{20}$ alkylene (carbocycle), —$C_2$-$C_{20}$ alkenylene(carbocycle), —$C_2$-$C_{20}$ alkynylene(carbocycle), aryl, —$C_1$-$C_{20}$ alkylene(aryl), —$C_2$-$C_{20}$ alkenylene (aryl), —$C_2$-$C_{20}$ alkynylene(aryl), heterocycle, —$C_1$-$C_{20}$ alkylene(heterocycle), —$C_2$-$C_{20}$ alkenylene(heterocycle), or —$C_2$-$C_{20}$ alkynylene(heterocycle);

each $R^8$ is independently —H, —OH, —$C_1$-$C_{20}$ alkyl, —$C_2$-$C_{20}$ alkenyl, —$C_2$-$C_{20}$ alkynyl, —O—($C_1$-$C_{20}$ alkyl), —O—($C_2$-$C_{20}$ alkenyl), —O—($C_1$-$C_{20}$ alkynyl), or -carbocycle;

$R^9$ is —H, —$C_1$-$C_{20}$ alkyl, —$C_2$-$C_{20}$ alkenyl, or —$C_2$-$C_{20}$ alkynyl;

$R^{19}$ is -aryl, -heterocycle, or -carbocycle;

$R^{20}$ is —H, —$C_1$-$C_{20}$ alkyl, —$C_2$-$C_{20}$ alkenyl, —$C_2$-$C_{20}$ alkynyl, -carbocycle, —O—($C_1$-$C_{20}$ alkyl), —O—($C_2$-$C_{20}$ alkenyl), —O—($C_2$-$C_{20}$ alkynyl), or $OR^{18}$ wherein $R^{18}$ is —H, a hydroxyl protecting group, or a direct bond where $OR^{18}$ represents =O;

$R^{21}$ is —H, —$C_1$-$C_{20}$ alkyl, —$C_2$-$C_{20}$ alkenyl, or —$C_2$-$C_{20}$ alkynyl, -aryl, -heterocycle, or -carbocycle;

$R^{10}$ is -aryl or -heterocycle;

Z is —O—, —S—, —NH—, or —$NR^{12}$—, wherein $R^{12}$ is —$C_1$-$C_{20}$ alkyl, —$C_2$-$C_{20}$ alkenyl, or —$C_2$-$C_{20}$ alkynyl;

$R^{11}$ is —H, —$C_1$-$C_{20}$ alkyl, —$C_2$-$C_{20}$ alkenyl, —$C_2$-$C_{20}$ alkynyl, -aryl, -heterocycle, —($R^{13}O)_m$—$R^{14}$, or —($R^{13}O)_m$—$CH(R^{15})_2$;

m is an integer ranging from 1-1000;

$R^{13}$ is —$C_2$-$C_{20}$ alkylene, —$C_2$-$C_{20}$ alkenylene, or —$C_2$-$C_{20}$ alkynylene;

$R^{14}$ is —H, —$C_1$-$C_{20}$ alkyl, —$C_2$-$C_{20}$ alkenyl, or —$C_2$-$C_{20}$ alkynyl;

each occurrence of $R^{15}$ is independently —H, —COOH, —$(CH_2)_n$—$N(R^{16})_2$, —$(CH_2)_n$—$SO_3H$, —$(CH_2)_n$—$SO_3$—$C_1$-$C_{20}$ alkyl, —$(CH_2)_n$—$SO_3$—$C_2$-$C_{20}$ alkenyl, or —$(CH_2)_n$—$SO_3$—$C_2$-$C_{20}$ alkynyl;

each occurrence of $R^{16}$ is independently —H, —$C_1$-$C_{20}$ alkyl, —$C_2$-$C_{20}$ alkenyl, —$C_2$-$C_{20}$ alkynyl or —$(CH_2)_n$—COOH; and n is an integer ranging from 0 to 6; wherein said alkyl, alkenyl, alkynyl, alkylene, alkenylene, alkynyklene, aryl, carbocyle, and heterocycle radicals, whether alone or as part of another group, are optionally substituted.

Auristatins of the formula $D_E$ or $D_F$ include those wherein $R^2$ is —$C_1$-$C_{20}$ alkyl, —$C_2$-$C_{20}$ alkenyl, or —$C_2$-$C_{20}$ alkynyl, each of which is optionally substituted with one or more groups independently selected from A1;

$R^3$ is —H, —$C_1$-$C_{20}$ alkyl, —$C_2$-$C_{20}$ alkenyl, —$C_2$-$C_{20}$ alkynyl, monocyclic $C_3$-$C_6$ carbocycle, —$C_1$-$C_{20}$ alkylene (monocyclic $C_3$-$C_6$ carbocycle), —$C_2$-$C_{20}$ alkenylene(monocyclic $C_3$-$C_6$ carbocycle), —$C_2$-$C_{20}$ alkynylene(monocyclic $C_3$-$C_6$ carbocycle), —$C_6$-$C_{10}$ aryl, —$C_1$-$C_{20}$ alkylene($C_6$-$C_{10}$ aryl), —$C_2$-$C_{20}$ alkenylene($C_6$-$C_{10}$ aryl), —$C_2$-$C_{20}$ alkynylene($C_6$-$C_{10}$ aryl), -heterocycle, —$C_1$-$C_{20}$ alkylene(heterocycle), —$C_2$-$C_{20}$ alkenylene(heterocycle), or —$C_2$-$C_{20}$ alkynylene(heterocycle); wherein said alkyl, alkenyl, alkynyl, alkylene, alkenylene, and alkynylene radicals whether alone or as part of another group are optionally substituted with one or more groups independently selected from A1, said carbocycle radicals whether alone or as part of another group are optionally substituted with one or more groups independently selected from A2, said aryl radicals whether alone or as part of another group are optionally substituted with one or more groups independently selected from A3, and said heterocycle radicals whether alone or as part of another group are optionally substituted with one or more groups independently selected from A4;

$R^4$ is —H, —$C_1$-$C_{20}$ alkyl, —$C_2$-$C_{20}$ alkenyl, —$C_2$-$C_{20}$ alkynyl, monocyclic $C_3$-$C_6$ carbocycle, —$C_1$-$C_{20}$ alkylene (monocyclic $C_3$-$C_6$ carbocycle), —$C_2$-$C_{20}$ alkenylene(monocyclic $C_3$-$C_6$ carbocycle), —$C_2$-$C_{20}$ alkynylene(monocyclic $C_3$-$C_6$ carbocycle), —$C_6$-$C_{10}$ aryl, —$C_1$-$C_{20}$ alkylene($C_6$-$C_{10}$ aryl), —$C_2$-$C_{20}$ alkenylene($C_6$-$C_{10}$ aryl), —$C_2$-$C_{20}$ alkynylene($C_6$-$C_{10}$ aryl), -heterocycle, —$C_1$-$C_{20}$ alkylene(heterocycle), —$C_2$-$C_{20}$ alkenylene(heterocycle), or —$C_2$-$C_{20}$ alkynylene(heterocycle); wherein said alkyl, alkenyl, alkynyl, alkylene, alkenylene, and alkynylene radicals whether alone or as part of another group are optionally substituted with one or more groups independently selected from A1, said carbocycle radicals whether alone or as part of another group are optionally substituted with one or more groups independently selected from A2, said aryl radicals whether alone or as part of another group are optionally substituted with one or more groups independently selected from A3, and said heterocycle radicals whether alone or as part of another group are optionally substituted with one or more groups independently selected from A4;

$R^5$ is —H or —$C_1$-$C_8$ alkyl;

or $R^4$ and $R^5$ jointly form a carbocyclic ring and have the formula —$(CR^aR^b)_s$— wherein $R^a$ and $R^b$ are independently —H, —$C_1$-$C_8$ alkyl, —$C_2$-$C_8$ alkenyl, —$C_2$-$C_8$ alkynyl, or carbocycle, and s is 2, 3, 4, 5 or 6;

$R^6$ is —H, —$C_1$-$C_{20}$ alkyl, —$C_2$-$C_{20}$ alkenyl, or —$C_2$-$C_{20}$ alkynyl, wherein said alkyl, alkenyl and alkynyl radicals are optionally substituted with one or more groups independently selected from A1;

$R^7$ is —H, —$C_1$-$C_{20}$ alkyl, —$C_2$-$C_{20}$ alkenyl, —$C_2$-$C_{20}$ alkynyl, monocyclic $C_3$-$C_6$ carbocycle, —$C_1$-$C_{20}$ alkylene (monocyclic $C_3$-$C_6$ carbocycle), —$C_2$-$C_{20}$ alkenylene(monocyclic $C_3$-$C_6$ carbocycle), —$C_2$-$C_{20}$ alkynylene(monocyclic $C_3$-$C_6$ carbocycle), —$C_6$-$C_{10}$ aryl, —$C_1$-$C_{20}$ alkylene($C_6$-$C_{10}$ aryl), —$C_2$-$C_{20}$ alkenylene($C_6$-$C_{10}$ aryl), —$C_2$-$C_{20}$ alkynylene($C_6$-$C_{10}$ aryl), -heterocycle, —$C_1$-$C_{20}$ alkylene(heterocycle), —$C_2$-$C_{20}$ alkenylene(heterocycle), or —$C_2$-$C_{20}$ alkynylene(heterocycle); wherein said alkyl, alkenyl, alkynyl, alkylene, alkenylene, and alkynylene radicals whether alone or as part of another group are optionally substituted with one or more groups independently selected from A1, said carbocycle radicals whether alone or as part of another group are optionally substituted with one or more groups independently selected from A2, said aryl radicals whether alone or as part of another group are optionally substituted with one or more groups independently selected from A3, and said heterocycle radicals whether alone or as part of another group are optionally substituted with one or more groups independently selected from A4;

each $R^8$ is independently —H, —OH, —$C_1$-$C_{20}$ alkyl, —$C_2$-$C_{20}$ alkenyl, —$C_2$-$C_{20}$ alkynyl, —O—($C_1$-$C_{20}$ alkyl), —O—($C_2$-$C_{20}$ alkenyl), —O—($C_1$-$C_{20}$ alkynyl), or -carbocycle, wherein said alkyl, alkenyl, and alkynyl radicals, whether alone or as part of another group, are optionally substituted with one or more groups independently selected from A1 and said carbocycle is optionally substituted with one or more groups independently selected from A2;

$R^9$ is —H, —$C_1$-$C_{20}$ alkyl, —$C_2$-$C_{20}$ alkenyl, or —$C_2$-$C_{20}$ alkynyl; wherein said alkyl, alkenyl and alkynyl radical are optionally substituted with one or more groups independently selected from A1;

$R^{19}$ is -aryl, -heterocycle, or -carbocycle; wherein said carbocycle radical is optionally substituted with one or more groups independently selected from A2, said aryl radical is optionally substituted with one or more groups independently selected from A3, and said heterocycle radical is optionally substituted with one or more groups independently selected from A4;

$R^{20}$ is selected from —H, —$C_1$-$C_{20}$ alkyl, —$C_2$-$C_{20}$ alkenyl, —$C_2$-$C_{20}$ alkynyl, -carbocycle, —OH, —O—($C_1$-$C_{20}$ alkyl), —O—($C_2$-$C_{20}$ alkenyl), —O—($C_2$-$C_{20}$ alkynyl) or $OR^{18}$; wherein said alkyl, alkenyl, and alkynyl radicals, whether alone or as part of another group, are optionally substituted with one or more groups independently selected from A1, and said carbocycle is optionally substituted with one or more groups independently selected from A2;

$R^{18}$ is —H, a hydroxyl protecting group, or a direct bond where $OR^{18}$ represents =O;

$R^{21}$ is selected from —H, —$C_1$-$C_{20}$ alkyl, —$C_2$-$C_{20}$ alkenyl, —$C_2$-$C_{20}$ alkynyl, or -carbocycle; wherein said alkyl, alkenyl, and alkynyl radicals are optionally substituted with one or more groups independently selected from A1, and said carbocycle radical is optionally substituted with one or more groups independently selected from A2;

$R^{10}$ is aryl optionally substituted with one or more groups independently selected from A3, or heterocycle optionally substituted with one or more groups independently selected from A4;

Z is —O—, —S—, —NH—, or —$NR^{12}$, wherein $R^{12}$ is —$C_1$-$C_{20}$ alkyl, —$C_2$-$C_{20}$ alkenyl, or —$C_2$-$C_{20}$ alkynyl, each of which is optionally substituted with one or more groups independently selected from A1;

$R^{11}$ is —H, —$C_1$-$C_{20}$ alkyl, —$C_2$-$C_{20}$ alkenyl, —$C_2$-$C_{20}$ alkynyl, -aryl, -heterocycle, —$(R^{13}O)_m$—$R^{14}$, or —$(R^{13}O)_m$—$CH(R^{15})_2$ wherein said alkyl, alkenyl and alkynyl radicals are optionally substituted with one or more groups independently selected from A1, said aryl radical is optionally substituted with one or more groups independently selected from A3, and said heterocycle is optionally substituted with one or more groups independently selected from A4;

m is an integer ranging from 1-1000;

$R^{13}$ is —$C_2$-$C_{20}$ alkylene, —$C_2$-$C_{20}$ alkenylene, or —$C_2$-$C_{20}$ alkynylene, each of which is optionally substituted with one or more groups independently selected from A1;

$R^{14}$ is —H, —$C_1$-$C_{20}$ alkyl, —$C_2$-$C_{20}$ alkenyl, or —$C_2$-$C_{20}$ alkynyl wherein said alkyl, alkenyl and alkynyl radicals are optionally substituted with one or more groups independently selected from A1;

each occurrence of $R^{15}$ is independently —H, —COOH, —$(CH_2)_n$—$N(R^{16})_2$, —$(CH_2)_n$—$SO_3H$, —$(CH_2)_n$—$SO_3$—$C_1$-$C_{20}$ alkyl, —$(CH_2)_n$—$SO_3$—$C_2$-$C_{20}$ alkenyl, or —$(CH_2)_n$—$SO_3$—$C_2$-$C_{20}$ alkynyl wherein said alkyl, alkenyl and alkynyl radicals are optionally substituted with one or more groups independently selected from A1;

each occurrence of $R^{16}$ is independently —H, —$C_1$-$C_{20}$ alkyl, —$C_2$-$C_{20}$ alkenyl, —$C_2$-$C_{20}$ alkynyl or —$(CH_2)_n$—COOH wherein said alkyl, alkenyl and alkynyl radicals are optionally substituted with one or more groups independently selected from A1;

n is an integer ranging from 0 to 6;

A1 is halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)$NH_2$, —C(O)NHR', —C(O)N(R')$_2$—NHC(O)R', —SR', —$SO_3$R', —S(O)$_2$R', —S(O)R', —OH, =O, —$N_3$, —$NH_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl, and wherein said —O—($C_1$-$C_8$ alkyl), —O—($C_2$-$C_8$ alkenyl), —O—($C_2$-$C_8$ alkynyl), -aryl, —$C_1$-$C_8$ alkyl, —$C_2$-$C_8$ alkenyl, and —$C_2$-$C_8$ alkynyl groups can be optionally further substituted with one or more groups independently selected from —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)$NH_2$, —C(O)NHR", —C(O)N(R")$_2$, —NHC(O)R", —SR", —$SO_3$R", —S(O)$_2$R", —S(O)R", —OH, —$N_3$, —$NH_2$, —NH(R"), —N(R")$_2$ and —CN, where each R" is independently selected from —H, —$C_1$-$C_8$ alkyl, —$C_2$-$C_8$ alkenyl, —$C_2$-$C_8$ alkynyl, or -aryl;

A2 is -halogen, —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)$NH_2$, —C(O)NHR', —C(O)N(R')$_2$—NHC(O)R', —SR', —$SO_3$R', —S(O)$_2$R', —S(O)R', —OH, =O, —$N_3$, —$NH_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl and wherein said —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), and -aryl groups can be further optionally substituted with one or more substituents independently selected from —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)$NH_2$, —C(O)NHR", —C(O)N(R")$_2$, —NHC(O)R", —SR", —$SO_3$R", —S(O)$_2$R", —S(O)R", —OH, —$N_3$, —$NH_2$, —NH(R"), —N(R")$_2$ and —CN, where each R" is independently selected from —H, —$C_1$-$C_8$ alkyl, —$C_2$-$C_8$ alkenyl, —$C_2$-$C_8$ alkynyl, or -aryl;

A3 is -halogen, —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)$NH_2$, —C(O)NHR', —C(O)N(R')$_2$—NHC(O)R', —SR', —$SO_3$R', —S(O)$_2$R', —S(O)R', —OH, —$NO_2$, —$N_3$, —$NH_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl and wherein said —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), and -aryl groups can be further optionally substituted with one or more substituents independently selected from —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)$NH_2$, —C(O)NHR", —C(O)N(R")$_2$, —NHC(O)R", —SR", —$SO_3$R", —S(O)$_2$R", —S(O)R", —OH, —$N_3$, —$NH_2$, —NH(R"), —N(R")$_2$ and —CN, where each R" is independently selected from —H, —$C_1$-$C_8$ alkyl, —$C_2$-$C_8$ alkenyl, —$C_2$-$C_8$ alkynyl, or aryl;

and A4 is —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)$NH_2$, —C(O)NHR', —C(O)N(R')$_2$—NHC(O)R', —SR', —$SO_3$R', —S(O)$_2$R', —S(O)R', —OH, —$N_3$, —$NH_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl and wherein said —O—($C_1$-$C_8$ alkyl), —O—($C_2$-$C_8$ alkenyl), —O—($C_2$-$C_8$ alkynyl), —$C_1$-$C_8$ alkyl, —$C_2$-$C_8$ alkenyl, —$C_2$-$C_8$ alkynyl, and aryl groups can be further optionally substituted with one or more substituents independently selected from —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)$NH_2$, —C(O)NHR", —C(O)N(R")$_2$, —NHC(O)R", —SR", —$SO_3$R", —S(O)$_2$R", —S(O)R", —OH, —$N_3$, —$NH_2$, —NH(R"), —N(R")$_2$ and —CN, where each R" is independently selected from —H, —$C_1$-$C_8$ alkyl, —$C_2$-$C_8$ alkenyl, —$C_2$-$C_8$ alkynyl, or aryl; or a pharmaceutically acceptable salt or solvate form thereof.

Auristatins of the formula $D_E$ include those wherein said alkyl, alkenyl, alkynyl, alkylene, alkenylene, alkynyklene, aryl, carbocyle, and heterocycle radicals are unsubstituted.

Auristatins of the formula $D_E$ include those wherein the groups of $R^2$, $R^3$, $R^4$, $R^5$, $R^6$, $R^7$, $R^8$, and $R^9$ are unsubstituted and the groups of $R^{19}$, $R^{20}$ and $R^{21}$ are optionally substituted as described herein.

Auristatins of the formula $D_E$ include those wherein $R^2$ is $C_1$-$C_{20}$ alkyl optionally substituted with one or more groups independently selected from A1;

$R^3$ and $R^7$ are independently selected from —H, —$C_1$-$C_{20}$ alkyl, —$C_2$-$C_{20}$ alkenyl, —$C_2$-$C_{20}$ alkynyl, monocyclic $C_3$-$C_6$ carbocycle, —$C_1$-$C_{20}$ alkylene(monocyclic $C_3$-$C_6$ carbocycle), —$C_2$-$C_{20}$ alkenylene(monocyclic $C_3$-$C_6$ carbocycle), —$C_2$-$C_{20}$ alkynylene(monocyclic $C_3$-$C_6$ carbocycle), —$C_6$-$C_{10}$ aryl, —$C_1$-$C_{20}$ alkylene($C_6$-$C_{10}$ aryl), —$C_2$-$C_{20}$ alkenylene($C_6$-$C_{10}$ aryl), —$C_2$-$C_{20}$ alkynylene($C_6$-$C_{10}$ aryl), -heterocycle, $C_1$-$C_{20}$ alkylene(heterocycle), —$C_2$-$C_{20}$ alkenylene(heterocycle), or —$C_2$-$C_{20}$ alkynylene(heterocycle); wherein said alkyl, alkenyl, alkynyl, alkylene, alkenylene, and alkynylene radicals whether alone or as part of another group are optionally substituted with one or more groups independently selected from A1, said carbocycle radicals whether alone or as part of another group are optionally substituted with one or more groups independently selected from A2, said aryl radicals whether alone or as part of another group are optionally substituted with one or more groups independently selected from A3, and said heterocycle radicals whether alone or as part of another group are optionally substituted with one or more groups independently selected from A4;

$R^4$ is —H, —$C_1$-$C_{20}$ alkyl, —$C_2$-$C_{20}$ alkenyl, —$C_2$-$C_{20}$ alkynyl, monocyclic $C_3$-$C_6$ carbocycle, —$C_1$-$C_{20}$ alkylene (monocyclic $C_3$-$C_6$ carbocycle), —$C_2$-$C_{20}$ alkenylene(monocyclic $C_3$-$C_6$ carbocycle), —$C_2$-$C_{20}$ alkynylene(monocyclic $C_3$-$C_6$ carbocycle), —$C_6$-$C_{10}$ aryl, —$C_1$-$C_{20}$ alkylene($C_6$-$C_{10}$ aryl), —$C_2$-$C_{20}$ alkenylene($C_6$-$C_{10}$ aryl), —$C_2$-$C_{20}$ alkynylene($C_6$-$C_{10}$ aryl), -heterocycle, —$C_1$-$C_{20}$ alkylene(heterocycle), —$C_2$-$C_{20}$ alkenylene(heterocycle), or —$C_2$-$C_{20}$ alkynylene(heterocycle); wherein said alkyl, alkenyl, alkynyl, alkylene, alkenylene, and alkynylene radicals whether alone or as part of another group are optionally substituted with one or more groups independently selected from A1, said carbocycle radicals whether alone or as part of another group are optionally substituted with one or more groups independently selected from A2, said aryl radicals whether alone or as part of another group are optionally substituted with one or more groups independently selected from A3, and said heterocycle radicals whether alone or as part of another group are optionally substituted with one or more groups independently selected from A4;

$R^5$ is —H or —$C_1$-$C_8$ alkyl;

or $R^4$ and $R^5$ jointly form a carbocyclic ring and have the formula —$(CR^aR^b)_s$— wherein $R^a$ and $R^b$ are independently selected from —H, —$C_1$-$C_8$ alkyl, —$C_2$-$C_8$ alkenyl, —$C_2$-$C_8$ alkynyl, or carbocycle, and s is selected from 2, 3, 4, 5 or 6;

$R^6$ is —$C_1$-$C_{20}$ alkyl optionally substituted with one or more groups independently selected from A1;

each $R^8$ is independently selected from —OH, —O—($C_1$-$C_{20}$ alkyl), —O—($C_2$-$C_{20}$ alkenyl), or —O—($C_2$-$C_{20}$ alkynyl) wherein said alkyl, alkenyl, and alkynyl radicals are optionally substituted with one or more groups independently selected from A1;

$R^9$ is -hydrogen or —$C_1$-$C_{20}$ alkyl optionally substituted with one or more groups independently selected from A1;

$R^{19}$ is aryl, heterocycle, or carbocycle; wherein said carbocycle radical is optionally substituted with one or more groups independently selected from A2, said aryl radical is optionally substituted with one or more groups independently selected from A3, and said heterocycle radical is optionally substituted with one or more groups independently selected from A4;

$R^{20}$ is $OR^{18}$; wherein $R^{18}$ is —H, a hydroxyl protecting group, or a direct bond where $OR^{18}$ represents =O;

$R^{21}$ is selected from —H, —$C_1$-$C_{20}$ alkyl, —$C_2$-$C_{20}$ alkenyl, —$C_2$-$C_{20}$ alkynyl, or -carbocycle; wherein said alkyl, alkenyl, and alkynyl radicals are optionally substituted with one or more groups independently selected from A1, and said carbocycle radical is optionally substituted with one or more groups independently selected from A2;

and A1, A2, A3, and A4 are as defined herein; or a pharmaceutically acceptable salt or solvate form thereof.

Auristatins of the formula $D_E$ include those wherein $R^2$ is —$C_1$-$C_8$ alkyl;

$R^3$, $R^4$ and $R^7$ are independently selected from —H, —$C_1$-$C_{20}$ alkyl, —$C_2$-$C_{20}$ alkenyl, —$C_2$-$C_{20}$ alkynyl, monocyclic $C_3$-$C_6$ carbocycle, —$C_1$-$C_{20}$ alkylene(monocyclic $C_3$-$C_6$ carbocycle), —$C_2$-$C_{20}$ alkenylene(monocyclic $C_3$-$C_6$ carbocycle), —$C_2$-$C_{20}$ alkynylene(monocyclic $C_3$-$C_6$ carbocycle), —$C_6$-$C_{10}$ aryl, —$C_1$-$C_{20}$ alkylene($C_6$-$C_{10}$ aryl), —$C_2$-$C_{20}$ alkenylene($C_6$-$C_{10}$ aryl), —$C_2$-$C_{20}$ alkynylene($C_6$-$C_{10}$ aryl), -heterocycle, —$C_1$-$C_{20}$ alkylene(heterocycle), —$C_2$-$C_{20}$ alkenylene(heterocycle), or —$C_2$-$C_{20}$ alkynylene (heterocycle); wherein said alkyl, alkenyl, alkynyl, alkylene, alkenylene, and alkynylene radicals whether alone or as part of another group are optionally substituted with one or more groups independently selected from A1, said carbocycle radicals whether alone or as part of another group are optionally substituted with one or more groups independently selected from A2, said aryl radicals whether alone or as part of another group are optionally substituted with one or more groups independently selected from A3, and said heterocycle radicals whether alone or as part of another group are optionally substituted with one or more groups independently selected from A4;

$R^5$ is -hydrogen;

$R^6$ is —$C_1$-$C_8$ alkyl;

each $R^8$ is independently selected from —OH, —O—($C_1$-$C_{20}$ alkyl), —O—($C_2$-$C_{20}$ alkenyl), or —O—($C_2$-$C_{20}$ alkynyl) wherein said alkyl, alkenyl, and alkynyl radicals are optionally substituted with one or more groups independently selected from A1;

$R^9$ is -hydrogen or —$C_1$-$C_8$ alkyl;

$R^{19}$ is phenyl optionally substituted with one or more groups independently selected from A3;

$R^{20}$ is $OR^{18}$; wherein $R^{18}$ is H, a hydroxyl protecting group, or a direct bond where $OR^{18}$ represents =O;

$R^{21}$ is selected from —H, —$C_1$-$C_{20}$ alkyl, —$C_2$-$C_{20}$ alkenyl, —$C_2$-$C_{20}$ alkynyl, or -carbocycle; wherein said alkyl, alkenyl, and alkynyl radicals are optionally substituted with one or more groups independently selected from A1, and said carbocycle radical is optionally substituted with one or more groups independently selected from A2; and A1, A2, A3, and A4 are as defined herein; or a pharmaceutically acceptable salt or solvate form thereof.

Auristatins of the formula $D_E$ include those wherein $R^2$ is methyl;

$R^3$ is —H, —$C_1$-$C_8$ alkyl, —$C_2$-$C_8$ alkenyl, or —$C_2$-$C_8$ alkynyl, wherein said alkyl, alkenyl and alkynyl radicals are optionally substituted with one or more groups independently selected from A1;

$R^4$ is —H, —$C_1$-$C_8$ alkyl, —$C_2$-$C_8$ alkenyl, —$C_2$-$C_8$ alkynyl, monocyclic $C_3$-$C_6$ carbocycle, —$C_6$-$C_{10}$ aryl, —$C_1$-$C_8$ alkylene($C_6$-$C_{10}$ aryl), —$C_2$-$C_8$ alkenylene($C_6$-$C_{10}$ aryl), —$C_2$-$C_8$ alkynylene($C_6$-$C_{10}$ aryl), —$C_1$-$C_8$ alkylene (monocyclic $C_3$-$C_6$ carbocycle), —$C_2$-$C_8$ alkenylene (monocyclic $C_3$-$C_6$ carbocycle), —$C_2$-$C_8$ alkynylene(monocyclic $C_3$-$C_6$ carbocycle); wherein said alkyl, alkenyl, alkynyl, alkylene, alkenylene, and alkynylene radicals whether alone or as part of another group are optionally substituted with one or more groups independently selected from A1; said carbocyle radicals whether alone or as part of another group are optionally substituted with one or more groups independently selected from A2; and said aryl radicals whether alone or as part of another group are optionally substituted with one or more groups independently selected from A3;

$R^5$ is H; $R^6$ is methyl;

$R^7$ is —$C_1$-$C_8$ alkyl, —$C_2$-$C_8$ alkenyl or —$C_2$-$C_8$ alkynyl; each $R^8$ is methoxy;

$R^9$ is -hydrogen or —$C_1$-$C_8$ alkyl;

$R^{19}$ is phenyl;

$R^{20}$ is $OR^{18}$; wherein $R^{18}$ is —H, a hydroxyl protecting group, or a direct bond where $OR^{18}$ represents =O;

$R^{21}$ is methyl; and A1, A2, and A3 are as defined herein; or a pharmaceutically acceptable salt or solvate form thereof.

Auristatins of the formula $D_E$ include those wherein $R^2$ is methyl; $R^3$ is H or $C_1$-$C_3$ alkyl; $R^4$ is $C_1$-$C_5$ alkyl; $R^5$ is H; $R^6$ is methyl; $R^7$ is isopropyl or sec-butyl; $R^8$ is methoxy; $R^9$ is hydrogen or $C_1$-$C_8$ alkyl; $R^{19}$ is phenyl; $R^{20}$ is $OR^{18}$; wherein $R^{18}$ is H, a hydroxyl protecting group, or a direct bond where $OR^{18}$ represents =O; and $R^{21}$ is methyl; or a pharmaceutically acceptable salt or solvate form thereof.

Auristatins of the formula $D_E$ include those wherein $R^2$ is methyl or $C_1$-$C_3$ alkyl; $R^3$ is H or $C_1$-$C_3$ alkyl; $R^4$ is $C_1$-$C_5$ alkyl; $R^5$ is H; $R^6$ is $C_1$-$C_3$ alkyl; $R^7$ is $C_1$-$C_5$ alkyl; $R^8$ is $C_1$-$C_3$ alkoxy; $R^9$ is hydrogen or $C_1$-$C_8$ alkyl; $R^{19}$ is phenyl; $R^{20}$ is $OR^{18}$; wherein $R^{18}$ is H, a hydroxyl protecting group, or a direct bond where $OR^{18}$ represents =O; and $R^{21}$ is $C_1$-$C_3$ alkyl; or a pharmaceutically acceptable salt or solvate form thereof.

Auristatins of the formula $D_F$ include those wherein $R^2$ is —$C_1$-$C_{20}$ alkyl, —$C_2$-$C_{20}$ alkenyl, or —$C_2$-$C_{20}$ alkynyl, each of which is optionally substituted with one or more groups independently selected from A1;

$R^3$, $R^4$, and $R^7$ are independently selected from —H, —$C_1$-$C_{20}$ alkyl, —$C_2$-$C_{20}$ alkenyl, —$C_2$-$C_{20}$ alkynyl, monocyclic $C_3$-$C_6$ carbocycle, —$C_1$-$C_{20}$ alkylene(monocyclic $C_3$-$C_6$ carbocycle), —$C_2$-$C_{20}$ alkenylene(monocyclic $C_3$-$C_6$ carbocycle), —$C_2$-$C_{20}$ alkynylene(monocyclic $C_3$-$C_6$ carbocycle), $C_6$-$C_{10}$ aryl, —$C_1$-$C_{20}$ alkylene($C_6$-$C_{10}$ aryl), —$C_2$-$C_{20}$ alkenylene($C_6$-$C_{10}$ aryl), —$C_2$-$C_{20}$ alkynylene($C_6$-$C_{10}$ aryl), -heterocycle, —$C_1$-$C_{20}$ alkylene(heterocycle), —$C_2$-$C_{20}$ alkenylene(heterocycle), or —$C_2$-$C_{20}$ alkynylene (heterocycle); wherein said alkyl, alkenyl, alkynyl, alkylene, alkenylene, and alkynylene radicals whether alone or as part of another group are optionally substituted with one or more groups independently selected from A1, said carbocycle radicals whether alone or as part of another group are optionally substituted with one or more groups independently selected from A2, said aryl radicals whether alone or as part of another group are optionally substituted with one or more groups independently selected from A3, and said heterocycle radicals whether alone or as part of another group are optionally substituted with one or more groups independently selected from A4;

$R^5$ is —H;

$R^6$ is —H, —$C_1$-$C_{20}$ alkyl, —$C_2$-$C_{20}$ alkenyl, or —$C_2$-$C_{20}$ alkynyl, wherein said alkyl, alkenyl and alkynyl radicals are optionally substituted with one or more groups independently selected from A1;

each $R^8$ is independently selected from —H, —OH, —$C_1$-$C_{20}$ alkyl, —$C_2$-$C_{20}$ alkenyl, —$C_2$-$C_{20}$ alkynyl, —O—($C_1$-$C_{20}$ alkyl), —O—($C_2$-$C_{20}$ alkenyl), —O—($C_1$-$C_{20}$ alkynyl), or carbocycle, wherein said alkyl, alkenyl, and alkynyl radicals, whether alone or as part of another group, are optionally substituted with one or more groups independently selected from A1 and said carbocycle is optionally substituted with one or more groups independently selected from A2;

$R^9$ is —H, —$C_1$-$C_{20}$ alkyl, —$C_2$-$C_{20}$ alkenyl, or —$C_2$-$C_{20}$ alkynyl; wherein said alkyl, alkenyl and alkynyl radical are optionally substituted with one or more groups independently selected from A1;

$R^{10}$ is phenyl optionally substituted with one or more groups independently selected from A3;

Z is —O—, —S—, —NH—, or —$NR^{12}$, wherein $R^{12}$ is —$C_1$-$C_{20}$ alkyl, —$C_2$-$C_{20}$ alkenyl, or —$C_2$-$C_{20}$ alkynyl, each of which is optionally substituted with one or more groups independently selected from A1;

$R^{11}$ is —H, —$C_1$-$C_{20}$ alkyl, —$C_2$-$C_{20}$ alkenyl, —$C_2$-$C_{20}$ alkynyl, -aryl, -heterocycle, —$(R^{13}O)_m$—$R^{14}$, or —$(R^{13}O)_m$—$CH(R^{15})_2$ wherein said alkyl, alkenyl and alkynyl radicals are optionally substituted with one or more groups independently selected from A1, said aryl radical is optionally substituted with one or more groups independently selected from A3, and said heterocycle is optionally substituted with one or more groups independently selected from A4;

m is an integer ranging from 1-1000;

$R^{13}$ is —$C_2$-$C_{20}$ alkylene, —$C_2$-$C_{20}$ alkenylene, or —$C_2$-$C_{20}$ alkynylene, each of which is optionally substituted with one or more groups independently selected from A1;

$R^{14}$ is —H, —$C_1$-$C_{20}$ alkyl, —$C_2$-$C_{20}$ alkenyl, or —$C_2$-$C_{20}$ alkynyl wherein said alkyl, alkenyl and alkynyl radicals are optionally substituted with one or more groups independently selected from A1;

each occurrence of $R^{15}$ is independently —H, —COOH, —$(CH_2)_n$—$N(R^{16})_2$, —$(CH_2)_n$—$SO_3H$, —$(CH_2)_n$—$SO_3$—$C_1$-$C_{20}$ alkyl, —$(CH_2)_n$—$SO_3$—$C_2$-$C_{20}$ alkenyl, or —$(CH_2)_n$—$SO_3$—$C_2$-$C_{20}$ alkynyl wherein said alkyl, alkenyl and alkynyl radicals are optionally substituted with one or more groups independently selected from A1;

each occurrence of $R^{16}$ is independently —H, —$C_1$-$C_{20}$ alkyl, —$C_2$-$C_{20}$ alkenyl, —$C_2$-$C_{20}$ alkynyl or —$(CH_2)_n$—COOH wherein said alkyl, alkenyl and alkynyl radicals are optionally substituted with one or more groups independently selected from A1;

n is an integer ranging from 0 to 6; and A1, A2, A3, and A4 are as defined herein; or a pharmaceutically acceptable salt or solvate form thereof.

Auristatins of the formula $D_F$ include those wherein $R^2$ is methyl;

$R^3$, $R^4$, and $R^7$ are independently selected from —H, —$C_1$-$C_{20}$ alkyl, —$C_2$-$C_{20}$ alkenyl, —$C_2$-$C_{20}$ alkynyl, monocyclic $C_3$-$C_6$ carbocycle, —$C_1$-$C_{20}$ alkylene(monocyclic $C_3$-$C_6$ carbocycle), —$C_2$-$C_{20}$ alkenylene(monocyclic $C_3$-$C_6$ carbocycle), —$C_2$-$C_{20}$ alkynylene(monocyclic $C_3$-$C_6$ carbocycle), —$C_6$-$C_{10}$ aryl, —$C_1$-$C_{20}$ alkylene($C_6$-$C_{10}$ aryl), —$C_2$-$C_{20}$ alkenylene($C_6$-$C_{10}$ aryl), —$C_2$-$C_{20}$ alkynylene($C_6$-$C_{10}$ aryl), -heterocycle, —$C_1$-$C_{20}$ alkylene(heterocycle), —$C_2$-$C_{20}$ alkenylene(heterocycle), or —$C_2$-$C_{20}$ alkynylene (heterocycle); wherein said alkyl, alkenyl, alkynyl, alkylene, alkenylene, and alkynylene radicals whether alone or as part of another group are optionally substituted with one or more groups independently selected from A1, said carbocycle radicals whether alone or as part of another group are optionally substituted with one or more groups independently selected from A2, said aryl radicals whether alone or as part of another group are optionally substituted with one or more groups independently selected from A3, and said heterocycle radicals whether alone or as part of another group are optionally substituted with one or more groups independently selected from A4;

$R^5$ is —H;

$R^6$ is methyl;

each $R^8$ is methoxy;

$R^9$ is —H, —$C_1$-$C_{20}$ alkyl, —$C_2$-$C_{20}$ alkenyl, or —$C_2$-$C_{20}$ alkynyl; wherein said alkyl, alkenyl and alkynyl radical are optionally substituted with one or more groups independently selected from A1;

$R^{10}$ is aryl optionally substituted with one or more groups independently selected from A3, or heterocycle optionally substituted with one or more groups independently selected from A4;

Z is —O—, —S—, —NH—, or —$NR^{12}$—, wherein $R^{12}$ is —$C_1$-$C_{20}$ alkyl, —$C_2$-$C_{20}$ alkenyl, or —$C_2$-$C_{20}$ alkynyl, each of which is optionally substituted with one or more groups independently selected from A1;

$R^{11}$ is —H, —$C_1$-$C_{20}$ alkyl, —$C_2$-$C_{20}$ alkenyl, —$C_2$-$C_{20}$ alkynyl, -aryl, -heterocycle, —$(R^{13}O)_m$—$R^{14}$, or —$(R^{13}O)_m$—$CH(R^{15})_2$ wherein said alkyl, alkenyl and alkynyl radicals are optionally substituted with one or more groups independently selected from A1, said aryl radical is optionally substituted with one or more groups independently selected from A3, and said heterocycle is optionally substituted with one or more groups independently selected from A4;

m is an integer ranging from 1-1000;

$R^{13}$ is —$C_2$-$C_{20}$ alkylene, —$C_2$-$C_{20}$ alkenylene, or —$C_2$-$C_{20}$ alkynylene, each of which is optionally substituted with one or more groups independently selected from A1;

$R^{14}$ is —H, —$C_1$-$C_{20}$ alkyl, —$C_2$-$C_{20}$ alkenyl, or —$C_2$-$C_{20}$ alkynyl wherein said alkyl, alkenyl and alkynyl radicals are optionally substituted with one or more groups independently selected from A1;

each occurrence of $R^{15}$ is independently —H, —COOH, —$(CH_2)_n$—$N(R^{16})_2$, —$(CH_2)_n$—$SO_3H$, —$(CH_2)_n$—$SO_3$—$C_1$-$C_{20}$ alkyl, —$(CH_2)_n$—$SO_3$—$C_2$-$C_{20}$ alkenyl, or —$(CH_2)_n$—$SO_3$—$C_2$-$C_{20}$ alkynyl wherein said alkyl, alkenyl and alkynyl radicals are optionally substituted with one or more groups independently selected from A1;

each occurrence of $R^{16}$ is independently —H, —$C_1$-$C_{20}$ alkyl, —$C_2$-$C_{20}$ alkenyl, —$C_2$-$C_{20}$ alkynyl or —$(CH_2)_n$—COOH wherein said alkyl, alkenyl and alkynyl radicals are optionally substituted with one or more groups independently selected from A1;

n is an integer ranging from 0 to 6; and A1, A2, A3, and A4 are as defined herein; or a pharmaceutically acceptable salt or solvate form thereof.

In certain of these embodiments, $R^{10}$ is phenyl optionally substituted with one or more groups independently selected from A3.

Auristatins of the formula $D_F$ include those wherein the groups of $R^2$, $R^3$, $R^4$, $R^5$, $R^6$, $R^7$, $R^8$, and $R^9$ are unsubstituted and the groups of $R^{10}$ and $R^{11}$ are as described herein.

Auristatins of the formula $D_F$ include those wherein said alkyl, alkenyl, alkynyl, alkylene, alkenylene, alkynyklene, aryl, carbocyle, and heterocycle radicals are unsubstituted.

Auristatins of the formula $D_F$ include those wherein
$R^2$ is $C_1$-$C_3$ alkyl; $R^3$ is H or $C_1$-$C_3$ alkyl; $R^4$ is $C_1$-$C_5$ alkyl; $R^5$ is H; $R^6$ is $C_1$-$C_3$ alkyl; $R^7$ is $C_1$-$C_5$ alkyl; $R^8$ is $C_1$-$C_3$ alkoxy; $R^9$ is hydrogen or $C_1$-$C_8$ alkyl; $R^{10}$ is phenyl optionally substituted with one or more groups independently selected from A3; Z is O, S, or NH; and $R^{11}$ and A3 is as defined herein; or a pharmaceutically acceptable salt or solvate form thereof.

Auristatins of the formula $D_F$ include those wherein
$R^2$ is methyl; $R^3$ is H or $C_1$-$C_3$ alkyl; $R^4$ is $C_1$-$C_5$ alkyl; $R^5$ is H; $R^6$ is methyl; $R^7$ is isopropyl or sec-butyl; $R^8$ is methoxy; $R^9$ is hydrogen or $C_1$-$C_8$ alkyl; $R^{10}$ is phenyl optionally substituted with one or more groups independently selected from A3; Z is O, S, or NH; and $R^{11}$ and A3 is as defined herein; or a pharmaceutically acceptable salt or solvate form thereof.

Auristatins of the formula $D_F$ include those wherein
$R^2$ is methyl; $R^3$ is H or $C_1$-$C_3$ alkyl; $R^4$ is $C_1$-$C_5$ alkyl; $R^5$ is H; $R^6$ is methyl; $R^7$ is isopropyl or sec-butyl; $R^8$ is methoxy; $R^9$ is hydrogen or $C_1$-$C_8$ alkyl; $R^{10}$ is phenyl; and Z is O or NH and $R^{11}$ is as defined herein, preferably hydrogen; or a pharmaceutically acceptable salt or solvate form thereof.

Auristatins of the formula $D_F$ include those wherein
$R^2$ is $C_1$-$C_3$ alkyl; $R^3$ is H or $C_1$-$C_3$ alkyl; $R^4$ is $C_1$-$C_5$ alkyl; $R^5$ is H; $R^6$ is $C_1$-$C_3$ alkyl; $R^7$ is $C_1$-$C_5$ alkyl; $R^8$ is $C_1$-$C_3$ alkoxy; $R^9$ is hydrogen or $C_1$-$C_8$ alkyl; $R^{10}$ is phenyl; and Z is O or NH and $R^{11}$ is as defined herein, preferably hydrogen; or a pharmaceutically acceptable salt or solvate form thereof.

Auristatins of the formula $D_E$ or $D_F$ include those wherein $R^3$, $R^4$ and $R^7$ are independently isopropyl or sec-butyl and $R^5$ is —H. In an exemplary embodiment, $R^3$ and $R^4$ are each isopropyl, $R^5$ is H, and $R^7$ is sec-butyl. The remainder of the substituents are as defined herein.

Auristatins of the formula $D_E$ or $D_F$ include those wherein $R^2$ and $R^6$ are each methyl, and $R^9$ is H. The remainder of the substituents are as defined herein.

Auristatins of the formula $D_E$ or $D_F$ include those wherein each occurrence of $R^8$ is —$OCH_3$. The remainder of the substituents are as defined herein.

Auristatins of the formula $D_E$ or $D_F$ include those wherein $R^3$ and $R^4$ are each isopropyl, $R^2$ and $R^6$ are each methyl, $R^5$ is H, $R^7$ is sec-butyl, each occurrence of $R^8$ is —$OCH_3$, and $R^9$ is H. The remainder of the substituents are as defined herein.

Auristatins of the formula $D_F$ include those wherein Z is —O— or —NH—. The remainder of the substituents are as defined herein.

Auristatins of the formula $D_F$ include those wherein $R^{10}$ is aryl. The remainder of the substituents are as defined herein.

Auristatins of the formula $D_F$ include those wherein, $R^{10}$ is -phenyl. The remainder of the substituents are as defined herein.

Auristatins of the formula $D_F$ include those wherein Z is —O—, and $R^{11}$ is H, methyl or t-butyl. The remainder of the substituents are as defined herein.

Auristatins of the formula $D_F$ include those wherein, when Z is —NH, $R^{11}$ is —$CH(R^{15})_2$, wherein $R^{15}$ is —$(CH_2)_n$—N$(R^{16})_2$, and $R^{16}$ is —$C_1$-$C_8$ alkyl or —$(CH_2)_n$—COOH. The remainder of the substituents are as defined herein.

Auristatins of the formula $D_F$ include those wherein when Z is —NH, $R^{11}$ is —$CH(R^{15})_2$, wherein $R^{15}$ is —$(CH_2)_n$—$SO_3H$. The remainder of the substituents are as defined herein.

In preferred embodiments, when D is an auristatin of formula $D_E$, w is an integer ranging from 1 to 12, preferably 2 to 12, y is 1 or 2, and a is preferably 1.

In some embodiments, wherein D is an auristatin of formula $D_F$, a is 1 and w and y are 0.

Illustrative Drug units (-D) include the drug units having the following structures:

-continued
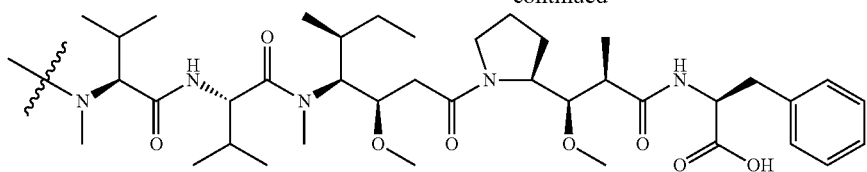
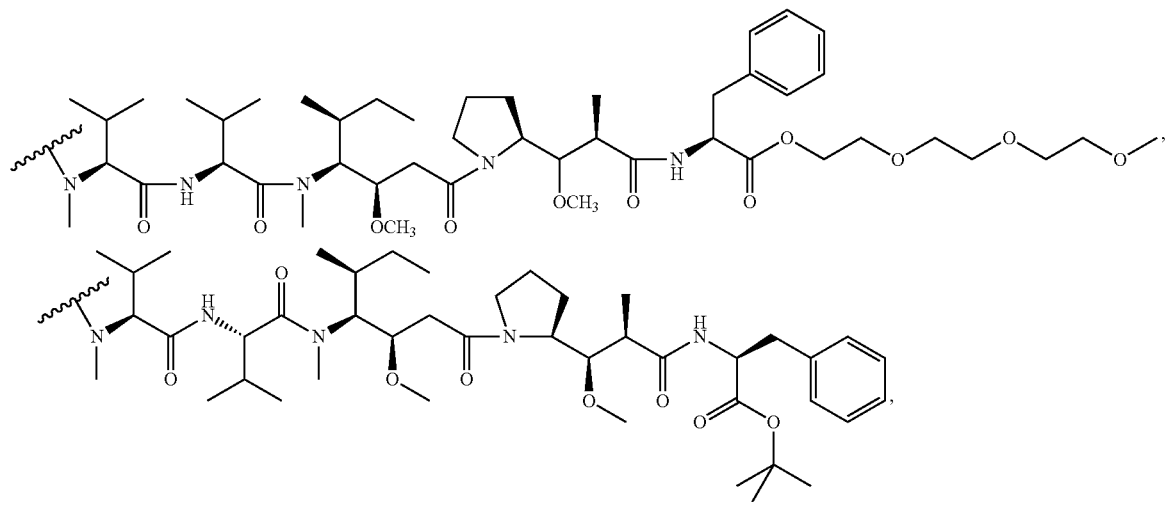
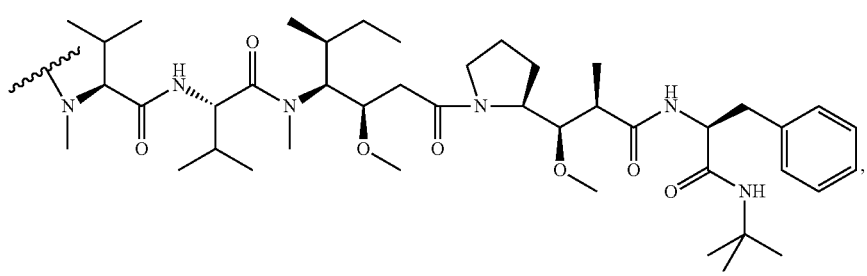
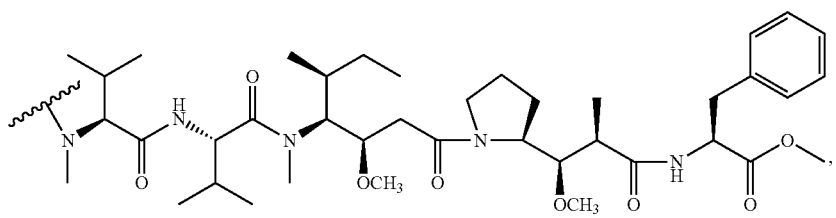
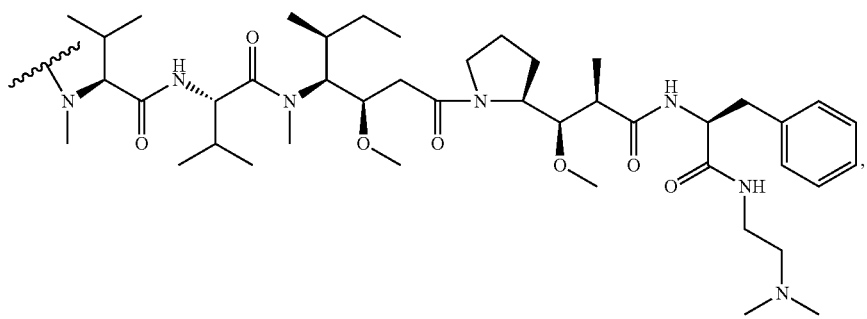

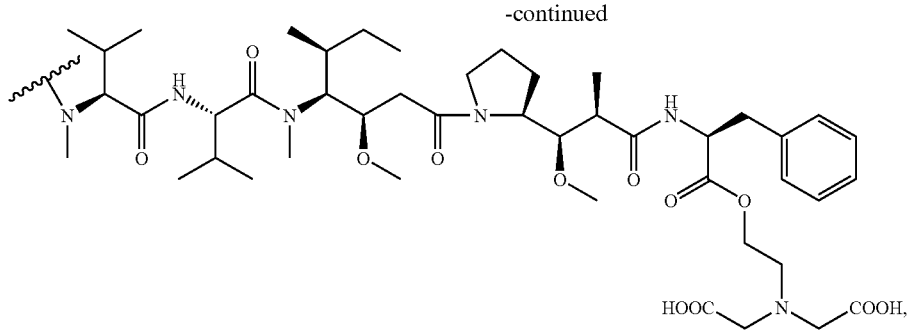

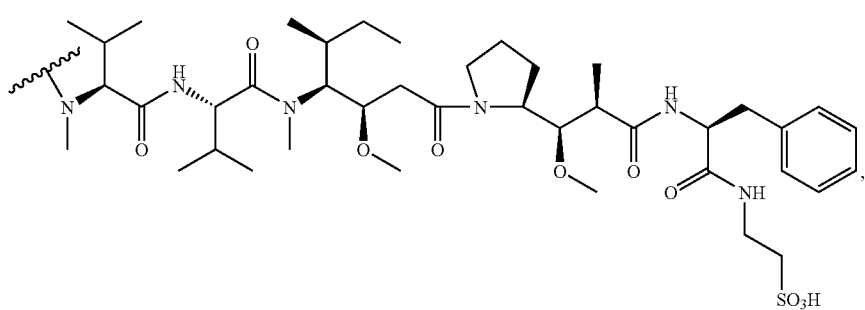

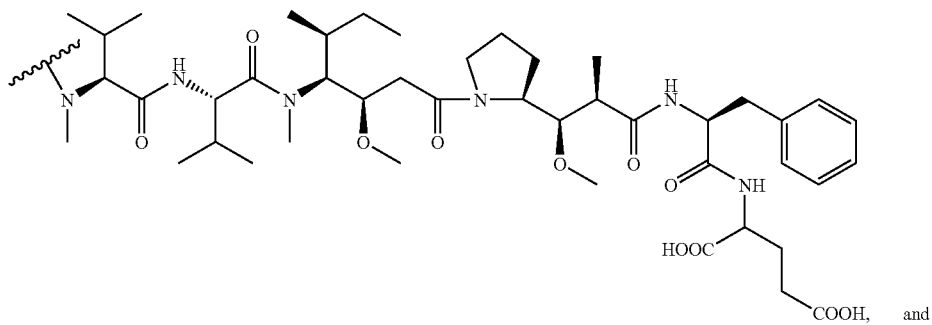

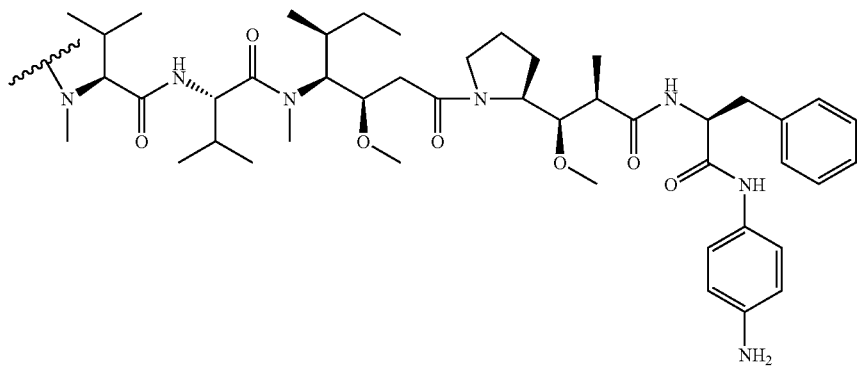

or pharmaceutically acceptable salts or solvates thereof.

In one aspect, hydrophilic groups, such as but not limited to triethylene glycol esters (TEG) can be attached to the Drug Unit at $R^{11}$. Without being bound by theory, the hydrophilic groups assist in the internalization and non-agglomeration of the Drug Unit.

In some embodiments, the Drug unit is not TZT-1027. In some embodiments, the Drug unit is not auristatin E, dolastatin 10, or auristatin PE.

Exemplary antibody-drug conjugate compounds have the following structures wherein "mAb-s-" represents the anti-CD30 antibody:

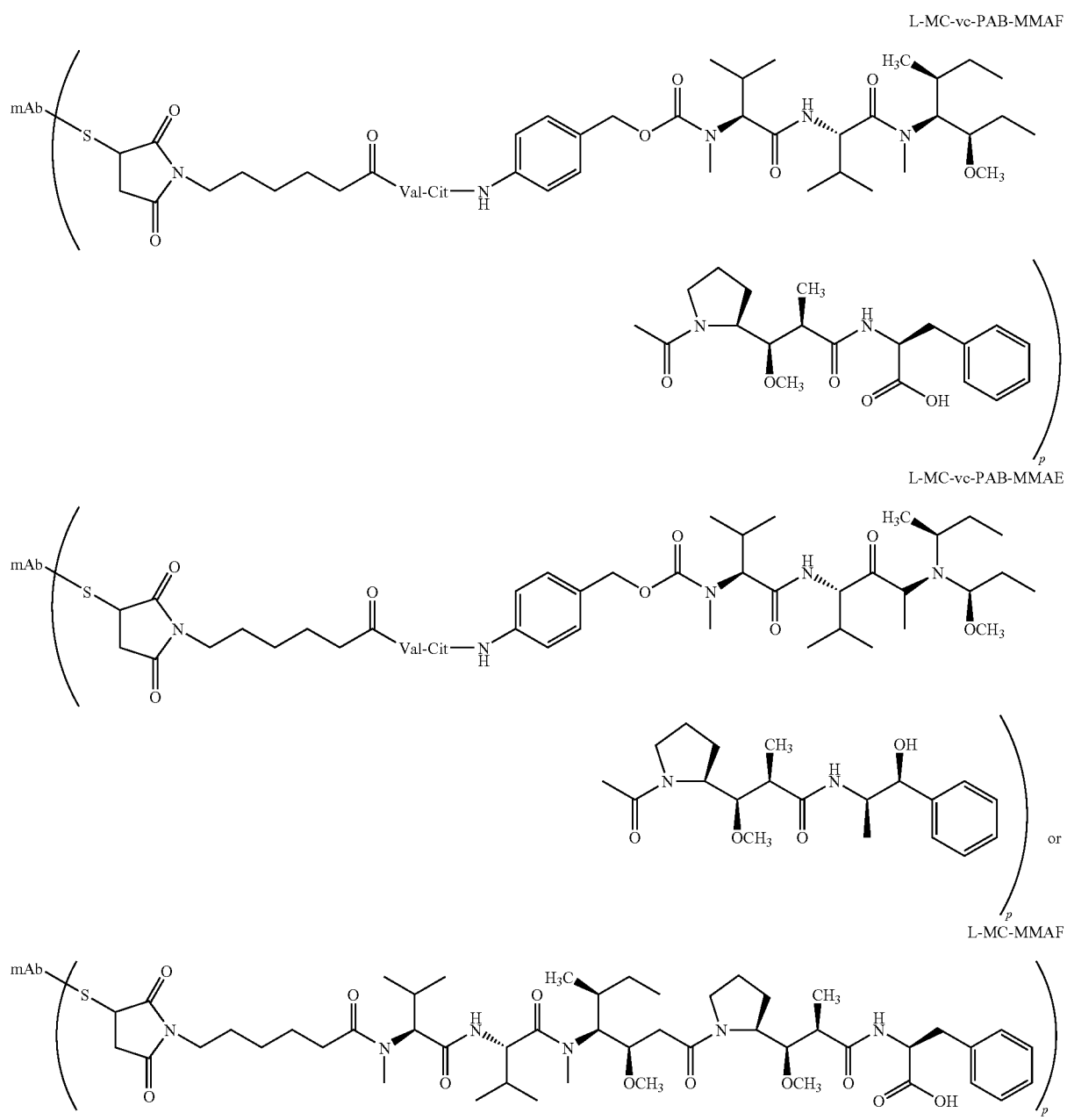

wherein Val is valine, and Cit is citrulline.

Antibody Unit

The antibody unit (L) has at least one functional group that can form a bond with a functional group of a Linker unit or a Drug unit. Useful functional groups that can be present on an antibody unit, either naturally, via chemical manipulation or via engineering, include, but are not limited to, sulfhydryl (—SH), amino, hydroxyl, carboxy, the anomeric hydroxyl group of a carbohydrate, and carboxyl. In some embodiments, an antibody unit functional group is a sulfhydryl group. The sulfhydryl group is typically a solvent accessible sulfhydryl group, such as a solvent accessible sulfhydryl group on a cysteine residue. Sulfhydryl groups can be generated by reduction of an intramolecular or intermolecular disulfide bond of an antibody. Sulfhydryl groups also can be generated by reaction of an amino group of a lysine moiety of an antibody using 2-iminothiolane (Traut's reagent) or another sulfhydryl generating reagent.

In some embodiments, one or more sulfhydryl groups are engineered into an antibody unit, such as by amino acid substitution. For example, a sulfhydryl group can be introduced into an antibody unit. In some embodiments, a sulfhydryl group is introduced by an amino acid substitution of serine or threonine to a cysteine residue, and/or by addition of a cysteine residue into an antibody unit (an engineered cysteine residue). In some embodiments, the cysteine residue is an internal cysteine residue, i.e., not located at the N-terminus or C-terminus of the antibody moiety.

To control the number of Drug or Linker unit-Drug units attached to an antibody unit, one or more cysteine residues can be eliminated by amino acid substitution. For example, the number of solvent accessible cysteine residues in an immunoglobulin hinge region can be reduced by amino acid substitution of cysteine to serine residues.

In some embodiments, an antibody unit contains 1, 2, 3, 4, 5, 6 7 or 8 solvent-accessible cysteine residues. In some embodiments, an antibody unit contains 2 or 4 solvent-accessible cysteine residues.

The present invention also provides kits for the treatment of HL. The kit can comprise (a) a container containing an antibody-drug conjugate and (b) one or more additional containers containing the chemotherapeutic drugs. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit.

The present invention is not to be limited in scope by the specific embodiments described herein. Various modifications of the invention in addition to those described herein will become apparent to those skilled in the art from the foregoing description and accompanying figures. Such modifications are intended to fall within the scope of the appended claims.

All publications and patent documents cited above are hereby incorporated by reference in their entirety for all purposes to the same extent as if each were so individually denoted.

The invention is further described in the following examples, which are in not intended to limit the scope of the invention.

EXAMPLES

Example 1

Combination of the Antibody-Drug Conjugate cAC10-vcMMAE (cAC10-MC-vc-PAB-MMAE) with Chemotherapeutic Regimens for the Treatment of HL The effects of combining cAC10-vcMMAE treatment with gemcitabine or ABVD or other chemotherapeutic regimens were studied in a L540cy tumor model (Francisco et al., Blood 2003; 102:1458-146). To determine the maximum tolerated dose (MTD) of ABVD and gemcitabine, body weights of SCID mice treated with increasing amounts of drugs were assessed daily. The criteria defining the MTD were ≧20% decrease in body weights or other signs of morbidity during the entire treatment followed by a 2 week recovery period. Tumor quadrupling or triplicating times were chosen as time to endpoint (TTE), which were determined by using the non-liner regression analysis for exponential growth of each individual tumor growth data set from each experimental animal. The tumor quadrupling time was calculated based on the tumor volume at the beginning of treatment. Animals that did not reach the endpoint were assigned a TTE value equal to the last day of the study. % TGD (tumor growth delay) reflects the delay in reaching TTE relative to control treated tumors, which was determined by using the formula: % TGD=[(T−C)/C]×100, where T and C are the median times in days for treated and control groups, to reach TTE, using the start of treatment as day 1. Statistical analysis and graphic presentations were conducted using Prism (GraphPad) software for Windows 3.03 software. Median tumor growth curves show group median tumor volumes as a function of time. The Logrank test was used to analyze the significance of the differences between TTE of treated and control tumor groups, with differences deemed significant (*) at $0.01 \leq P \leq 0.05$, and highly significant (**) at $P<0.01$. A 1 mg/kg, q4dx3 treatment schedule for cAC10-vcMMAE was selected based on previous reports demonstrating maximal therapeutics effects at a q4dx4 schedule.

Administration of ABVD or cAC10-vcMMAE alone to L540cy tumor bearing mice induced tumor regressions and significant tumor growth delays compared to control treatment (FIG. 1A). However, tumors eventually progressed. There were 4/9 durable tumor regressions in the animals treated with cAC10-vcMMAE monotherapy and 0/9 durable responses in the animals treated with ABVD monotherapy. In contrast, combination of cAC10-vcMMAE with ABVD resulted in durable tumor regressions in all experimental animals (9/9 durable responses) (FIG. 1A) and a statistically significant increase in tumor growth delay relative to each treatment arm alone. Similarly, when treatment was initiated at 300 mm$^3$ tumor volume, there was a significant increase in TGD and 50% durable responses (5/10 animals) in the animals treated with combination therapy (FIG. 1B), whereas there were 2/10 durable responses in animals treated with cAC10-vcMMAE monotherapy and no durable responsese in animals treated with ABVD monotherapy. It should be noted that the dosages for the ABVD regimen were reduced by 25% in the high-bar model as compared to the low-bar model. The delay in tumor growth induced by the combination treatment was highly significant relative to each individual treatment arm alone (Table 1). No significant differences in body weight loss or morbidity were noted in the combination group, suggesting comparable tolerability (data not shown).

TABLE 1

| Treatment | Median TGD (FIG. 1A) (days to quadruple) | Median TGD (FIG. 1B) (days to triple) | Combo vs single agent (P-vlaue) (A) | (B) |
|---|---|---|---|---|
| cAC10-vcMMAE | 63 | 41 | p = 0.0101 | p = 0.05 |
| ABVD | 38.4 | 22.5 | p < 0.0001 | p = 0.001 |
| ABVD + cAC10-vcMMAE | >80.5* | 61.5 | | |

*The experiment was terminated. At this point, there were durable tumor regressions in all animals.

Figure 2:
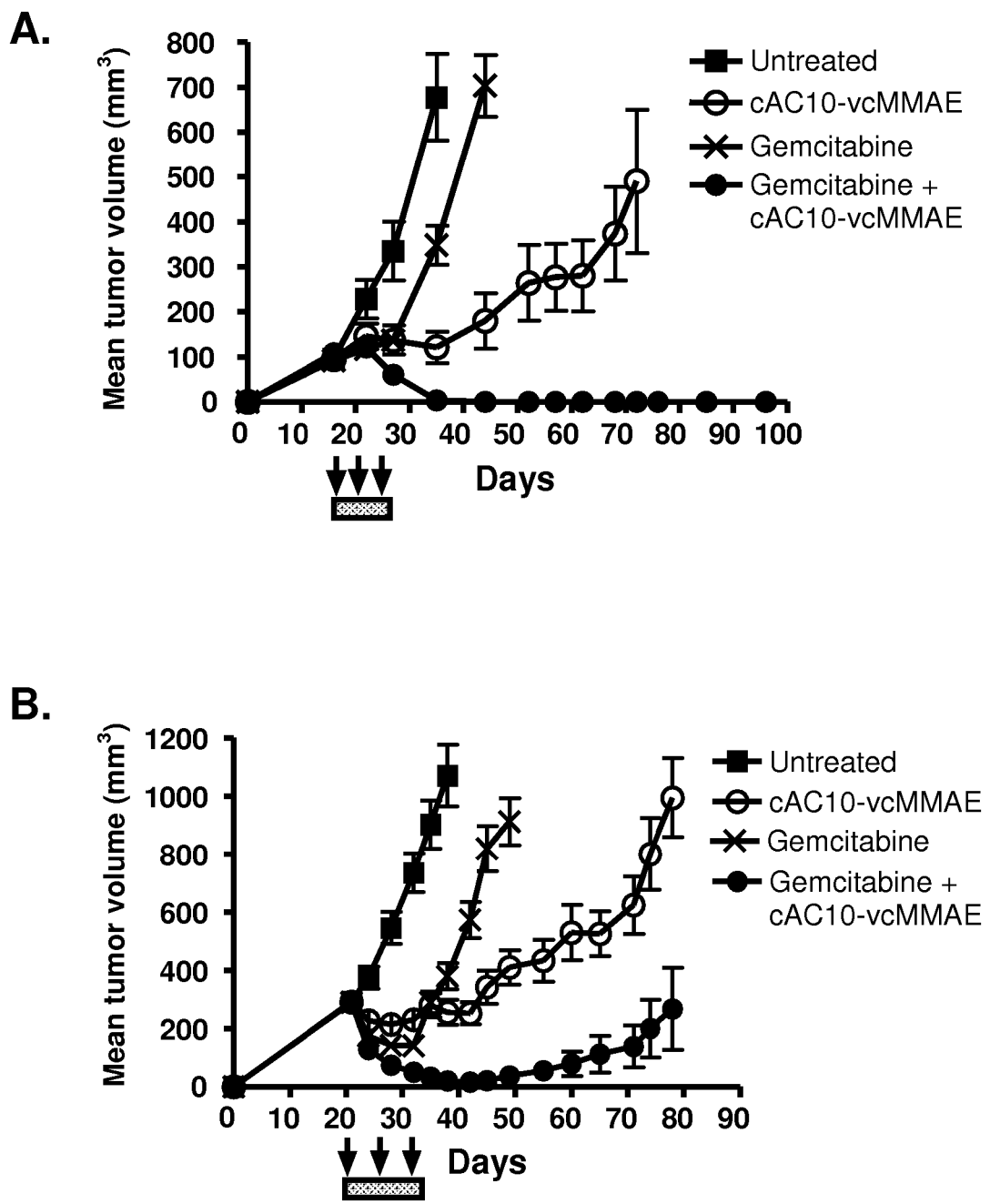
FIG. 2A: Antitumor activity of cAC10-vcMMAE alone or in combination with Gemcitabine on subcutaneous L540cy HL tumors in SCID mice. SCID mice were implanted with L540cy HL cells in the right flank. Groups of mice (5-10/group) were untreated or received cAC10-vcMMAE (1 mg/kg, q4dx3, ip) alone, Gemcitabine (120 mg/kg, q4dx3, ip) alone, or combination treatment with cAC10-vcMMAE and Gemcitabine when tumor sizes averaged approximately 100 mm$^3$.
FIG. 2B: Antitumor activity of cAC10-vcMMAE alone or in combination with Gemcitabine on subcutaneous L540cy HL tumors in SCID mice. SCID mice were implanted with L540cy HL cells in the right flank. Groups of mice (5-10/group) were untreated or received cAC10-vcMMAE (1 mg/kg, q4dx3, ip) alone, Gemcitabine (120 mg/kg, q4dx3, ip) alone, or combination treatment with cAC10-vcMMAE and Gemcitabine, when tumor sizes averaged approximately 300 mm$^3$.

Next, the effect of combining cAC10-vcMMAE with gemcitabine was studied. For this purpose, mice were implanted with L540cy tumors and treated with cAC10-vcMMAE and gemcitabine, either alone or combined. While single arm treatment led to significant delays in tumor growth and one durable response, the combination of cAC10-vcMMAE with gemcitabine enhanced the anti-tumor response and durable responses were found in all animals (5/5, FIG. 2A). Improved efficacy in the combination treatment group was also noted when drug administration occurred when tumors reached a substantially larger size (300 mm$^3$, FIG. 2B). Immunohistochemical analysis of tumors did not reveal significant changes in CD30 expression levels in tumors treated with either ABVD or gemcitabine, ruling out drug interference with target gene expression (data not shown). Similar to the ABVD experiment, combination treatment with gemcitabine resulted in a significant delay in tumor growth, which was more than additive (Table 2) and lead to durable responses. No significant differences in body weight loss or morbidity were noted in the combination group, suggesting comparable tolerability (data not shown).

TABLE 2

| Treatment | Median TGD (FIG. 2A) (days to quadruple) | Median TGD (FIG. 2B) (days to triplicate) | Combo vs single agent (P-vlaue) | |
|---|---|---|---|---|
| | | | (A) | (B) |
| cAC10-vcMMAE | 34 | 39.5 | p = 0.0088 | p = 0.0375 |
| Gemcitabine | 5 | 15.5 | p < 0.0024 | p = 0.0154 |
| Gemcitabine + cAC10-vcMMAE | >75 | >75 | | |

Figure 7:
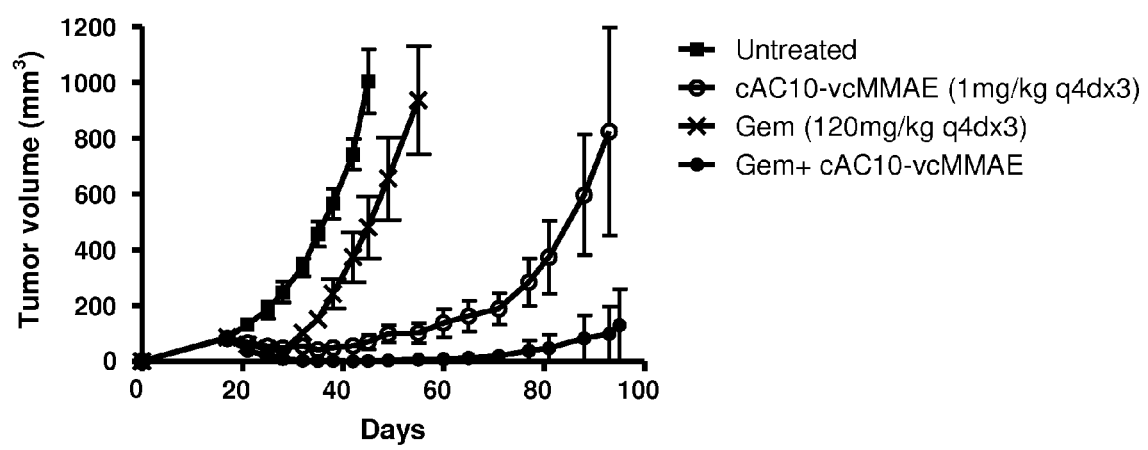
FIG. 7: Antitumor activity of cAC10-vcMMAE alone or in combination with Gemcitabine on subcutaneous L540cy HL tumors in SCID mice. SCID mice were implanted with L540cy HL cells in the right flank. Groups of mice (6-8/group) were untreated or received cAC10-vcMMAE (1 mg/kg, q4dx3, ip) alone, Gemcitabine (120 mg/kg, q4dx3, ip) alone, or combination treatment with cAC10-vcMMAE and Gemcitabine when tumor sizes averaged approximately 100 mm$^3$.
Figure 8:
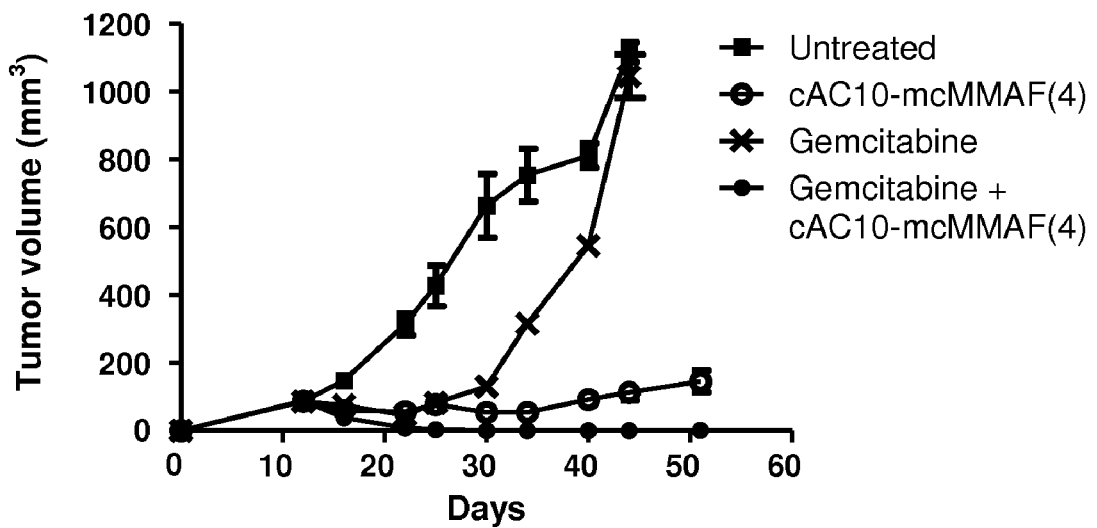
FIG. 8: Antitumor activity of cAC10-mcMMAF alone or in combination with Gemcitabine on subcutaneous L540cy HL tumors in SCID mice. SCID mice were implanted with L540cy HL cells in the right flank. Groups of mice (10/group) were untreated or received cAC10-mcMMAF (1 mg/kg, q4dx3, ip) alone, Gemcitabine (120 mg/kg, q4dx3, ip) alone, or combination treatment with cAC10-mcMMAF and Gemcitabine when tumor sizes averaged approximately 100 mm$^3$.
Figure 9:
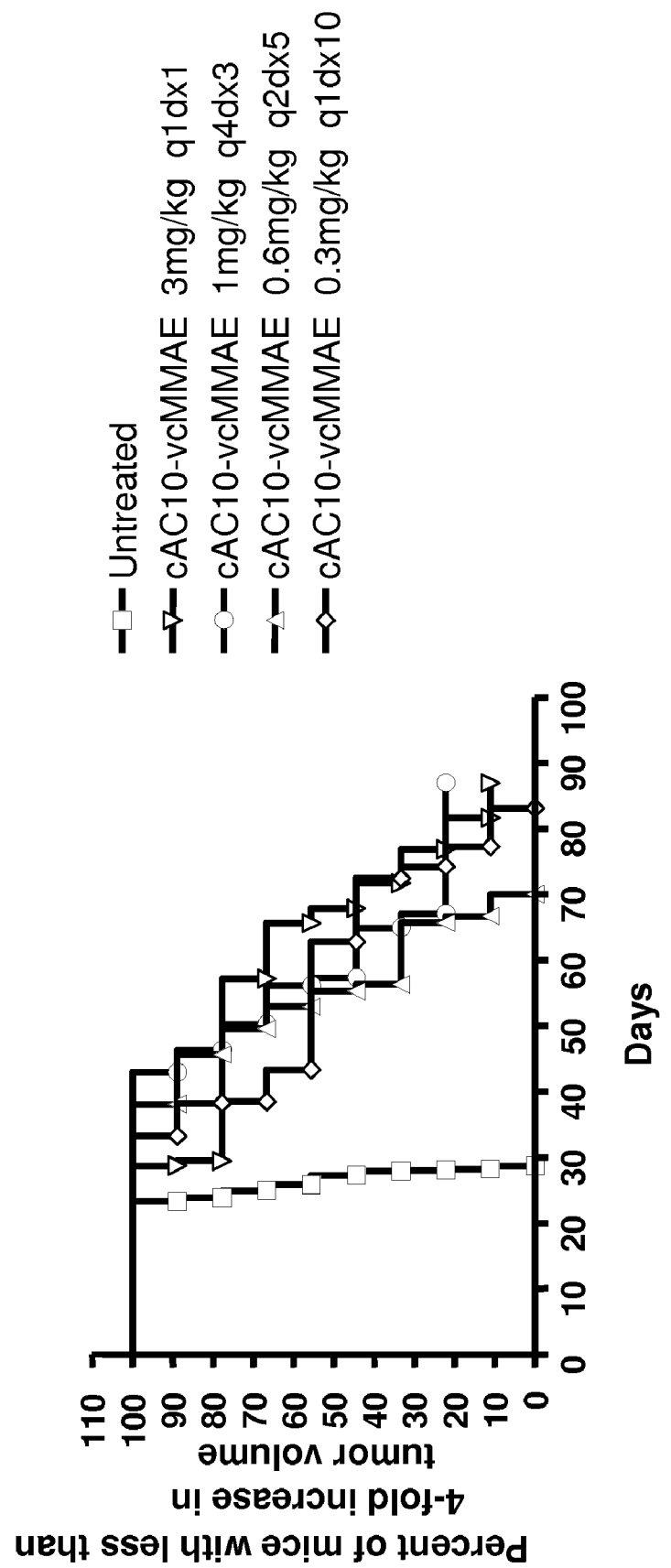
FIG. 9: Altered Dosage Schedule for cAC10-vcMMAE. The total amount of cAC10-vcMMAE was kept constant at 3 mg/kg and the dose was split to various schedules.

In a second study illustrated by FIG. 7 and Table 3 below, 7/8 durable responses were seen with combination treatment with cAC10-vcMMAE and gemcitabine, whereas 1/7 durable responses were seen with single arm treatment with cAC10-vcMMAE and 1/6 durable responses were seen with single arm treatment with gemcitabine.

TABLE 3

| Treatment | Median TGD (FIG. 7) (days to quadruple) | Combo vs single agent (P-vlaue) (A) |
|---|---|---|
| cAC10-vcMMAE | 78.01 | p = 0.0037 |
| Gemcitabine | 42 | P = 0.0021 |
| Gemcitabine + cAC10-vcMMAE | >100* | |

*The experiment was terminated. At this point, there were durable tumor regressions in 7/8 animals.

The effect of combining cAC10-vcMMAE with GVD was studied. For this purpose, mice were implanted with L540cy tumors and treated with cAC10-vcMMAE and GVD, either alone or combined. Treatment was initiated at 100 mm³ tumor volume for two separate experiments that were conducted (3A and 3B). In the first experiment, 6/9 durable responses were seen with the combination therapy whereas 4/9 durable responses were seen with cAC10-vcMMAE treatment alone and 0/9 durable responses with single arm treatment with GVD. In the second experiment, 7/7 durable responses were seen with the combination therapy whereas 0/7 durable responses were seen with cAC10-vcMMAE treatment alone and 0/7 durable responses with single arm treatment with GVD.

TABLE 4

Figure 3:
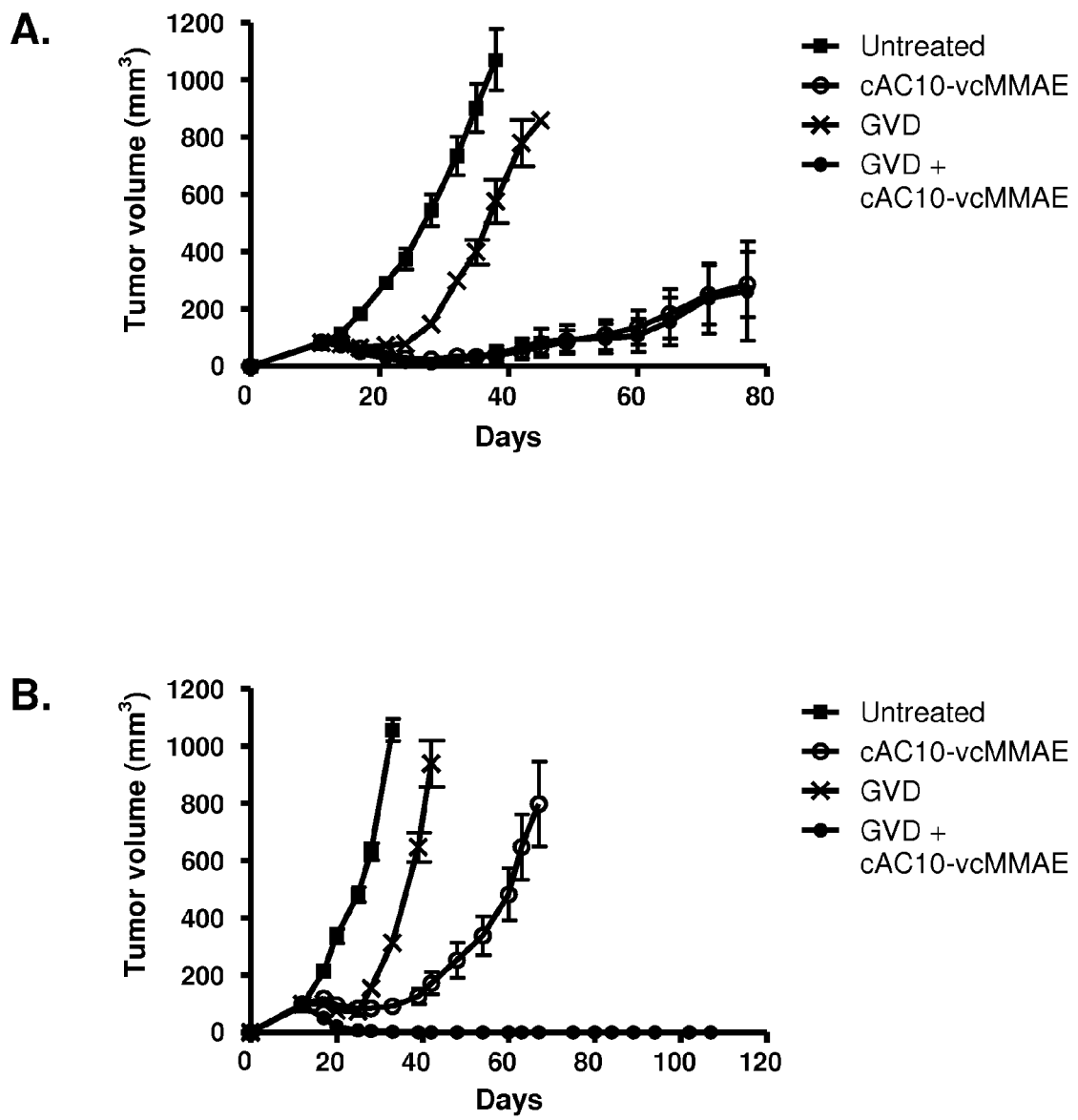
FIG. 3A: Antitumor activity of cAC10-vcMMAE alone or in combination with GVD on subcutaneous L540cy HL tumors in SCID mice. SCID mice were implanted with L540cy HL cells in the right flank. Groups of mice (8-10/group) were untreated or received cAC10-vcMMAE (1 mg/kg, q4dx3, ip) alone, GVD alone, or combination treatment with cAC10-vcMMAE and GVD when tumor sizes averaged approximately 100 mm$^3$. The treatment schedule of GVD was gemcitabine at 60 mg/kg q4dx3 ip, vinorelbine at 2 mg/kg q5dx3 ip, and doxorubicin at 1.5 mg/kg q4dx3 iv.
FIG. 3B: Antitumor activity of cAC10-vcMMAE alone or in combination with GVD on subcutaneous L540cy HL tumors in SCID mice. SCID mice were implanted with L540cy HL cells in the right flank. Groups of mice (8-10/group) were untreated or received cAC10-vcMMAE (1 mg/kg, q4dx3, ip) alone, GVD alone, or combination treatment with cAC10-vcMMAE and GVD when tumor sizes averaged approximately 100 mm$^3$. The treatment schedule of GVD was gemcitabine at 60 mg/kg q4dx3 ip, vinorelbine at 2 mg/kg q5dx3 ip, and doxorubicin at 1.5 mg/kg q4dx3 iv.

| Treatment | Median TGD (FIG. 3A) (days to quadruple) | Median TGD (FIG. 3B) (days to quadruple) | Combo vs single agent (P-vlaue) | |
|---|---|---|---|---|
| | | | (A) | (B) |
| cAC10-vcMMAE | 84.6 | 54.7 | p = 0.5089 | p = 0.0004 |
| GVD | 33.2 | 34.4 | p < 0.0001 | p = 0.0005 |
| GVD + cAC10-vcMMAE | >77 | >107 | | |

The effect of combining cAC10-vcMMAE with vinorelbine was studied. For this purpose, mice were implanted with L540cy tumors and treated with cAC10-vcMMAE and vinorelbine, either alone or combined. Treatment was initiated at 100 mm³ tumor volume for two separate experiments that were conducted (4A and 4B). In the first experiment, 1/6 durable responses were seen with the combination therapy whereas 1/6 durable responses were seen with cAC10-vcMMAE treatment alone and 0/6 durable responses with single arm treatment with vinorelbine. In the second experiment, 6/10 durable responses were seen with the combination therapy whereas 4/10 durable responses were seen with cAC10-vcMMAE treatment alone and 0/9 durable responses with single arm treatment with vinorelbine

TABLE 5

Figure 4:
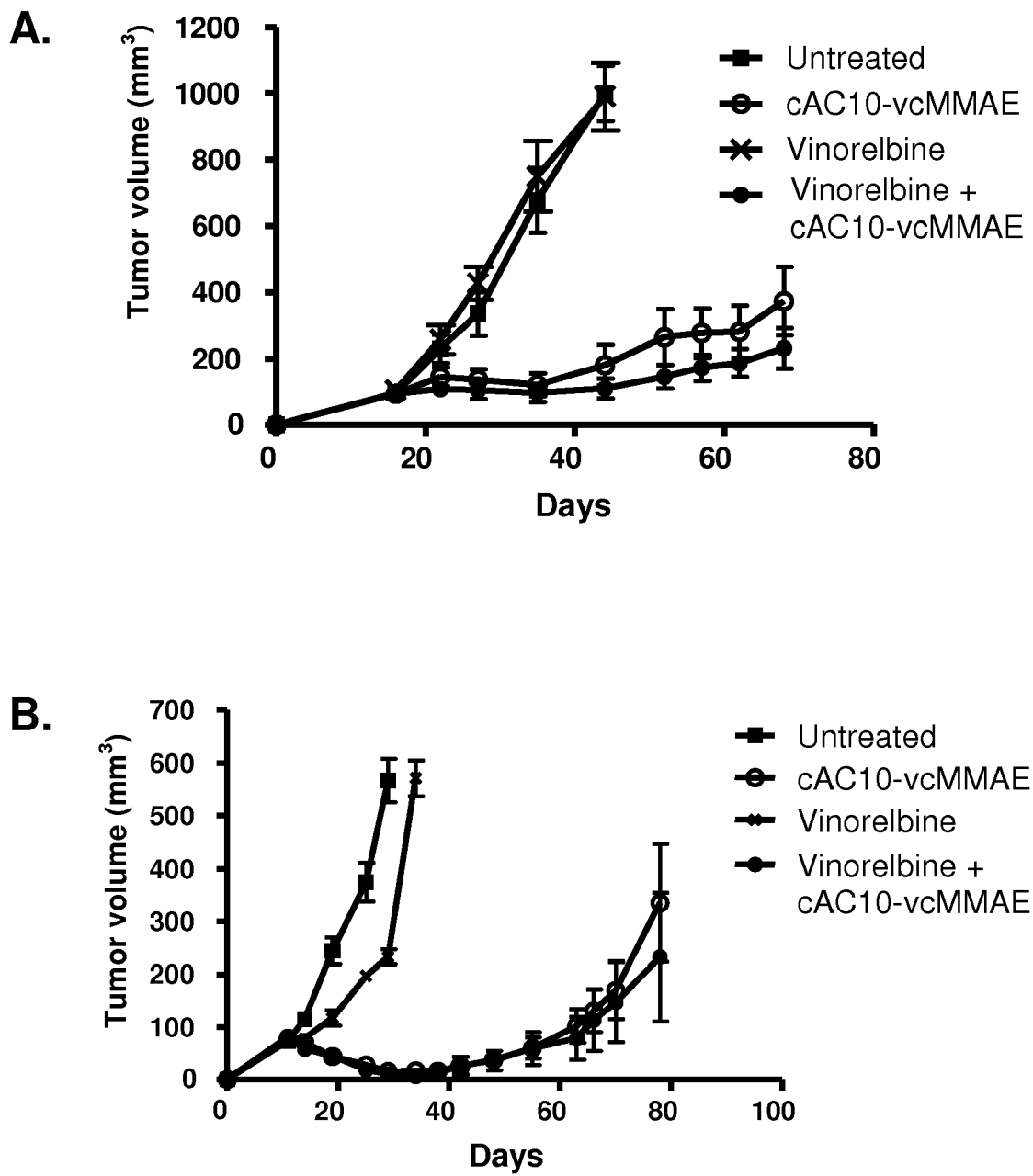
FIG. 4A: Antitumor activity of cAC10-vcMMAE alone or in combination with Vinorelbine on subcutaneous L540cy HL tumors in SCID mice. SCID mice were implanted with L540cy HL cells in the right flank. Groups of mice (5-10/group) were untreated or received cAC10-vcMMAE (1 mg/kg, q4dx3, ip) alone, Vinorelbine alone (4 mg/kg q5dx3), or combination treatment cAC10-vcMMAE and vinorelbine when tumor sizes averaged approximately 100 mm$^3$.
FIG. 4B: Antitumor activity of cAC10-vcMMAE alone or in combination with Vinorelbine on subcutaneous L540cy HL tumors in SCID mice. SCID mice were implanted with L540cy HL cells in the right flank. Groups of mice (5-10/group) were untreated or received cAC10-vcMMAE (1 mg/kg, q4dx3, ip) alone, Vinorelbine alone (4 mg/kg q5dx3), or combination treatment cAC10-vcMMAE and vinorelbine when tumor sizes averaged approximately 100 mm$^3$.

| Treatment | Median TGD (FIG. 4A) (days to quadruple) | Median TGD (FIG. 4B) (days to quadruple) | Combo vs single agent (P-vlaue) | |
|---|---|---|---|---|
| | | | (A) | (B) |
| cAC10-vcMMAE | 64 | 78.8 | p = 0.4500 | p = 0.3769 |
| Vinorelbine | 28 | 34.4 | p < 0.0004 | p = 0.0001 |
| Vinorelbine + cAC10-vcMMAE | 71 | >78 | | |

The effect of combining cAC10-vcMMAE with doxorubicin was studied. For this purpose, mice were implanted with L540cy tumors and treated with cAC10-vcMMAE and doxorubicin, either alone or combined. Treatment was initiated at 100 mm³ tumor volume for two separate experiments that were conducted (5A and 5B). In the first experiment, 0/4 durable responses were seen with the combination therapy whereas 1/6 durable responses were seen with cAC10-vcMMAE treatment alone and 0/3 durable responses with single arm treatment with doxorubicin. In the second experiment, 7/10 durable responses were seen with the combination therapy whereas 4/10 durable responses were seen with cAC10-vcMMAE treatment alone and 0/9 durable responses with single arm treatment with doxorubicin

TABLE 6

Figure 5:
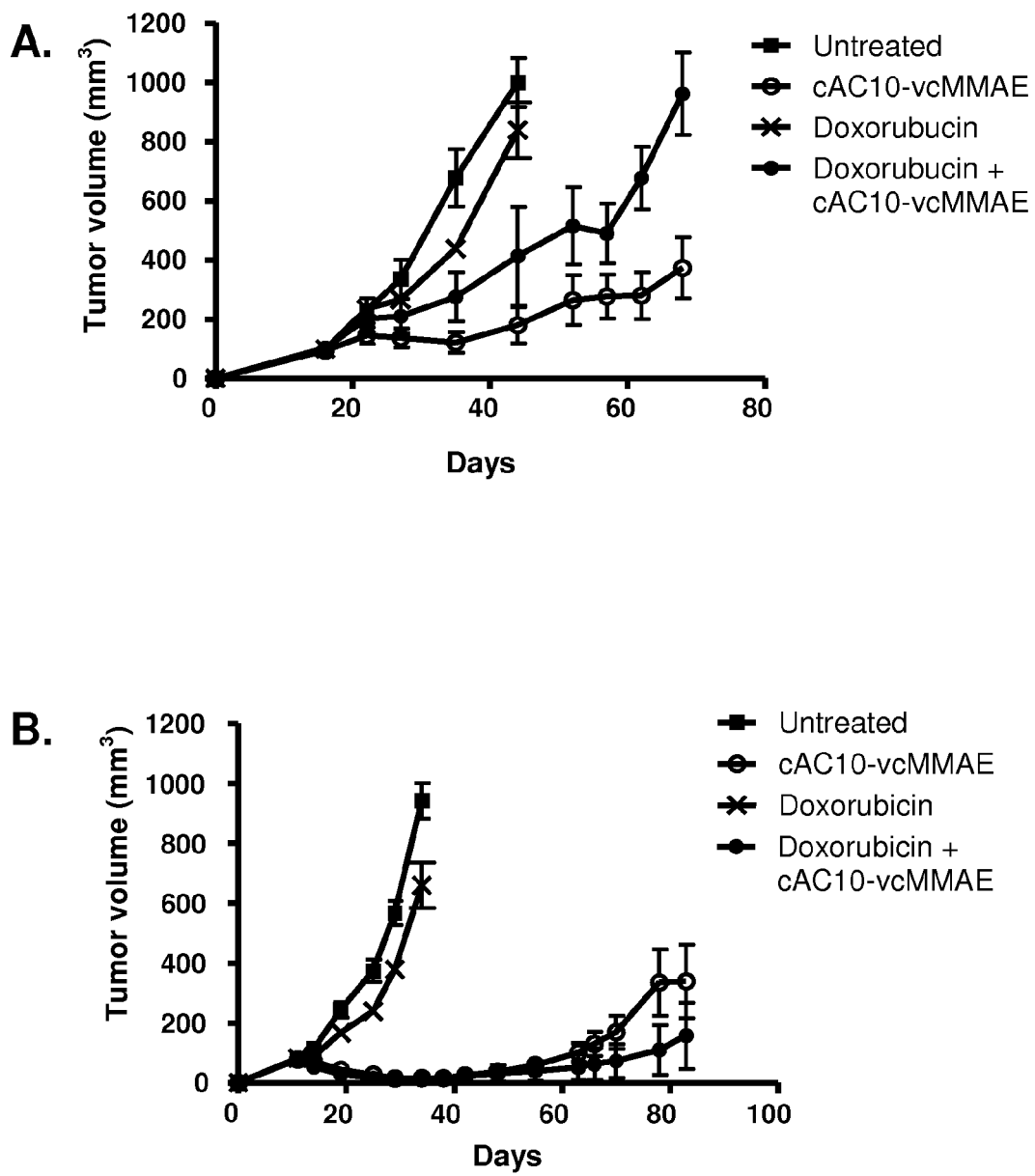
FIG. 5A: Antitumor activity of cAC10-vcMMAE alone or in combination with Doxorubicin on subcutaneous L540cy HL tumors in SCID mice. SCID mice were implanted with L540cy HL cells in the right flank. Groups of mice (5-10/group) were untreated or received cAC10-vcMMAE (1 mg/kg, q4dx3, ip) alone, Doxorubicin alone (3 mg/kg q4dx3), or combination treatment with cAC10-vcMMAE and doxorubicin when tumor sizes averaged approximately 100 mm$^3$.
FIG. 5B: Antitumor activity of cAC10-vcMMAE alone or in combination with Doxorubicin on subcutaneous L540cy HL tumors in SCID mice. SCID mice were implanted with L540cy HL cells in the right flank. Groups of mice (5-10/group) were untreated or received cAC10-vcMMAE (1 mg/kg, q4dx3, ip) alone, Doxorubicin alone (1.5 mg/kg q4dx3), or combination treatment with cAC10-vcMMAE and doxorubicin when tumor sizes averaged approximately 100 mm$^3$.

| Treatment | Median TGD (FIG. 5A) (days to quadruple) | Median TGD (FIG. 5B) (days to quadruple) | Combo vs single agent (P-vlaue) | |
|---|---|---|---|---|
| | | | (A) | (B) |
| cAC10-vcMMAE | 64 | 78.8 | p = 0.0140 | p = 0.0762 |
| Doxorubicin | 32 | 27.2 | p < 0.0067 | p = 0.0001 |
| Doxorubicin + cAC10-vcMMAE | 52 | >78 | | |

The effect of combining cAC10-vcMMAE with vinblastine was studied. For this purpose, mice were implanted with L540cy tumors and treated with cAC10-vcMMAE and vinblastine, either alone or combined. Treatment was initiated at 300 mm³ tumor volume (6). 0/10 durable responses were seen with the combination therapy whereas 1/8 durable responses were seen with cAC10-vcMMAE treatment alone and 0/10 durable responses with single arm treatment with vinblastine.

TABLE 7

Figure 6:
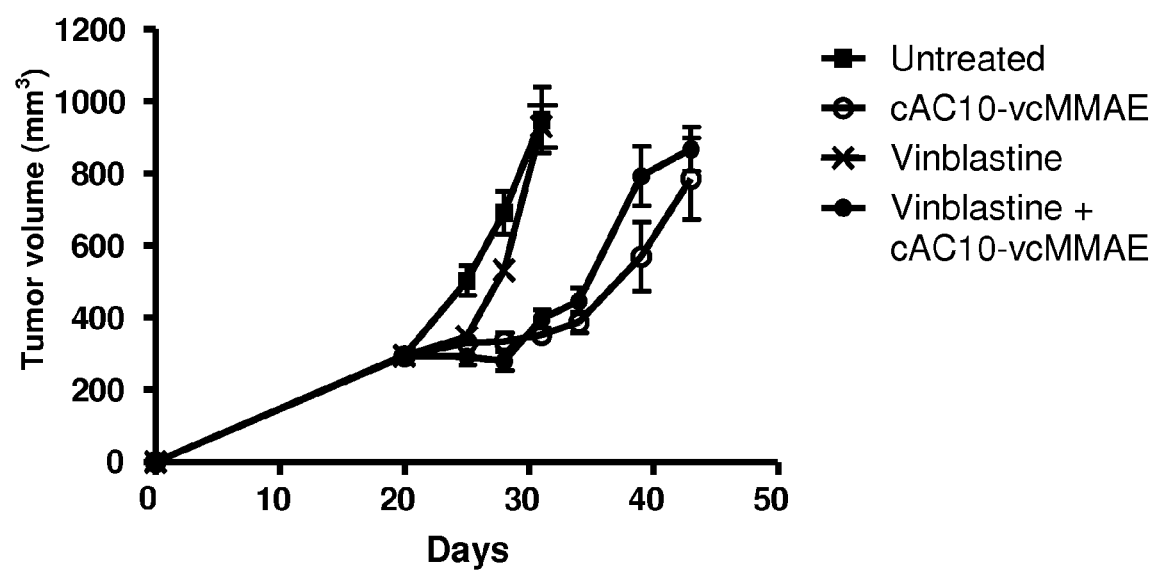
FIG. 6: Antitumor activity of cAC10-vcMMAE alone or in combination with Vinblastine on subcutaneous L540cy HL tumors in SCID mice. SCID mice were implanted with L540cy HL cells in the right flank. Groups of mice (7-10/group) were untreated or received cAC10-vcMMAE (1 mg/kg, q4dx3, ip) alone, Vinblastine alone (0/1 mg/kg q4dx3), or combination treatment with cAC10-vcMMAE and vinblastine when tumor sizes averaged approximately 300 mm$^3$.

| Treatment | Median TGD (FIG. 6) (days to triple) | Combo vs single agent (P-vlaue) |
|---|---|---|
| cAC10-vcMMAE | 45.9 | p = 0.5970 |
| Vinblastine | 30.93 | p < 0.0001 |
| Vinblastine + cAC10-vcMMAE | 55.7 | |

Example 2

Combination of the Antibody-Drug Conjugate cAC10-mcMMAF with Gemcitabine for the Treatment of HL The effects of combining cAC10-mcMMAF treatment with gemcitabine was studied in the same manner as the experiments with cAC10-vcMMAE. A 1 mg/kg, q4dx3 treatment schedule for cAC10-mcMMAF was selected. At day 51 of the experiment, 9/10 durable responses were seen with the combination therapy whereas 0/10 durable responses were seen with cAC10-mcMMAF treatment alone and 0/10 durable responses with single arm treatment with gemcitabine. The experiment is in its 51rst day and is not yet complete.

---

What is claimed is:

1. A method for treating Hodgkin lymphoma in a subject, the method comprising administering to a subject in need thereof a chemotherapeutic regimen comprising doxorubicin, bleomycin, vinblastine and dacarbazine and an antibody-drug conjugate compound, wherein said antibody-drug conjugate is an anti-CD30 antibody conjugated to an auristatin compound and administration of said antibody-drug conjugate compound and chemotherapeutic regimen provides a synergistic effect in the treatment of Hodgkin lymphoma in the patient.

2. The method of claim 1 wherein said antibody-drug conjugate compound is delivered over a treatment cycle wherein the total dose over the treatment cycle is from about 0.1 mg/kg to about 3.8 mg/kg of the subject's body weight.

3. The method of claim 2 wherein the treatment cycle is three or four weeks.

4. The method of claim 1 wherein said antibody-drug conjugate compound is administered in a dose range of 0.2 to 1.2 mg/kg of the subject's body weight per dose.

5. The method of claim 1 wherein the antibody-drug conjugate compound and chemotherapeutic regimen comprising doxorubicin, bleomycin, vinblastine and dacarbazine are administered during a treatment cycle of three or four weeks and no additional anti-cancer agents are administered during the treatment cycle.

6. The method of claim 1 wherein said subject has relapsed or refractory Hodgkin lymphoma and has not previously been treated with said chemotherapeutic regimen.

7. The method of claim 1 wherein the antibody-drug conjugate compound is administered for two or more treatment cycles.

8. The method of claim 1 wherein the auristatin compound is conjugated to the anti-CD30 antibody via a linker that is cleavable under intracellular conditions, such that cleavage of the linker releases the auristatin compound from the antibody in the intracellular environment.

9. The method of claim 8 wherein the antibody-drug conjugate compound has the following structure:

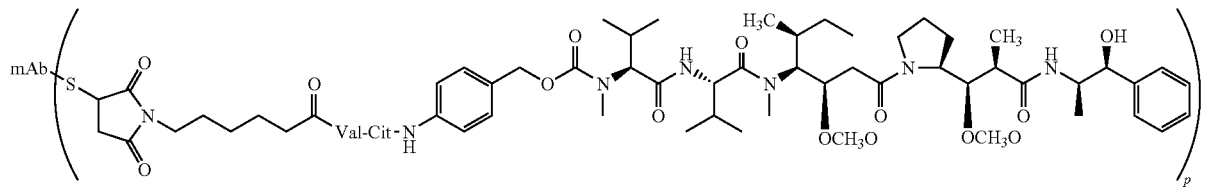

wherein mAb-s- represents the anti-CD30 antibody and p ranges from 1 to about 10.

10. The method of claim 1 wherein the auristatin compound is conjugated to the anti-CD30 antibody via a linker that is not cleavable under intracellular conditions and the auristatin compound is released by antibody degradation.

11. The method of claim 10 wherein the antibody-drug conjugate compound has the following structure:

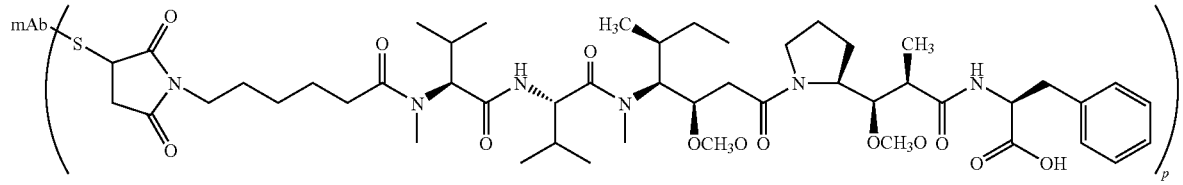

wherein mAb-s- represents the anti-CD30 antibody and p ranges from 1 to about 10.

12. The method of claim 1 wherein said anti-CD30 antibody is a chimeric AC10 antibody or competes for binding with a chimeric AC10 antibody.

13. The method of claim 12 wherein the anti-CD30 antibody is a chimeric AC10 antibody.

* * * * *

UNITED STATES PATENT AND TRADEMARK OFFICE
CERTIFICATE OF CORRECTION

| | | |
|---|---|---|
| PATENT NO. | : 8,263,083 B2 | Page 1 of 1 |
| APPLICATION NO. | : 12/681599 | |
| DATED | : September 11, 2012 | |
| INVENTOR(S) | : Ezogelin Oflazoglu et al. | |

It is certified that error appears in the above-identified patent and that said Letters Patent is hereby corrected as shown below:

In the Claims

Claim 9, Column 88, Line 37 "structure:

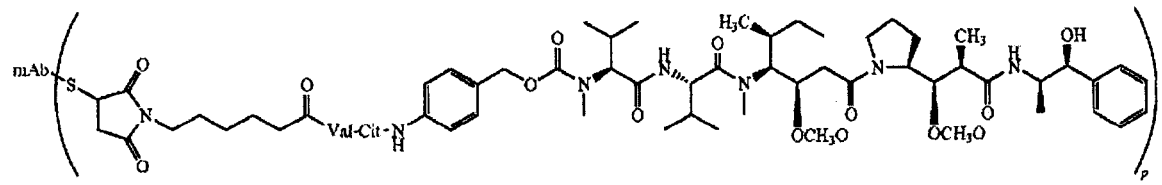

wherein" should read --structure:

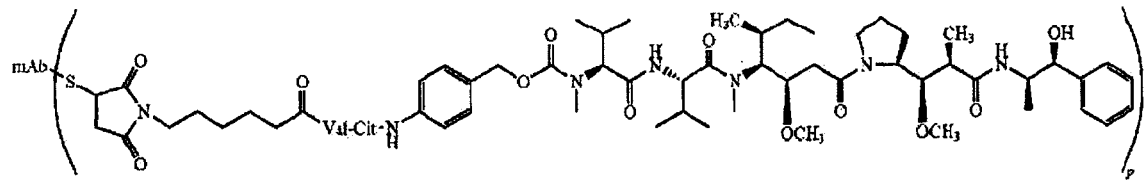

wherein--

Claim 11, Column 88, Line 37 "structure:

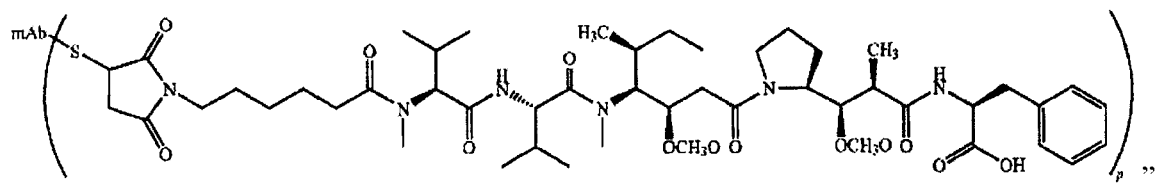

should read --structure:

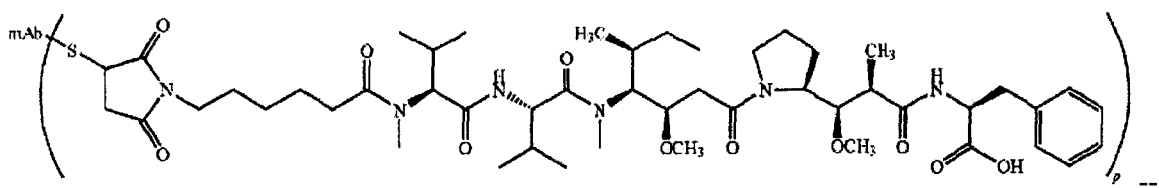

--

Signed and Sealed this
Twenty-fifth Day of December, 2012

David J. Kappos
*Director of the United States Patent and Trademark Office*

SEQUENCE LISTING

```
<160> NUMBER OF SEQ ID NOS: 34

<210> SEQ ID NO 1
<211> LENGTH: 351
<212> TYPE: DNA
<213> ORGANISM: Mus musculus
<220> FEATURE:
<221> NAME/KEY: CDS
<222> LOCATION: (1)..(351)

<400> SEQUENCE: 1 cag atc cag ctg cag cag tct gga cct gag gtg gtg aag cct ggg gct      48
Gln Ile Gln Leu Gln Gln Ser Gly Pro Glu Val Val Lys Pro Gly Ala
1               5                   10                  15 tca gtg aag ata tcc tgc aag gct tct ggc tac acc ttc act gac tac      96
Ser Val Lys Ile Ser Cys Lys Ala Ser Gly Tyr Thr Phe Thr Asp Tyr
            20                  25                  30 tat ata acc tgg gtg aag cag aag cct gga cag gga ctt gag tgg att     144
Tyr Ile Thr Trp Val Lys Gln Lys Pro Gly Gln Gly Leu Glu Trp Ile
        35                  40                  45 gga tgg att tat cct gga agc ggt aat act aag tac aat gag aag ttc     192
Gly Trp Ile Tyr Pro Gly Ser Gly Asn Thr Lys Tyr Asn Glu Lys Phe
    50                  55                  60 aag ggc aag gcc aca ttg act gta gac aca tcc tcc agc aca gcc ttc     240
Lys Gly Lys Ala Thr Leu Thr Val Asp Thr Ser Ser Ser Thr Ala Phe
65                  70                  75                  80 atg cag ctc agc agc ctg aca tct gag gac act gct gtc tat ttc tgt     288
Met Gln Leu Ser Ser Leu Thr Ser Glu Asp Thr Ala Val Tyr Phe Cys
                85                  90                  95 gcg aac tat ggt aac tac tgg ttt gct tac tgg ggc caa ggg act cag     336
Ala Asn Tyr Gly Asn Tyr Trp Phe Ala Tyr Trp Gly Gln Gly Thr Gln
            100                 105                 110 gtc act gtc tct gca                                                  351
Val Thr Val Ser Ala
        115

<210> SEQ ID NO 2
<211> LENGTH: 117
<212> TYPE: PRT
<213> ORGANISM: Mus musculus

<400> SEQUENCE: 2

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Thr Trp Val Lys Gln Lys Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ser Ser Thr Ala Phe
65                  70                  75                  80
```

```
Met Gln Leu Ser Ser Leu Thr Ser Glu Asp Thr Ala Val Tyr Phe Cys
                85                  90                  95

Ala Asn Tyr Gly Asn Tyr Trp Phe Ala Tyr Trp Gly Gln Gly Thr Gln
            100                 105                 110

Val Thr Val Ser Ala
        115

<210> SEQ ID NO 3
<211> LENGTH: 15
<212> TYPE: DNA
<213> ORGANISM: Mus musculus

<400> SEQUENCE: 3
gactactata taacc                                                      15

<210> SEQ ID NO 4
<211> LENGTH: 5
<212> TYPE: PRT
<213> ORGANISM: Mus musculus

<400> SEQUENCE: 4

Asp Tyr Tyr Ile Thr
1               5

<210> SEQ ID NO 5
<211> LENGTH: 51
<212> TYPE: DNA
<213> ORGANISM: Mus musculus

<400> SEQUENCE: 5
tggatttatc ctggaagcgg taatactaag tacaatgaga agttcaaggg c               51

<210> SEQ ID NO 6
<211> LENGTH: 17
<212> TYPE: PRT
<213> ORGANISM: Mus musculus

<400> SEQUENCE: 6

Trp Ile Tyr Pro Gly Ser Gly Asn Thr Lys Tyr Asn Glu Lys Phe Lys
1               5                   10                  15

Gly

<210> SEQ ID NO 7
<211> LENGTH: 24
<212> TYPE: DNA
<213> ORGANISM: Mus musculus

<400> SEQUENCE: 7
tatggtaact actggtttgc ttac                                            24

<210> SEQ ID NO 8
<211> LENGTH: 8
<212> TYPE: PRT
<213> ORGANISM: Mus musculus

<400> SEQUENCE: 8

Tyr Gly Asn Tyr Trp Phe Ala Tyr
1               5

<210> SEQ ID NO 9
<211> LENGTH: 333
<212> TYPE: DNA
<213> ORGANISM: Mus musculus
```

<220> FEATURE:
<221> NAME/KEY: CDS
<222> LOCATION: (1)..(333)

<400> SEQUENCE: 9

```
gac att gtg ctg acc caa tct cca gct tct ttg gct gtg tct cta ggg      48
Asp Ile Val Leu Thr Gln Ser Pro Ala Ser Leu Ala Val Ser Leu Gly
1               5                   10                  15 cag agg gcc acc atc tcc tgc aag gcc agc caa agt gtt gat ttt gat      96
Gln Arg Ala Thr Ile Ser Cys Lys Ala Ser Gln Ser Val Asp Phe Asp
            20                  25                  30 ggt gat agt tat atg aac tgg tac caa cag aaa cca gga cag cca ccc     144
Gly Asp Ser Tyr Met Asn Trp Tyr Gln Gln Lys Pro Gly Gln Pro Pro
        35                  40                  45 aaa gtc ctc atc tat gct gca tcc aat cta gaa tct ggg atc cca gcc     192
Lys Val Leu Ile Tyr Ala Ala Ser Asn Leu Glu Ser Gly Ile Pro Ala
    50                  55                  60 agg ttt agt ggc agt ggg tct ggg aca gac ttc acc ctc aac atc cat     240
Arg Phe Ser Gly Ser Gly Ser Gly Thr Asp Phe Thr Leu Asn Ile His
65                  70                  75                  80 cct gtg gag gag gag gat gct gca acc tat tac tgt cag caa agt aat     288
Pro Val Glu Glu Glu Asp Ala Ala Thr Tyr Tyr Cys Gln Gln Ser Asn
                85                  90                  95 gag gat ccg tgg acg ttc ggt gga ggc acc aag ctg gaa atc aaa         333
Glu Asp Pro Trp Thr Phe Gly Gly Gly Thr Lys Leu Glu Ile Lys
            100                 105                 110
```

<210> SEQ ID NO 10
<211> LENGTH: 111
<212> TYPE: PRT
<213> ORGANISM: Mus musculus

<400> SEQUENCE: 10

```
Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Trp Thr Phe Gly Gly Gly Thr Lys Leu Glu Ile Lys
            100                 105                 110
```

<210> SEQ ID NO 11
<211> LENGTH: 45
<212> TYPE: DNA
<213> ORGANISM: Mus musculus

<400> SEQUENCE: 11
aaggccagcc aaagtgttga ttttgatggt gatagttata tgaac           45

<210> SEQ ID NO 12
<211> LENGTH: 15
<212> TYPE: PRT
<213> ORGANISM: Mus musculus

<400> SEQUENCE: 12

```
Lys Ala Ser Gln Ser Val Asp Phe Asp Gly Asp Ser Tyr Met Asn
1               5                   10                  15
```

<210> SEQ ID NO 13
<211> LENGTH: 21
<212> TYPE: DNA
<213> ORGANISM: Mus musculus

<400> SEQUENCE: 13
gctgcatcca atctagaatc t                                              21

<210> SEQ ID NO 14
<211> LENGTH: 7
<212> TYPE: PRT
<213> ORGANISM: Mus musculus

<400> SEQUENCE: 14

```
Ala Ala Ser Asn Leu Glu Ser
1               5
```

<210> SEQ ID NO 15
<211> LENGTH: 27
<212> TYPE: DNA
<213> ORGANISM: Mus musculus

<400> SEQUENCE: 15
cagcaaagta atgaggatcc gtggacg                                        27

<210> SEQ ID NO 16
<211> LENGTH: 9
<212> TYPE: PRT
<213> ORGANISM: Mus musculus

<400> SEQUENCE: 16

```
Gln Gln Ser Asn Glu Asp Pro Trp Thr
1               5
```

<210> SEQ ID NO 17
<211> LENGTH: 375
<212> TYPE: DNA
<213> ORGANISM: Mus musculus
<220> FEATURE:
<221> NAME/KEY: CDS
<222> LOCATION: (1)..(375)

<400> SEQUENCE: 17

```
gag gtg aag ctg gtg gag tct gga gga ggc ttg gta cag cct ggg ggt     48
Glu Val Lys Leu Val Glu Ser Gly Gly Gly Leu Val Gln Pro Gly Gly
1               5                   10                  15 tct ctg aga ctc tcc tgt gca act tct ggg ttc acc ttc agt gat tac     96
Ser Leu Arg Leu Ser Cys Ala Thr Ser Gly Phe Thr Phe Ser Asp Tyr
            20                  25                  30 tat atg aac tgg gtc cgc cag cct cca gga aag gct ctt gag tgg ttg    144
Tyr Met Asn Trp Val Arg Gln Pro Pro Gly Lys Ala Leu Glu Trp Leu
        35                  40                  45 ggt ttt att aga aac aaa gct aat ggt tac aca aca gag ttc agt gca    192
Gly Phe Ile Arg Asn Lys Ala Asn Gly Tyr Thr Thr Glu Phe Ser Ala
    50                  55                  60 tct gtg atg ggt cgg ttc acc atc tcc aga gat gat tcc caa agc atc    240
Ser Val Met Gly Arg Phe Thr Ile Ser Arg Asp Asp Ser Gln Ser Ile
65                  70                  75                  80 ctc tat ctt cag atg aac acc ctg aga gct gag gac agt gcc act tat    288
Leu Tyr Leu Gln Met Asn Thr Leu Arg Ala Glu Asp Ser Ala Thr Tyr
                85                  90                  95
```

```
tac tgt gca aga gat ccc ccc tat ggt aac ccc cat tat tat gct atg    336
Tyr Cys Ala Arg Asp Pro Pro Tyr Gly Asn Pro His Tyr Tyr Ala Met
            100                 105                 110 gac tac tgg ggt caa gga acc tca gtc acc gtc tcc tca                375
Asp Tyr Trp Gly Gln Gly Thr Ser Val Thr Val Ser Ser
        115                 120                 125

<210> SEQ ID NO 18
<211> LENGTH: 125
<212> TYPE: PRT
<213> ORGANISM: Mus musculus

<400> SEQUENCE: 18

Glu Val Lys Leu Val Glu Ser Gly Gly Leu Val Gln Pro Gly Gly
1               5                   10                  15

Ser Leu Arg Leu Ser Cys Ala Thr Ser Gly Phe Thr Phe Ser Asp Tyr
                20                  25                  30

Tyr Met Asn Trp Val Arg Gln Pro Pro Gly Lys Ala Leu Glu Trp Leu
            35                  40                  45

Gly Phe Ile Arg Asn Lys Ala Asn Gly Tyr Thr Thr Glu Phe Ser Ala
        50                  55                  60

Ser Val Met Gly Arg Phe Thr Ile Ser Arg Asp Asp Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Ala Arg Asp Pro Pro Tyr Gly Asn Pro His Tyr Tyr Ala Met
            100                 105                 110

Asp Tyr Trp Gly Gln Gly Thr Ser Val Thr Val Ser Ser
        115                 120                 125

<210> SEQ ID NO 19
<211> LENGTH: 15
<212> TYPE: DNA
<213> ORGANISM: Mus musculus

<400> SEQUENCE: 19
gattactata tgaac                                                    15

<210> SEQ ID NO 20
<211> LENGTH: 5
<212> TYPE: PRT
<213> ORGANISM: Mus musculus

<400> SEQUENCE: 20

Asp Tyr Tyr Met Asn
1               5

<210> SEQ ID NO 21
<211> LENGTH: 57
<212> TYPE: DNA
<213> ORGANISM: Mus musculus

<400> SEQUENCE: 21
tttattagaa acaaagctaa tggttacaca acagagttca gtgcatctgt gatgggt      57

<210> SEQ ID NO 22
<211> LENGTH: 19
<212> TYPE: PRT
<213> ORGANISM: Mus musculus

<400> SEQUENCE: 22
```

```
Phe Ile Arg Asn Lys Ala Asn Gly Tyr Thr Thr Glu Phe Ser Ala Ser
1               5                   10                  15

Val Met Gly

<210> SEQ ID NO 23
<211> LENGTH: 42
<212> TYPE: DNA
<213> ORGANISM: Mus musculus

<400> SEQUENCE: 23 gatccccct atggtaaccc ccattattat gctatggact ac                           42

<210> SEQ ID NO 24
<211> LENGTH: 14
<212> TYPE: PRT
<213> ORGANISM: Mus musculus

<400> SEQUENCE: 24

Asp Pro Pro Tyr Gly Asn Pro His Tyr Tyr Ala Met Asp Tyr
1               5                   10

<210> SEQ ID NO 25
<211> LENGTH: 333
<212> TYPE: DNA
<213> ORGANISM: Mus musculus
<220> FEATURE:
<221> NAME/KEY: CDS
<222> LOCATION: (1)..(333)

<400> SEQUENCE: 25 gac att gtg ctg acc cag tct cct gct tcc tta gct gtt tct ctg ggg        48
Asp Ile Val Leu Thr Gln Ser Pro Ala Ser Leu Ala Val Ser Leu Gly
1               5                   10                  15 cag agg gcc acc atc tca tgc agg gcc agc aaa agt gtc agt gca tct        96
Gln Arg Ala Thr Ile Ser Cys Arg Ala Ser Lys Ser Val Ser Ala Ser
                20                  25                  30 ggc tat aat tat atg cac tgg tac caa cag aaa gca ggg cag cca ccc       144
Gly Tyr Asn Tyr Met His Trp Tyr Gln Gln Lys Ala Gly Gln Pro Pro
            35                  40                  45 aaa ctc ctc atc cat ctt gca tcc aac cta gaa tct ggg gtc cct gcc       192
Lys Leu Leu Ile His Leu Ala Ser Asn Leu Glu Ser Gly Val Pro Ala
        50                  55                  60 agg ttc agt ggc agt ggg tct ggg aca gac ttc acc ctc aac atc cat       240
Arg Phe Ser Gly Ser Gly Ser Gly Thr Asp Phe Thr Leu Asn Ile His
65                  70                  75                  80 cct gtg gag gag gag gat gct tca acc tat tac tgt cag cac agt ggg       288
Pro Val Glu Glu Glu Asp Ala Ser Thr Tyr Tyr Cys Gln His Ser Gly
                85                  90                  95 gag ctt cca ttc acg ttc ggc tcg ggg aca aag ttg gaa ata aaa           333
Glu Leu Pro Phe Thr Phe Gly Ser Gly Thr Lys Leu Glu Ile Lys
            100                 105                 110

<210> SEQ ID NO 26
<211> LENGTH: 111
<212> TYPE: PRT
<213> ORGANISM: Mus musculus

<400> SEQUENCE: 26

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ala Ser
                20                  25                  30

Gly Tyr Asn Tyr Met His Trp Tyr Gln Gln Lys Ala Gly Gln Pro Pro
```

```
            35                  40                  45
Lys Leu Leu Ile His Leu Ala Ser Asn Leu Glu Ser Gly Val Pro Ala
         50                  55                  60

Arg Phe Ser Gly Ser Gly Ser Gly Thr Asp Phe Thr Leu Asn Ile His
 65                  70                  75                  80

Pro Val Glu Glu Glu Asp Ala Ser Thr Tyr Tyr Cys Gln His Ser Gly
                 85                  90                  95

Glu Leu Pro Phe Thr Phe Gly Ser Gly Thr Lys Leu Glu Ile Lys
            100                 105                 110

<210> SEQ ID NO 27
<211> LENGTH: 45
<212> TYPE: DNA
<213> ORGANISM: Mus musculus

<400> SEQUENCE: 27
agggccagca aaagtgtcag tgcatctggc tataattata tgcac            45

<210> SEQ ID NO 28
<211> LENGTH: 15
<212> TYPE: PRT
<213> ORGANISM: Mus musculus

<400> SEQUENCE: 28

Arg Ala Ser Lys Ser Val Ser Ala Ser Gly Tyr Asn Tyr Met His
 1               5                  10                  15

<210> SEQ ID NO 29
<211> LENGTH: 21
<212> TYPE: DNA
<213> ORGANISM: Mus musculus

<400> SEQUENCE: 29
cttgcatcca acctagaatc t                                      21

<210> SEQ ID NO 30
<211> LENGTH: 7
<212> TYPE: PRT
<213> ORGANISM: Mus musculus

<400> SEQUENCE: 30

Leu Ala Ser Asn Leu Glu Ser
 1               5

<210> SEQ ID NO 31
<211> LENGTH: 27
<212> TYPE: DNA
<213> ORGANISM: Mus musculus

<400> SEQUENCE: 31
cagcacagtg gggagcttcc attcacg                                27

<210> SEQ ID NO 32
<211> LENGTH: 9
<212> TYPE: PRT
<213> ORGANISM: Mus musculus

<400> SEQUENCE: 32

Gln His Ser Gly Glu Leu Pro Phe Thr
 1               5

<210> SEQ ID NO 33
<211> LENGTH: 330
```

<212> TYPE: PRT
<213> ORGANISM: Homo sapiens

<400> SEQUENCE: 33

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 34
<211> LENGTH: 106
<212> TYPE: PRT
<213> ORGANISM: Homo sapiens

<400> SEQUENCE: 34

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
```

-continued

```
                        20                    25                          30
Pro Arg Glu Ala Lys Val Gln Trp Lys Val Asp Asn Ala Leu Gln Ser
            35                    40                          45

Gly Asn Ser Gln Glu Ser Val Thr Glu Gln Asp Ser Lys Asp Ser Thr
        50                    55                  60

Tyr Ser Leu Ser Ser Thr Leu Thr Leu Ser Lys Ala Asp Tyr Glu Lys
65                      70              75                      80

His Lys Val Tyr Ala Cys Glu Val Thr His Gln Gly Leu Ser Ser Pro
                85                      90                  95

Val Thr Lys Ser Phe Asn Arg Gly Glu Cys
            100                 105
```